(12) United States Patent
Bondinell et al.

(10) Patent No.: US 6,518,267 B1
(45) Date of Patent: Feb. 11, 2003

(54) PROTEASE INHIBITORS

(75) Inventors: William Edward Bondinell, Wayne, PA (US); Renee Louise DesJarlais, St. Davids, PA (US); Daniel Frank Veber, Ambler, PA (US); Dennis Shinji Yamashita, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/700,828

(22) PCT Filed: May 20, 1999

(86) PCT No.: PCT/US99/11266

§ 371 (c)(1),
(2), (4) Date: Nov. 21, 2000

(87) PCT Pub. No.: WO99/59526

PCT Pub. Date: Nov. 25, 1999

Related U.S. Application Data

(60) Provisional application No. 60/086,557, filed on May 21, 1998.

(51) Int. Cl.[7] .................... A61K 31/535; A61K 31/36; C07D 219/12; C07D 413/00; C07D 307/78

(52) U.S. Cl. ................. 514/231.5; 514/235.2; 514/332; 514/336; 514/312; 514/340; 514/357; 514/464; 544/106; 544/111; 544/129; 546/156; 546/186; 546/192; 546/193; 546/195; 546/207; 549/469

(58) Field of Search ............ 514/231.5, 235.2, 514/312, 332, 336, 340, 357, 464; 544/106, 111, 129; 546/156, 186, 192, 193, 195, 207; 549/469

(56) References Cited

FOREIGN PATENT DOCUMENTS

WO          97/16433     * 5/1997

OTHER PUBLICATIONS

D. S. Yamashita, "Solid phase synthesis of Combinatorial Array of 1,3–Bisd . . . ", (1999), Chem. Abstracts, Database CA on STN, No. 131:44415.

Bondinell, et al., "Protease Inhibitors", (1998), Database CA on STN, No. 130:25340, Abstract WO 98/50342.

Chemical Abstracts 129:272204, abstract of J Am Chem Soc, 120(35), 9114–9115, 1998.*

* cited by examiner

Primary Examiner—D. Margaret Seaman
(74) Attorney, Agent, or Firm—Linda E. Hall; Stephen Venetianer; Charles M. Kinzig

(57) ABSTRACT

The present invention provides bis-aminomethyl carbonyl protease inhibitors and pharmaceutically acceptable salts, hydrates and solvates thereof which inhibit proteases, including cathepsin K, pharmaceutical compositions of such compounds, and methods for treating diseases of excessive bone loss or cartilage or matrix degradation, including osteoporosis; gingival disease including gingivitis and periodontitis; arthritis, more specifically, osteoarthritis and rheumatoid arthritis; Paget's disease; hypercalcemia of malignancy; and metabolic bone disease, comprising inhibiting said bone loss or excessive cartilage or matrix degradation by administering to a patient in need thereof a compound of the present invention.

25 Claims, No Drawings

PROTEASE INHIBITORS

This is a 371 of International Application PCT/US99/11266, filed May 20, 1998, which claims benefit from the Provisional Application No. 60/086,557, filed May 21, 1998.

FIELD OF THE INVENTION

This invention relates in general to bis-aminomethyl carbonyl protease inhibitors, particularly such inhibitors of cysteine and serine proteases, more particularly compounds which inhibit cysteine proteases, even more particularly compounds which inhibit cysteine proteases of the papain superfamily, yet more particularly compounds which inhibit cysteine proteases of the cathepsin family, most particularly compounds which inhibit cathepsin K. Such compounds are particularly useful for treating diseases in which cysteine proteases are implicated, especially diseases of excessive bone or cartilage loss, e.g., osteoporosis, periodontitis, and arthritis.

BACKGROUND OF THE INVENTION

Cathepsins are a family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. Biol. Chem.* 271, 12517–12524; Drake. F. H., et al., (1996) *J. Biol. Chem.* 271, 127511–12516; Bromme. D., et al., (1996) *J. Biol. Chem.* 271, 2126–2132.

Cathepsin K has been variously denoted as cathepsin O or cathepsin $O_2$ in the literature. The designation cathepsin K is considered to be the more appropriate one.

Cathepsins function in the normal physiological process of protein degradation in animals, including humans, e.g., in the degradation of connective tissue. However, elevated levels of these enzymes in the body can result in pathological conditions leading to disease. Thus, cathepsins have been implicated as causative agents in various disease states, including but not limited to, infections by pneumocystis carinii, trypsanoma cruzi, trypsanoma brucei brucei, and Crithidia fusiculata, as well as in schistosomiasis, malaria, tumor metastasis, metachromatic leukodystrophy, muscular dystrophy, amytrophy, and the like. See International Publication Number WO 94104172, published on Mar. 3, 1994, and references cited therein. See also European Patent Application EP 0 603 873 A1, and references cited therein. Two bacterial cysteine proteases from P. gingivallis, called gingipains, have been implicated in the pathogenesis of gingivitis. Potempa, J., et al. (1994) *Perspectives in Drug Discovers and Design*, 2, 445–458.

Cathepsin K is believed to play a causative role in diseases of excessive bone or cartilage loss. Bone is composed of a protein matrix in which spindle- or plate-shaped crystals of hydroxyapatite are incorporated. Type I collagen represents the major structural protein of bone comprising approximately 90% of the protein matrix. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodelling at discrete foci throughout life. These foci, or remodelling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

Several published studies have demonstrated that inhibitors of cysteine proteases are effective at inhibiting osteoclast-mediated bone resorption, and indicate an essential role for a cysteine proteases in bone resorption. For example, Delaisse, et al., *Biocdem. J.*, 1980, 192, 365, disclose a series of protease inhibitors in a mouse bone organ culture system and suggest that inhibitors of cysteine proteases (e.g., leupeptin, Z-Phe-Ala-$CHN_2$) prevent bone resorption, while serine protease inhibitors were ineffective. Delaisse, et al., *Biochem. Biophys. Res. Commun.*, 1984, 125, 441, disclose that E-64 and leupeptin are also effective at preventing bone resorption in vivo, as measured by acute changes in serum calcium in rats on calcium deficient diets. Lerner, et al., *J. Bone Min. Res.*, 1992, 7, 433, disclose that cystatin, an endogenous cysteine protease inhibitor, inhibits PTH stimulated bone resorption in mouse calvariae. Other studies, such as by Delaisse, et al., *Bone*, 1987, 8, 305, Hill, et al., *J. Cell. Biochem.*, 1994, 56, 118, and Everts, et al., *J. Cell. Physiol.*, 1992, 150, 221, also report a correlation between inhibition of cysteine protease activity and bone resorption. Tezuka, et al., *J. Biol. Chem.*, 1994, 269, 1106, Inaoka, et al., *Biochem. Biophys. Res. Commun.*, 1995, 206, 89 and Shi, el al., *FEBS Lett.*, 1995, 357, 129 disclose that under normal conditions cathepsin K, a cysteine protease, is abundantly expressed in osteoclasts and may be the major cysteine protease present in these cells.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

Several cysieine protease inhibitors are known. Palmer, (1995) *J. Med. Chem.*, 38, 3193, disclose certain vinyl sulfones which irreversibly inhibit cysteine proteases, such as the cathepsins B. L. S. O2 and cruzain. Other classes of compounds, such as aldehydes, nitrites, α-ketocarbonyl compounds, hatomethyl ketones, diazomethyl ketones, (acyloxy)methyl ketones, ketomethylsulfonium salts and epoxy succinyl compounds have also been reported to inhibit cysteine proteases. See Palmer, id, and references cited therein.

U.S. Pat. No. 4,518,528 discloses peptidyl fluoromethyl ketones as irreversible inhibitors of cysteine protease. Published International Patent Application No. WO 94/04172, and European Patent Application Nos. EP 0 525 420 A1, EP 0 603 873 A1, and EP 0 611 756 A2 describe alkoxymethyl and mercaptomethyl ketones which inhibit the cysteine proteases cathepsins B, H and L. International Patent Application No. PCT/US94/08868 and and European Patent Application No. EP 0 623 592 A1 describe alkoxymethyl and mercaptomethyl ketones which inhibit the cysteine protease IL-1β convertase. Alkoxymethyl and mercaptomethyl ketones have also been described as inhibitors of the serine protease kininogenase (International Patent Application No. PCT/GB91/01479).

Azapeptides which are designed to deliver the azaamino acid to the active site of serine proteases, and which possess a good leaving group, are disclosed by Elmore et al., *Biochem. J.*, 1968, 107, 103, Garker et al., *Biochem. J.*, 1974, 139, 555, Gray et al., *Tetrahedron*, 1977, 33, 837, Gupton et al., *J. Biol. Chem.*, 1984, 259, 4279, Powers et al., *J. Biol. Chem.*, 1984, 259, 4288, and are known to inhibit serine proteases. In addition, Magrath et al., *J. Med. Chem.*, 1992, 35, 4279, Baggio et al., Biochemistry, 1996, 35, 3551 and Xing et al., *J. Med. Chem.* 1998, 41, 1344 disclose certain azapeptide esters as cysteine protease inhibitors.

Diacyl carbohydrazides have recently been disclosed as inhibitors of cathepsin K by Thompson et al., *Proc. Natl. Acad. Sci., U.S.A.*, 1997, 94, 14249 and in International Patent Application No. WO 97/16433.

Antipain and leupeptin are described as reversible inhibitors of cysteine protease in McConnell et al., *J. Med. Chem.*, 33, 86; and also have been disclosed as inhibitors of serine protease in Umezawa et al., 45 *Meth. Enzymol.* 678. E64 and its synthetic analogs are also well-known cysteine protease inhibitors (Barrett. *Biochem. J.*, 201, 189, and Grinde, *Biochem. Biophys. Acia.*, 701, 328).

1,3-diamido-propanones have been described as analgesic agents in U.S. Pat. Nos. 4,749,792 and 4,638,010.

Thus, a structurally diverse variety of cysteine protease inhibitors have been identified. However, these known inhibitors are not considered suitable for use as therapeutic agents in animals, especially humans, because they suffer from various shortcomings. These shortcomings include lack of selectivity, cytotoxicity, poor solubility, and overly rapid plasma clearance. A need therefore exists for methods of treating diseases caused by pathological levels of cysteine proteases, including cathepsins, especially cathepsin K, and for novel inhibitor compounds useful in such methods.

We have now discovered a novel class of bis-aminomethyl carbonyl compounds which are protease inhibitors, most particularly of cathepsin K.

SUMMARY OF THE INVENTION

An object of the present invention is to provide bis-aminomethyl carbonyl protease inhibitors, particularly such inhibitors of cysteine and serine proteases, more particularly such compounds which inhibit cysteine proteases, even more particularly such compounds which inhibit cysteine proteases of the papain superfamily, yet more particularly such compounds which inhibit cysteine proteases of the cathepsin family, most particularly such compounds which inhibit cathepsin K, and which are useful for treating diseases which may be therapeutically modified by altering the activity of such proteases.

Accordingly, in the first aspect, this invention provides a compound according to Formula I.

In another aspect, this invention provides a pharmaceutical composition comprising a compound according to Formula I and a pharmaceutically acceptable carrier, diluent or excipient.

In yet another aspect, this invention provides intermediates useful in the preparation of the compounds of Formula I.

In still another aspect, this invention provides a method of treating diseases in which the disease pathology may be therapeutically modified by inhibiting proteases, particularly cysteine and serine proteases, more particularly cysteine proteases, even more particularly cysteine proteases of the papain superfamily, yet more particularly cysteine proteases of the cathepsin family, most particularly cathepsin K.

In a particular aspect, the compounds of this invention are especially useful for treating diseases characterized by bone loss, such as osteoporosis and gingival diseases, such as gingivitis and periodontitis, or by excessive cartilage or matrix degradation, such as osteoarthritis and rheumatoid arthritis.

DETAILED DESCRIPTION OF THE INVENTION

The present invention provides compounds of Formula I:

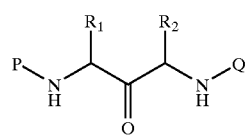

I $R_1$ and $R_2$ are independently H or $C_1$–$C_6$ alkyl, provided that $R_1$ and $R_2$ are not both $C_1$–$C_6$ alkyl;

P is

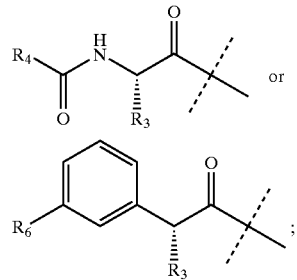

$R_3$ is $CH_2CH(CH_3)_2$, $CH_2CH_2CH_3$, $CH_2CH=CH_2$, or $CH_2Ph$;

$R_4$ is selected from the group consisting of:
  $C_0$–$C_6$ alkyl;
  N-piperizine;
  N-tetrahydroisoquinoline;
  $C_0$–$C_6$ alkyl substituted with phenyl, thiophene, benzthiazole, 2-, 3-, 4-, 5-, 6-, or 7-quinoline, naphthyl, 1-(7-nitro-2,1,3-benzoxadiazol-4-yl)-L-prolyl, $C_0$–$C_6$alkyl pyrazole, N—Cbz-2-(N,N-dimethylamino)ethylglycyl-, N-methyl pyrrole, benzoxazole, benzyloxy, $C_1$–$C_6$ alkoxy; 2, 3, or 4-pyridinyloxy; adamantyl, thieno[3,2-b] thiophene;
  phenytl; thiophene; benzothiophene; benzofuran, benzothiazole; 2-, 3-, 4-, 5-, 6-, or 7-quinoline; naphthyl; and benzoxazole, each independently substituted with one or more of $C_1$–$C_6$ alkyl, halogen, nitro, cyano, hydroxy, $C_1$–$C_6$ alkoxy, trifluoromethyl, carboxyl, carboxy $C_1$–$C_6$ alkyl ester, ($C_0$–$C_6$ alkyl)$_2$N-$C_0$–$C_6$alkyl, ($C_0$–$C_6$ alkyl)$_2$NC$_0$–$C_6$alkoxy, N—($C_0$–$C_6$)-N-piperizine, N—(N—($C_0$–$C_6$)alkyl -N-piperidine)-4-($C_0$–$C_6$) alkyl-amine, ($C_0$–$C_6$ alkyl)$_2$N-$C_0$–$C_6$alkyl-($C_0$–$C_6$ alkyl)-amine, N-morpholino-$C_0$–$C_6$alkyl, N-morpholino-$C_0$–$C_6$alkoxy, phenyl, thiophene, benzthiazole, 2, 3, 4, 5, 6, or 7 quinoline, naphthyl, $C_0$–$C_6$alkyl pyrazole, N-methyl pyrrole, benzoxazole;

benzyloxy substituted with one or more $C_1$–$C_6$ alkyl, halogen, nitro, cyano, hydroxy, $C_1$–$C_6$ alkoxy, trifluoromethyl, carboxyl, carboxy $C_1$–$C_6$ alkyl ester, phenyl, thiophene, benzthiazole, 2, 3, 4, 5, 6, or 7 quinoline, naphthyl, $C_0$–$C_6$alkyl pyrazole, N-methyl pyrrole, and benzoxazole; and pyrazine;
pyrimidine;
2,7-dimethylpyrazolo[1,5-a]pyrimidine and 4,7-dimethylpyrazolo[5,1-c][1,2,4]-triazine.

$R_6$ is selected from the group consisting of: phenyl and phenyl substituted with $C_0$–$C_6$ alkyl, N-piperidine, benzofuran; or 2, 3, or 4 pyridine;

Q is

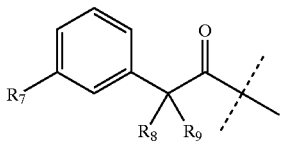

wherein:
$R_7$ is selected from the group consisting of: phenyl and phenyl substituted with ($C_0$–$C_6$ alkyl), N-piperidine, benzofuran; or 2, 3, or 4 pyridine;
$R_8$ is selected from the group consisting of: H, $CH_2CH(CH_3)_2$, $CH_2CH_2CH_3$, and $CH_2CH=CH_2$, $CH_2Ph$, when $R_9$ is H; or
$R_8$ and $R_9$ are independently selected from the group consisting of: $C_1$–$C_6$ alkyl; 3-(2-pyridyl)-phenylacetyl; 3-biphenyl-acetyl; 2-$C_1$–$C_6$ alkyl substituted 3-(2-pyridyl)-phenylacetyl; 2-$C_1$–$C_6$ alkyl substituted 3-biphenyl-acetyl; 2,2-$C_1$–$C_6$ alkyl disubstituted 3-(2-pyridyl)-phenylacetyl; 2,2-$C_1$–$C_6$ alkyl disubstituted 3-biphenyl-acetyl; phenyl sulfonyl; 2-, 3-, or 4-pyrine sulfonyl; phenyl; $C_0$–$C_6$ alkyl sulfonyl; $C_0$–$C_6$ alkyl carbonyl; and phenyl sulfonyl; phenyl; $C_0$–$C_6$ alkyl sulfonyl; or $C_0$–$C_6$ alkyl carbonyl independently substituted with one or more of $C_1$–$C_6$ alkyl, halogen, nitro, cvano, hydroxy, $C_1$–$C_6$ alkoxy, trifluoromethyl, carboxyl, carboxy $C_1$–$C_6$ alkyl ester, phenyl, thiophene, benzthiazole, 2-, 3-, 4-, 5-, 6-, or 7-quinoline, naphthyl, $C_0$–$C_6$alkyl pyrazole, N-methyl pyrrole, benzoxazole;

and pharmaceutically acceptable salts, hydrates and solvates thereof.

Compounds of Formula I selected from the following group are preferred embodiments of the present invention:

(S)-3N-(N-(thianaphthenyl-2-carbonyl)-leucinyl)-amino-1N-(3-{2-(1-oxo)-pyridyl}phenylacetyl)-amino-butan-2-one;

(S)-3N-(N-(Benzyloxycarbonyl)-L-leucinyl)amino-1N-[3-{2-(1-oxo)-pyridyl}phenylacetyl]amino-2-butanone;

(S)-3N-[N-((5-Morpholinoethyloxy)benzofuryl-2-carbonyl)-L-leucinyl)]amino-1N-[3-(2-(1-oxo)pyridyl) phenylacetyl]amino-2-butanone;

1N-(N-(thiophene-2-carbonyl)-leucinyl)-amino-3N-(3-(2-pyridyl)-phenyl acetyl)-amino-propan-2-one; 1N-(N-(3,4-Dichlorobenzoyl)-L-leucinyl)amino-3N-[3-(2-pyridyl)phenylacetyl]amino-2-propanone;

1N-(N-(methylpiperidine-4-carbonyl)-L-leucinyl)amino-3N-[3-(2-pyridyl)phenylacetyl]amino-2-propanone;

1-(N-4-((7-nitro-2,1,3-benzooxadiazole)-L-pyrrolidinyl-)-N-(L-leucinyl))-amino-3N-[3-(2-pyridyl)phenylacetyl]amino-2-propanone;

1N-(N-(5-methylimidazolyl-4-carbonyl)-L-leucinyl) amino-3N-[3-(2-pyridyl)phenylacetyl]amino-2-propanone;

1N-(N-(5-butylpyridine-2-carbonyl)-L-leucinyl)amino-3N-[3-(2-pyridyl)phenylacetyl]amino-2-propanone;

1N-[N—(Cbz-2-(N,N-dimethylamino)ethyl)-glycyl-N-L-leucinyl]amino-3N-[3-(2-pyridyl)phenylacetyl]amino-2-propanone;

1N-[N-(5-(Morpholinoethyloxy)benzofuryl-2-carbonyl)-L-leucinyl]amino-3N-[3-(2-pyridyl)phenylacetyl] amino-2-propanone;

(S)-3N-(N-(Benzothiazolidyl-6-carbonyl)-L-Leucinyl) amino-1N-[3-(2-pyridyl)phenylacetyl]amino-2-butanone;

1N-(N-(Benzyloxy-carbonyl)-L-leucinyl)amino-3N-[3-(phenyl)phenylacetyl]amino-2-propanone;

(S)-3N-(N-(5-Methoxycarbonylbenzofuryl-2-carbonyl)-L-leucinyl)amino-1N-[3-(2-pyridyl)phenylacetyl] amino-2-butanone;

(S)-3N-[N-{4-Methoxy-3-(N,N-dimethylaminoethyl) oxy}benzoyl-L-leucinyl]amino-1N-[3-(2-pyridyl) phenylacetyl]amino-2-butanone;

(S)-3N-[N-(3-(4-Methylpiperazinyl))-benzoyl}-L-leucinyl]amino-1N-[3-(2-pyridyl)phenylacetyl]amino-2-propanone;

(S)-3N-[N-{(N-Methyl-N'-(4-(1-methylpiperidinyl) amino}benzoyl}-L-leucinyl]amino-1N-[3-(2-pyridyl) phenylacetyl]amino-2-butanone;

(S)-3N-[N-{(N-Methyl-N'-(beta-N,N-dimethylaminoethyl)amino}benzoyl-L-leucinyl] amino-1N-[3-(2-pyridyl)phenylacetyl]amino-2-butanone;

(S)-3N-[N-(5-(Morpholinoethyloxy)benzofuryl-2-carbonyl)-L-leucinyl]amino-1N-[3-(2-pyridyl) phenylacetyl]amino-2-butanone;

(S)-3N-{N-(4-Methyl[4-trifluoromethyl)phenyl]thiazole-5-carbonyl)-L-leucinyl)]}-amino-1N-[3-(2-pyridyl) phenylacetyl]amino-2-butanone;

1N-(N-(biphenyl)-4-carbonyl)-leucinyl)-amino-3N-(3-(2-pyridyl)-phenylacetyl)-amino-propan-2-one; 1N-(N-(indole-2-carbonyl)-leucinyl)-amino-3N -(3-(2-pyridyl)-phenylacetyl)-amino-propan-2-one;

1N-(N-(indole-6-carbonyl)-leucinyl)-amino-3N-(3-(2-pyridyl)-phenylacetyl)-amino-propan-2-one;

1N-(N-(adamantane-1-carbonyl)-leucinyl)-amino-3N-(3-(2-pyridyl)-phenylacetyl)-amino-propan-2-one;

1N-(N-(1-methoxy-2-naphthoyl)-leucinyl)-amino-3N-(3-(2-pyridyl)-phenylacetyl)-amino-propan-2-one;

1N-(N-(benzoyl)-leucinyl)-amino-3N-(3-(2-pyridyl)-phenylacetyl)-amino-propan-2-one;

1N-(N-(thieno[3,2-b]thiophene-2-carbonyl)-leucinyl)-amino-3N-(3-(2-pyridyl)-phenylacetyl)-amino-propan-2-one;

1N-(N-(4-cyclohexylbenzoyl)-leucinyl)-amino-3N-(3-(2-pyridyl)-phenylacetyl)-amino-propan-2-one;

1N-(N-(1-methylpyrrole-2-carbonyl)-leucinyl)-amino-3N-(3-(2-pyridyl)-phenylacetyl)-amino-propan-2-one;

1N-(N-(4-methoxybenzoyl)-leucinyl)-amino-3N-(3-(2-pyridyl)-phenylacetyl)-amino-propan-2-one;

1N-(N-(thiophene-3-carbonyl)-leucinyl)-amino-3N-(3-(2-pyridyl)-phenylacetyl)-amino-propan-2-one;

1N-(N-(4-(4'-ethylbiphenyl)carbonyl)-leucinyl)-amino-3N-(3-(2-pyridyl)-phenylacetyl)-amino-propan-2-one;

1N-(N-(pyrazine-2-carbonyl)-leucinyl)-amino-3N-(3-(2-pyridyl)-phenylacetyl)-amino-propan-2-one;

1N-(N-(2,7-dimethylpyrazolo[1,5-a]pyrimidine-6-carbonyl)-leucinyl)-amino-3N-(3-(2-pyridyl)-phenylacetyl)-amino-propan-2-one;

1N-(N-(4,7-dimethylpyrazolo[5,1-c][1,2,4]triazine-3-carbonyl)-leucinyl)-amino-3N-(3-(2-pyridyl)-phenylacetyl)-amino-propan-2-one;

1N-(N-thianaphthenyl-2-carbonyl)-leucinyl)-amino-3N-(3-(6-methyl-2-pyridyl)-phenylacetyl)-amino-propan-2-one;

1N-(N-thianaphthenyl-2-carbonyl)-leucinyl)-amino-3N-(3-(5-methyl-2-pyridyl)-phenylacetyl)-amino-propan-2-one;1N-(N-(4-trifluoromethylbenzoyl)-leucinyl)-amino-3N-(3-(6-methyl-2-pyridyl)-phenylacetyl)-amino-propan-2-one;

1N-(N-(4-trifluoromethylbenzoyl)-leucinyl)-amino-3N-(3-(4-methyl-2-pyridyl)-phenylacetyl)-amino-propan-2-one;

1N-(N-(N-tert-butoxycarbonyl-leucinyl)-amino-3N-(3-(2-pyridyl)phenylacetyl)-amino-propan-2-one;

1N-(N-(4-((2-dimethylamino)ethoxy)-benzoyl)-leucinyl)-amino-3N-(3-(2-pyridyl)phenylacetyl)-amino-propan-2-one; 1N-(N-(4-((2-dimethylamino)ethoxy)-3-methoxy-benzoyl)-leucinyl)-amino-3N-(3-(2-pyridyl)phenylacetyl)-amino-propan-2-one;

1N-(N-(3-(dimethylaminoethoxy)benzoyl)-leucinyl)-amino-3N-(3-(2-pyridyl)phenylacetyl)-amino-propan-2-one;

1N-(N-(3-((2-dimethylamino)ethoxy)-4-methoxy-benzoyl)-leucinyl)-amino-3N-(3-(2-pyridyl)phenylacetyl)-amino-propan-2-one;

1N-(N-(1,2,3,4-tetrahydroisoquinoline-2-carbonyl)-leucinyl)-amino-3N-(3-(2-pyridyl)phenylacetyl)-amino-propan-2-one;

1N-(N-(piperazine-1-carbonyl)-leucinyl)-amino-3N-(3-(2-pyridyl)phenylacetyl)-amino-propan-2-one;

1N-(N-(4-methylpiperazine-1-carbonyl)-leucinyl)-amino-3N-(3-(2-pyridyl)phenylacetyl)-amino-propan-2-one; 1N-(N-(4-phenoxybenzenesulfonyl)-leucinyl)-amino-3N-(3-(2-pyridyl)phenylacetyl)-amino-propan-2-one;

1N-(N-(4-methoxy-3-(2-(4-morpholinyl)ethoxy)benzoyl)-leucinyl)-amino-3N-(3-(2-pyridyl)phenylacetyl)-amino-propan-2-one 1N-(N-(3-methoxy-2-naphthoyl)-amino-3N-(3-(2-pyridyl)phenylacetyl)-amino-propan-2-one;

1N-(N-(cyclohexene-1-carbonyl)-amino-3N-(3-(2-pyridyl)phenylacetyl)-amino-propan-2-one;

1N-(N-(4-(benzoyl)benzoyl)-leucinyl)-amino-3N-(3-(2-pyridyl)phenylacetyl)-amino-propan-2-one;

1N-(N-(4-(phenylmethoxy)benzoyl)-leucinyl)-amino-3N-(3-(2-pyridyl)phenylacetyl)-amino-propan-2-one;

1N-(N-(4-(4-cyanophenoxy)benzoyl)-leucinyl)-amino-3N-(3-(2-pyridyl)phenylacetyl)-amino-propan-2-one;

1N-(N-(9-oxo-9H-xanthene-2-carbonyl)-leucinyl)-amino-3N-(3-(2-pyridyl)phenylacetyl)-amino-propan-2-one;

1N-(N-(2-(pyrrol-1-yl)benzothiazole-6-carbonyl)-leucinyl)-amino-3N-(3-(2-pyridyl)phenylacetyl)-amino-propan-2-one;

1N-(N-(4-(phenylmethyl)benzoyl)-leucinyl)-amino-3N-(3-(2-pyridyl)phenylacetyl)-amino-propan-2-one; 1N-(N-(4-(4-nitrophenoxy)benzoyl)-leucinyl)-amino-3N-(3-(2-pyridyl)phenylacetyl)-amino-propan-2-one:

1N-(N-(4-(4-(trifluoromethyl)phenoxy)benzoyl)-leucinyl)-amino-3N-(3-(2-pyridyl)phenylacetyl)-amino-propan-2-one;

1N-(N-(benzoxazole-6-carbonyl)-leucinyl)-amino-3N-(3-(2-pyridyl)phenylacetyl)-amino-propan-2-one; 1N-(N-(benzoxazole-5-carbonyl)-leucinyl)-amino-3N-(3-(2-pyridyl)phenylacetyl)-amino-propan-2-one;

1N-[N-(3-(2-Pyridyl)-benzoyl)-L-leucinyl)amino-3N-[3-(phenyl)phenylacetyl]amino-2-propanone;

1N-(N-(2-Quinolinylcarbonyl)-L-leucinyl)amino-3N-[3-(phenyl)phenylacetyl]amino-2-propanone;

1N-(N-(3-Quinolinylcarbonyl)-L-leucinyl)amino-3N-[3-(phenyl)phenylacetyl]amino-2-propanone;

1N-(N-(6-Quinolinylcarbonyl)-L-leucinyl)amino-3N-[3-(phenyl)phenylacetyl]amino-2-propanone;

(S)-3N-[N-{4-Methoxy-3-(N,N-dimethylaminoethyl)oxy}benzoyl-L-leucinyl]amino-1N-[3-(3-(biphenyl)acetyl]amino-2-butanone;

(S)-3N-[N-{3-(4-Methylpiperazinyl)benzoyl}-L-leucinyl]amino-1N-[3-(biphenyl)acetyl)]amino-2-butanone;

1N-(N-(3,4-Dichlorobenzoyl)-leucinyl)-amino-3N-(2-pyridyl-sulfonyl)-amino-propan-2-one;, 1N-(N-(Benzofuran-2-carbonyl)-L-leucinyl)amino-3N-(2-pyridyl-sulfonyl)amino-2-propanone;

(S)-3N-[N-(4-Methoxy-3-(N,N-dimethylaminoethoxy)benzoyl)-L-leucinyl]amino-1N-[(2-pyridyl)sulfonyl]amino-2-butanone;

(S)-3N-(N-(Thianaphthenyl-2-carbonyl)-L-leucinyl)amino-1N-[(2-pyridyl)sulfonyl]amino-2-butanone;

(S)-3N-(N-(4-Trifluoromethylbenzoyl)-L-leucinyl]amino-1N-[(2-pyridyl)sulfonyl]amino-2-butanone;

1N-[N-(Benzofuran-2-carbonyl)-L-leucinyl)amino-3N-(2-pyridylsulfonyl)amino-2-propanone;

1N-(N-(3,4-cimethoxybenzoyl)-L-leucinyl)amino-3N-[2-(3-(2-pyridyl)phenyl)-propionyl]amino-2-propanone;

(S)-3N-(N-(2-thianaphthenylcarbonyl)-L-leucinyl)amino-1N-[2-(3-(2-pyridyl)phenyl)-propionyl]amino-2-butanone;

(S)-3N-(N-(benzofuranyl-2-carbonyl)-L-leucinyl)amino-1N-[2-(3-(2-pyridyl)phenyl)-propionyl]amino-2-butanone;

(S)-3N-(n-((Morpholinoethoxy)benzofuryl-2-carbonyl)-L-leucinyl)amino-1N-[2-(3-(2-pyridyl)phenyl)-propionyl]amino-2-butanone;

1N-(N-(5-(Morpholinoethyloxy)benzofuryl-2-carbonyl)-L-leucinyl)amino-3N-[2-(3-(2-pyridyl)phenyl)-propionyl]amino-2-propanone;

(S)-3N-[N-({4-Methoxy-3-(N,N-dimethylaminoethyl)oxy}benzoyl)-L-leucinyl)amino-1N-[2-(3-(2-pyridyl)phenyl)-propionyl]amino-2-butanone;

1N-(N—(Cbz)-L-leucinyl)amino-3N-[2-methyl-2-[3-(2-pyridyl)phenyl]propionyl]amino]-2-propanone;
1N-(N-(benzofuranyl-2-carbonyl)-L-leucinyl)amino-3N-[[3-(3-methyl)butyl]amino]-2-propanone;
1N-[N-(5-(Morpholinoethyoxy)benzofuran-2-yl)carbonyl)-L-leucinyl)-amino]-3N-[[3-(3-methyl)butyl-carbonyl]amino]-2-propanone;
(S)-3N-(n-(5-Carboxylbenzofuryl-2-carbonyl)-L-leucinyl)amino-1N-[3-(2-pyridyl)phenylacetyl]amino-2-butanone;
(+/-)-1,3-N,N-Bis[2-{3-(2-pyridyl)phenyl}-4-methylvaleryl]amino-2-propanone;
(R)-1N-[2-{3-(2-Pyridyl)phenyl}-4-methylvaleryl]amino-1-3N-[(2-pyridyl)sulfonyl]amino-2-butanone;
(+/-)-1N-[2-{3-(2-Pyridyl)phenyl}-4-methylvaleryl]amino-3N-[3-(3-methyl-2-pyridyl)phenylacetyl]amino-2-propanone;
(+/-)-1N-[2-{3-(2-Pyridyl)phenyl}-4-methylvaleryl]amino-3N-(4-fluorophenylsulfonyl)amino-2-propanone;
(+/-)-1N-[2-{3-(2-Pyridyl)phenyl}-4-methylvaleryl]amino-3N-(4-trifluoromethylbenzenesulfonyl)amino-2-propanone;
(+/-)-1N-[2-{3-(2-Benzofuryl)phenyl}-4-methylvaleryl]amino-3N-[3-(6-methyl-2-pyridyl)phenylacetyl]amino-2-propanone;
(+/-)-1N-[2-{3-(2-Methylphenyl)phenyl}-4-methylvaleryl]amino-3N-[(2-pyridyl)sulfonyl]amino-2-propanone;
(+/-)-1N-[2-{3-(1-Piperidinyl)phenyl}-4-methylvaleryl]amino-3N-[3-(6-methyl-2-pyridyl)phenylacetyl]amino-2-propanone;
(+/-)-1N-(N-(2-(3-biphenyl)-4-methyl-valeryl)-amino-3N-(3-(phenylsulfonyl)-amino-propan-2-one; (R)-1N-(N-(2-(3-biphenyl)-4-methyl-valeryl)-amino-3N-(3-(2-pyridyl)phenylacetyl)-amino-prnpan-2-one; (R)-1N-(N-(2-(3-biphenyl)-4-methyl-valeryl)-amino-3N-(3-(phenylsulfonyl)-amino-propan-2-one;
1N-(N-(2-naphthyl-carbonyl)-leucinyl)-amino-3N-(2-pyridyl-sulfonyl)-amino-propan-2-one;
1N-(N-(4-fluorobenzoyl)-leucinyl)-amino-3N-(2-pyridyl-sulfonyl)-amino-propan-2-one;
3N-(N-(8-quinoline-2-carbonyl)-L-leucinyl)-amino-1N-(4-methoxy-phenyl)-amino-butane-2-one;
3N-(N-(8-quinoline-2-carbonyl)-L-leucinyl)-amino-1N-(4-fluoro-phenyl)-amino-butane-2-one;
3N-(N-(8-quinoline-2-carbonyl)-L-leucinyl)-amino-1N-(4-carboxy methyl-phenyl)-1-amino-butane-2-one;
3N-(N-(8-quinoline-2-carbonyl)-L-leucinyl)-amino-1N-(4-carboxy-phenyl)-amino-butane-2-one;
3N-(N-(8-quinoline-2-carbonyl)-L-leucinyl)-amino-1N-(3,4-dimethoxy-phenyl)-amino-butane-2-one;
3N-(N-(8-quinoline-2-carbonyl)-L-leucinyl)-amino-1N-(2-pyridyl)-amino-butane-2-one;
1N-(N-(2-thianaphthenylcarbonyl)-L-phenylalaninyl)amino-3N-[3-(2-pyridyl)phenylacetyl]amino-2-butanone;
1N-(N-(3,4-dimethoxy-benzoyl)-L-phenylalaninyl)amino-3N-[3-(2-pyridyl)phenylacetyl]amino-2-butanone;
1N-(N-(8-quinoline-carbonyl)-L-phenylalaninyl)amino-3-[3-(2-pyridyl)phenylacetyl]amino-2-butanone;
1N-(N-(8-quinoline-carbonyl)-L-leucinyl)amino-3-[3-(2-pyridyl)phenylacetyl]amino-2-butanone;
1N-(N-(5-quinoline-carbonyl)-L-phenylalaninyl)amino-3-[3-(2-pyridyl)phenylacetyl]amino-2-butanone;
1N-(N-(5-quinoline-carbonyl)-L-phenylalaninyl)amino-3-[3-(2-pyridyl)phenylacetyl]amino-2-butanone;
1N-(N-(4-trifluoromethyl-benzoyl)-L-phenylalaninyl)amino-3-[3-(2-pyridyl)phenylacetyl]amino-2-butanone;
1N-[N-(5-(Morpholinoethyloxy)benzofuran-2-yl)carbonyl)-L-leucinyl)-amino]-3-[[4-fluoro-phenyl sulfonyl]amino]-2-propanone;
1N-[N-(5-(Morpholinoethyloxy)benzofuran-2-yl)carbonyl)-L-leucinyl-amino]-3-propionyl-amino]-2-propanone;
1N-[N-(5-(Morpholinoethyloxy)benzofuran-2-yl)carbonyl)-L-leucinyl-amino-3N-[[phenylsulfonyl]amino]-2-propanone;
1N-(N-(5-(Morpholinoethyloxy)benzofuran-2-yl)carbonyl)-L-leucinyl-amino-3N-[[acetyl]amino]-2-propanone;
1N-(N-(5-(Morpholinoethyloxy)benzofuran-2-yl)carbonyl)-L-leucinyl-amino-3N-[[3-butyl-carbonyl]amino]-2-propanone;
(S)-1N-(N-(5-(Morpholinoethyloxy)benzofuryl-2-carbonyl)-L-leucinyl-amino-3N-[3-(2-pyridyl)phenylacetyl]amino-2-butanone;
1N-[N-(5-(Morpholinoethyloxy)benzofuran-2-yl)carbonyl)-L-leucinyl-amino-3N-[[2-pyridyl-sulfonyl]amino]-2-propanone;
(S)-1N-[N-(benzofuran-2-yl-carbonyl)-L-leucinyl-amino-3N-[[2-pyridyl-sulfonyl]amino]-2-butanone;
1N-[N-(5 -(Morpholinoethyloxy)benzofuran-2-yl)carbonyl)-L-leucinyl)-amino]-3-[isopropylsulfonyl]amino]-2-propanone;
1N-(N-(pyrimidine-4-carbonyl)-leucinyl)-amino-3N-(3-(2-pyridyl)-phenylacetyl)-amino-propan-2-one;
1N-(N-(3-phenylpropionyl)-leucinyl)-amino-3N-(3-(2-pyridyl)phenylacetyl)-amino-propan-2-one;
(+/-)-1N-(N-(2-(3-biphenyl)-4-methyl-valeryl)-amino-3N-(3-(phenylsulfonyl)-amino-propan-2-one; and
(R)-1N-(N-(2-(3-biphenyl)-4-methyl-valeryl)-amino-3N-(3-(phenylsulfonyl)-amino-propan-2-one.

Compounds of Formula I selected from the following group are particularly preferred embodiments of the present invention:

(S)-3N-(N-(thianaphthenyl-2-carbonyl)-leucinyl)-amino-1N-(3-{2-(1-oxo)-pyridyl}phenylacetyl)-amino-butan-2-one;
(S)-3N-(N-(Benzyloxycarbonyl)-L-leucinyl)amino-1N-[3-{2-(1-oxo)-pyridyl}phenylacetyl]amino-2-butanone;
(S)-3N-[N-((5-Morpholinoethyloxy)benzofuryl-2-carbonyl)-L-leucinyl)]amino-1N-[3-(2-(1-oxo)pyridyl)phenylacetyl]amino-2-butanone;
1N-(N-(thiophene-2-carbonyl)-leucinyl)-amino-3N-(3-(2-pyridyl)-phenyl acetyl)-amino-propan-2-one; 1N-(N-(3,4-Dichlorobenzoyl)-L-leucinyl)amino-3N-[3-(2-pyridyl)phenylacetyl]amino-2-propanone;
1-(N-4-((7-nitro-2,1,3-benzooxadiazole)-L-pyrrolidinyl-)-N-(L-leucinyl))-amino-3N-[3-(2-pyridyl)phenylacetyl]amino-2-propanone;
1N-(N-(5-butylpyridine-2-carbonyl)-L-leucinyl)amino-3N-[3-(2-pyridyl)phenylacetyl]amino-2-propanone;
1N-[N-(5-(Morpholinoethyloxy)benzofuryl-2-carbonyl)-L-leucinyl]amino-3N-[3-(2-pyridyl)phenylacetyl]amino-2-propanone;

(S)-3N-(N-(Benzothiazolidyl-6carbonyl)-L-Leucinyl)amino-1N-[3-(2-pyridyl)phenylacetyl]amino2-butanone;

1N-(N-(Benzyloxy-carbonyl)-L-leucinyl)amino-3N-[3-(phenyl)phenylacetyl]amino-2-propanone;

(S)-3N-(N-(5-Methoxycarbonylbenzofuryl-2-carbonyl)-L-leucinyl)amino-1N-[3-(2-pyridyl)phenylacetyl]amino-2-butanone;

(S)-3N-[N-{4-Methoxy-3-(N,N-dimethylaminoethyl)oxy}benzoyl-L-leucinyl]amino-1N-[3-(2-pyridyl)phenylacetyl]amino-2-butanone;

(S)-3N-[N-(3-(4-Methylpiperazinyl))-benzoyl}-L-leucinyl]amino-1N-[3-(2-pyridyl)phenylacetyl]amino-2-propanone;

(S)-3N-[N-{(N-Methyl-N'-(4-(1-methylpiperidinyl)amino}benzoyl}-L-leucinyl]amino-1N-[3-(2-pyridyl)phenylacetyl]amino-2-butanone;

(S)-3N-[N-{(N-Methyl-N'-(beta-N,N-dimethylaminoethyl)amino}benzoyl-L-leucinyl]amino-1N-[3-(2-pyridyl)phenylacetyl]amino-2-butanone;

(S)-3N-[N-(5-(Morpholinoethyloxy)benzofuryl-2-carbonyl)-L-leucinyl]amino-1N-[3-(2-pyridyl)phenylacetyl]amino-2-butanone;

(S)-3N-{N-(4-Methyl[4-trifluoromethyl)phenyl]thiazole-5-carbonyl)-L-leucinyl)]}-amino-1N-[3-(2-pyridyl)phenylacetyl]amino-2-butanone;

1N-(N-(biphenyl)-4-carbonyl)-leucinyl)-amino-3N-(3-(2-pyridyl)-phenylacetyl)-amino-propan-2-one; 1N-(N-(indole-2-carbonyl)-leucinyl)-amino-3N-(3-(2-pyridyl)-phenylacetyl)-amino-propan-2-one;

1N-(N-(indole-6-carbonyl)-leucinyl)-amino-3N-(3-2-pyridyl)-phenylacetyl)-amino-propan-2-one;

1N-(N-(adamantane-1-carbonyl)-leucinyl)-amino-3N-(3-(2-pyridyl)-phenylacetyl)-amino-propan-2-one;

1N-(N-(1-methoxy-2-naphthoyl)-leucinyl)-amino-3N-(3-(2-pyridyl)-phenylacetyl)-amino-propan-2-one;

1N-(N-(benzoyl)-leucinyl)-amino-3N-(3-(2-pyridyl)-phenylacetyl)-amino-propan-2-one;

1N-(N-(thieno[3,2-b]thiophene-2-carbonyl)-leucinyl)-amino-3N-(3-(2-pyridyl)-phenylacetyl)-amino-propan-2-one;

1N-(N-(4-cyclohexylbenzoyl)-leucinyl)-amino-3N-(3-(2-pyridyl)-phenylacetyl)-amino-propan-2-one;

1N-(N-(1-methylpyrrole-2-carbonyl)-leucinyl)-amino-3N-(3-(2-pyridyl)-phenylacetyl)-amino-propan-2-one;

1N-(N-(4-methoxybenzoyl)-leucinyl)-amino-3N-(3-(2-pyridyl)-phenylacetyl)-amino-propan-2-one;

1N-(N-(thiophene-3-carbonyl)-leucinyl)-amino-3N-(3-(2-pyridyl)-phenylacetyl)-amino-propan-2-one;

1N-(N-(4-(4'-ethylbiphenyl)carbonyl)-leucinyl)-amino-3N-(3-(2-pyridyl)-phenylacetyl)-amino-propan-2-one;

1N-(N-(pyrazine-2-carbonyl)-leucinyl)-amino-3N-(3-(2-pyridyl)-phenylacetyl)-amino-propan-2-one;

1N-(N-(pyrimidine-4-carbonyl)-leucinyl)-amino-3N-(3-(2-pyridyl)-phenylacetyl)-amino-propan-2-one; 1N-(N-(2,7-dimethylpyrazolo[1,5-a]pyrimidine-6-carbonyl)-leucinyl)-amino-3N-(3-(2-pyridyl)-phenylacetyl)-amino-propan-2-one;

1N-(N-(4,7-dimethylpyrazolo[5,1-c][1,2,4]triazine-3-carbonyl)-leucinyl)-amino-3N-(3-(2-pyridyl)-phenylacetyl)-amino-propan-2-one;

1N-(N-thianaphthenyl-2-carbonyl)-leucinyl)-amino-3N-(3-(6-methyl-2-pyridyl)-phenylacetyl)-amino-propan-2-one;

1N-(N-thianaphthenyl-2-carbonyl)-leucinyl)-amino-3N-(3-(5-methyl-2-pyridyl)-phenylacetyl)-amino-propan-2-one; 1N-(N-(4-trifluoromethylbenzoyl)-leucinyl)-amino-3N-(3-(6-methyl-2-pyridyl)-phenylacetyl)-amino-propan-2-one;

1N-(N-(4-trifluoromethylbenzoyl)-leucinyl)-amino-3N-(3-(4-methyl-2-pyridyl)-phenylacetyl)-amino-propan-2-one;

1N-(N-tert-butoxycarbonyl-leucinyl)-amino-3N-(4-nitrophenylmethoxycarbonyl)-amino-propan-2-one;

1N-(N-(4-((2-dimethylamino)ethoxy)-benzoyl)-leucinyl)-amino-3N-(3-(2-pyridyl)phenylacetyl)-amino-propan-2-one; 1N-(N-(4-((2-dimethylamino)ethoxy)-3-methoxy-benzoyl)-leucinyl)-amino-3N-(3-(2-pyridyl)phenylacetyl)-amino-propan-2-one;

1N-(N-(3-(dimethylaminoethoxy)benzoyl)-leucinyl)-amino-3N-(3-(2-pyridyl)phenylacetyl)-amino-propan-2-one;

1N-(N-(3-((2-dimethylamino)ethoxy)-4-methoxy-benzoyl)-leucinyl)-amino-3N-(3-(2-pyridyl)phenylacetyl)-amino-propan-2-one;

1N-(N-(3-((2-(pipendinyl)ethoxy)-4-methoxy-benzoyl)-leucinyl)-amino-3N-(3-(2-pyridyl)phenylacetyl)-amino-propan-2-one;

1N-(N-(3-phenylpropionyl)-leucinyl)-amino-3N-(3-(2-pyridyl)phenylacetyl)-amino-propan-2-one; 1N-(N-(1,2,3,4-tetrahydroisoquinoline-2-carbonyl)-leucinyl)-amino-3N-(3-(2-pyridyl)phenylacetyl)-amino-propan-2-one;

1N-(N-(piperazine-1-carbonyl)-leucinyl)-amino-3N-(3-(2-pyridyl)phenylacetyl)-amino-propan-2-one;

1N-(N-(4-methylpiperazine-1-carbonyl)-leucinyl)-amino-3N-(3-(2-pyridyl)phenylacetyl)-amino-propan-2-one; 1N-(N-((2-pyridyl)methoxycarbonyl)-leucinyl)-amino-3N-(3-(2-pyridyl)phenylacetyl)-amino-propan-2-one;

1N-(N-(4-phenoxybenzenesulfonyl)-leucinyl)-amino-3N-(3-(2-pyridyl)phenylacetyl)-amino-propan-2-one;

1N-(N-(4-methoxy-3(2-(4-morpholinyl)ethoxy)benzoyl)-leucinyl)-amino-3N-(3-(2-pyridyl)phenylacetyl)-amino-propan-2-one;

1N-(N-(3-methoxy-2-naphthoyl)-amino-3N-(3-(2-pyridyl)phenylacetyl)-amino-propan-2-one;

1N-(N-(cyclohexene-1-carbonyl)-amino-3N-(3-(2-pyridyl)phenylacetyl)-amino-propan-2-one;

1N-(N-(4-(benzoyl)benzoyl)-leucinyl)-amino-3N-(3-(2-pyridyl)phenylacetyl)-amino-propan-2-one;

1N-(N-(4-(phenylmethoxy)benzoyl)-leucinyl)-amino-3N-(3-(2-pyridyl)phenylacetyl)-amino-propan-2-one;

1N-(N-(4-(4-cyanophenoxy)benzoyl)-leucinyl)-amino-3N-(3-(2-pyridyl)phenylacetyl)-amino-propan-2-one;

1N-(N-(9-oxo-9H-xanthene-2-carbonyl)-leucinyl)-amino-3N-(3-(2-pyridyl)phenylacetyl)-amino-propan-2-one;

1N-(N-(2-(pyrrol-1-yl)benzothiazole-6-carbonyl)-leucinyl)-amino-3N-(3-(2-pyridyl)phenylacetyl)-amino-propan-2-one;

1N-(N-(4-(phenylmethyl)benzoyl)-leucinyl)-amino-3N-(3-(2-pyridyl)phenylacetyl)-amino-propan-2-one; 1N-(N-(4-(4-nitrophenoxy)benzoyl)-leucinyl)-amino-3N-(3-(2-pyridyl)phenylacetyl)-amino-propan-2-one;

1N-(N-(4-(4-(trifluoromethyl)phenoxy)benzoyl)-leucinyl)-amino-3N-(3-(2-pyridyl)phenylacetyl)-amino-propan-2-one;

1N-(N-(benzoxazole-6-carbonyl)-leucinyl)-amino-3N-(3-(2-pyridyl)phenylacetyl)-amino-propan-2-one;
1N(N-(benzoxazole-5-carbonyl)-leucinyl)-amino-3N-(3-(2-pyridyl)phenylacetyl)-amino-propan-2-one;
1N-[N-(3(2-Pyridyl)-benzoyl)-L-leucinyl)amino-3N-[3-(phenyl)phenylacetyl]amino-2-propanone;
1N-(N-(2-Quinolinylcarbonyl)-L-leucinyl)amino-3N-[3-(phenyl)phenylacetyl]amino-2-propanone;
1N-(N-(3-Quinolinylcarbonyl)-L-leucinyl)amino-3N-[3-(phenyl)phenylacetyl]amino-2-propanone;
1N-(N-(6-Quinolinylcarbonyl)-L-leucinyl)amino-3N-[3-(phenyl)phenylacetyl]amino-2-propanone;
(S)-3N-[N-{4-Methoxy-3-(N,N-dimethylaminoethyl)oxy}benzoyl-L-leucinyl]amino-1N-[3-(3-(biphenyl)acetyl]amino-2-butanone;
(S)-3N-[N-{3-(4-Methylpiperazinyl)benzoyl}-L-leucinyl]amino-1N-[3-(biphenyl)acetyl)]amino-2-butanone;
1N-(N-(3,4-Dichlorobenzoyl)-leucinyl)-amino-3N-(2-pyridyl-sulfonyl)-amino-propan-2-one;
1N-(N-(Benzofuran-2-carbonyl)-L-leucinyl)amino-3N-(2-pyridylsulfonyl)amino-2-propanone;
(S)-3N-[N-(4-Methoxy-3-(N,N-dimethylaminoethoxy)benzoyl)-L-leucinyl]amino-1N-[(2-pyridyl)sulfonyl]amino-2-butanone;
(S)-3N-(N-(Thianaphthenyl-2-carbonyl)-L-leucinyl)amino-1N-[(2-pyridyl)sulfonyl]amino-2-butanone;
(S)-3N-[N-(4-Trifluoromethylbenzoyl)-L-leucinyl]amino-1N-[(2-pyridyl)sulfonyl]amino-2-butanone;
1N-(N-(Benzofuran-2-carbonyl)-L-leucinyl)amino-3N-(2-pyridylsulfonyl)amino-2-propanone;
1N-(N-(3,4-cimethoxybenzoyl)-leucinyl)amino-3N-[2-(3-(2-pyridyl)phenyl)-propionyl]amino-2-propanone;
(S)-3N-(N-(2-thianaphthenylcarbonyl)-L-leucinyl)amino-1N-[2-(3-(2-pyridyl)phenyl)-propionyl]amino-2-butanone;
(S)-3N-(N-(benzofuranyl-2-carbonyl)-L-leucinyl)amino-1N-[2-(3-(2-pyridyl)phenyl)-propionyl]amino-2-butanone;
(S)-3N-(n-((Morpholinoethoxy)benzofuryl-2-carbonyl)-L-leucinyl)amino-1N-[2-(3-(2-pyridyl)phenyl)-propionyl]amino-2-butanone;
1N-(N-(5-(Morpholinoethyloxy)benzofuryl-2-carbonyl)-L-leucinyl)amino-3N-[2-(3-(2-pyridyl)phenyl)-propionyl]amino-2-propanone;
(S)-3N-[N-({4-Methoxy-3-(N,N-dimethylaminoethyl)oxy}benzoyl)-L-leucinyl)amino-1N-[2-(3-(2-pyridyl)phenyl)-propionyl]amino-2-butanone;
1N-(N—(Cbz)-L-leucinyl)amino-3N-[2-methyl-2-[3-(2-pyridyl)phenyl]propionyl]amino]-2-propanone;
1N-(N-(benzofuranyl-2-carbonyl)-L-leucinyl)amino-3N-[[3-(3-methyl)butyl]amino]-2-propanone;
1N-[N-(5-(Morpholinoethyloxy)benzofuran-2-yl)carbonyl)-L-leucinyl)-amino]-3N-[[3-(3-methyl)butyl-carbonyl]amino]-2-propanone;
(S)-3N-(n-(5-Carboxylbenzofuryl-2-carbonyl)-L-leucinyl)amino-1N-[3-(2-pyridyl)phenylacetyl]amino-2-butanone;
(+/−)-1N-[2-{3-(2-Pyridyl)phenyl}-4-methylvaleryl]amino-3N-(4-fluorophenylsulfonyl)amino-2-propanone;
(+/−)-1N-(N-(2-(3-biphenyl)-4-methyl-valeryl)-amino-3N-(phenylsulfonyl)-amino-propan-2-one; (R)-1N-(N-(2-(3-biphenyl)-4-methyl-valeryl)-amino-3N-(3-(2-pyridyl)phenylacetyl)-amino-propan-2-one; (R)-1N-(N-(2-(3-biphenyl)-4-methyl-valeryl)-amino-3N-(3-(phenylsulfonyl)-amino-propan-2-one;
1N-(N-(2-naphthyl-carbonyl)-leucinyl)-amino-3N-(2-pyridyl-sulfonyl)-amino-propan-2-one;
1N-(N-(4-fluorobenzoyl)-leucinyl)-amino-3N-(2-pyridyl-sulfonyl)-amino-propan-2-one;
3N-(N-(8-quinoline-2-carbonyl)-L-leucinyl)-amino-1N-(4-methoxy-phenyl)-amino-butane-2-one;
3N-(N-(8-quinoline-2-carbonyl)-L-leucinyl)-amino-1N-(4-fluoro-phenyl)-amino-butane-2-one;
3N-(N-(8-quinoline-2-carbonyl)-L-leucinyl)-amino-1N-(4-carboxy methyl-phenyl)-1-amino-butane-2-one;
3N-(N-(8-quinoline-2-carbonyl)-L-leucinyl)-amino-1N-(4-carboxy-phenyl)-amino-butane-2-one;
3N-(N-(8-quinoline-2-carbonyl)-L-leucinyl)-amino-1N-(3,4-dimethoxy-phenyl)-amino-butane-2-one;
3N-(N-(8-quinoline-2-carbonyl)-L-leucinyl)-amino-1N-(2-pyridyl)-amino-butane-2-one;
1N-(N-(2-thianaphthenylcarbonyl)-L-phenylalaninyl)amino-3N-[3-(2-pyridyl)phenylacetyl]amino-2-butanone;
1N-(N-(3,4-dimethoxy-benzoyl)-L-phenylalaninyl)amino-3N-[3-(2-pyridyl)phenylacetyl]amino-2-butanone;
1N-(N-(8-quinoline-carbonyl)-L-phenylalaninyl)amino-3-[3-(2-pyridyl)phenylacetyl]amino-2-butanone;
1N-(N-(8-quinoline-carbonyl)-L-leucinyl)amino-3-[3-(2-pyridyl)phenylacetyl]amino-2-butanone;
1N-(N-(5-quinoline-carbonyl)-L-phenylalaninyl)amino-3-[3-(2-pyridyl)phenylacetyl]amino-2-butanone;
1N-(N-(5-quinoline-carbonyl)-L-phenylalaninyl)amino-3-[3-(2-pyridyl)phenylacetyl]amino-2-butanone;
1N-(N-(4-trifluoromethyl-benzoyl)-L-phenylalaninyl)amino-3-[3-(2-pyridyl)phenylacetyl]amino-2-butanone;
1N-[N-(5-(Morpholinoethyloxy)benzofuran-2-yl)carbonyl)-L-leucinyl)-amino]-3-[[4-fluorophenyl sulfonyl]amino]-2-propanone;
1N-[N-(5-(Morpholinoethyloxy)benzofuran-2-yl)carbonyl)-L-leucinyl-amino]-3-propionyl-amino]-2-propanone;
1N-[N-(5-(Morpholinoethyloxy)benzofuran-2-yl)carbonyl)-L-leucinyl-amino-3N-[phenylsulfonyl]amino]-2-propanone;
1N-[N-(5-(Morpholinoethyloxy)benzofuran-2-yl)carbonyl)-L-leucinyl-amino-3N-[[acetyl]amino]-2-propanone;
1N-[N-(5-(Morpholinoethyloxy)benzofuran-2-yl)carbonyl)-L-leucinyl-amino-3N-[[3-butyl-carbonyl]amino]-2-propanone;
1N-[N-(5-(Morpholinoethyloxybenzofuran-2-yl)carbonyl)-L-leucinyl-amino-3N-[2-pyridyl-sulfonyl]amino]-2-propanone;
(S)-1N-[N-(benzofuran-2-yl-carbonyl)-L-leucinyl-amino-3N-[[2-pyridyl-sulfonyl]amino]-2-butanone; and
1N-[N-(5-(Morpholinoethyloxy)benzofuran-2-yl)carbonyl)-L-leucinyl)-amino]-3-[isopropylsulfonyl)aminol]-2-propanone.

Definitions

The present invention includes all hydrates, solvates, complexes and prodrugs of the compounds of this invention.

Prodrugs are any covalently bonded compounds which release the active parent drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984).

The term "amino acid" as used herein refers to the D- or L- isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"$C_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof.

Here and throughout this application the term $C_0$ denotes the absence of the substituent group immediately following; for instance, in the moiety $ArC_{0-6}$alkyl, when C is 0, the substituent is Ar, e.g., phenyl. Conversely, when the moiety $ArC_{0-6}$alkyl is identified as a specific aromatic group, e.g., phenyl, it is understood that C is 0.

Certain radical groups are abbreviated herein. t-Bu refers to the tertiary butyl radical. Boc refers to the t-butyloxycarbonyl radical, Fmoc refers to the fluorenylmethoxycarbonyl radical, Ph refers to the phenyl radical, Cbz refers to the benzyloxycarbonyl radical.

Certain reagents are abbreviated herein. EDC and EDCI refer to 1-ethyl-3-(3-dimethylaminopropyl)-carbodiimide hydrochloride. LDA refers to lithium diisopropyl amide. HBTU refers to O-benzotriazole-N,N,N',N'-tetramethyluronium-hexafluorophosphate. HOBT refers to 1-hydroxybenzotriazole, DMF refers to dimethyl formamide, NMM is N-methylmorpholine, TFA refers to trifluoroacetic acid, THF refers to tetrahydrofuran. Jones reagent is a solution of chromium trioxide, water, and sulfuric acid well-known in the art.

Methods of Preparation

The compounds of the present invention may be conveniently prepared by the methods set forth in Schemes 1–6 below.

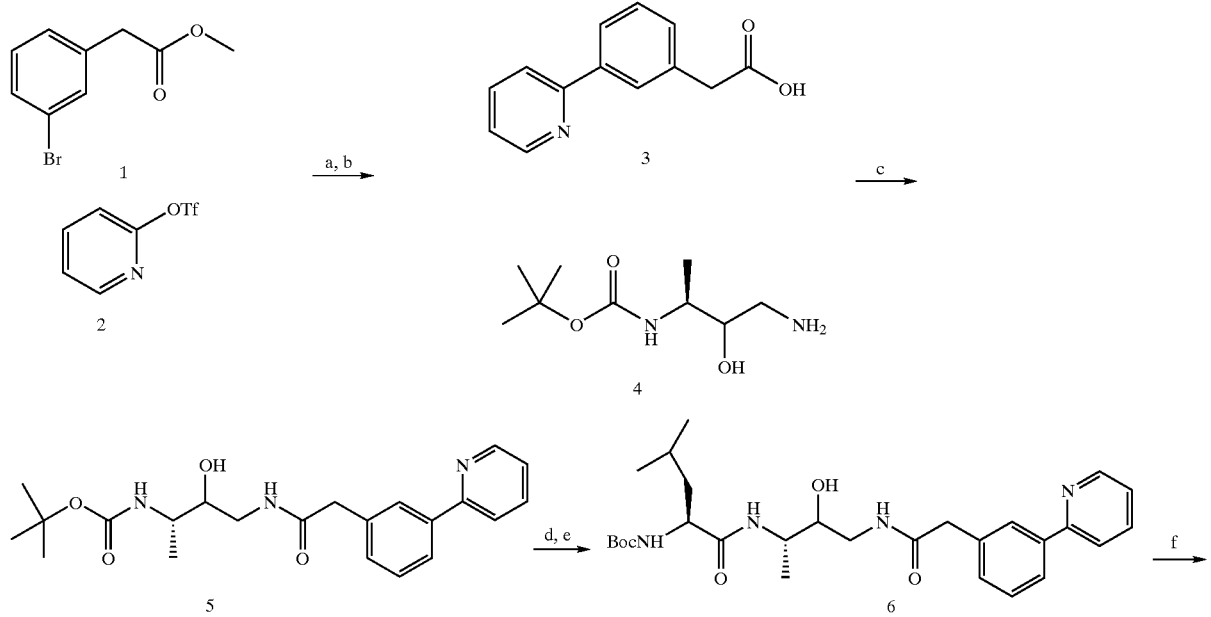

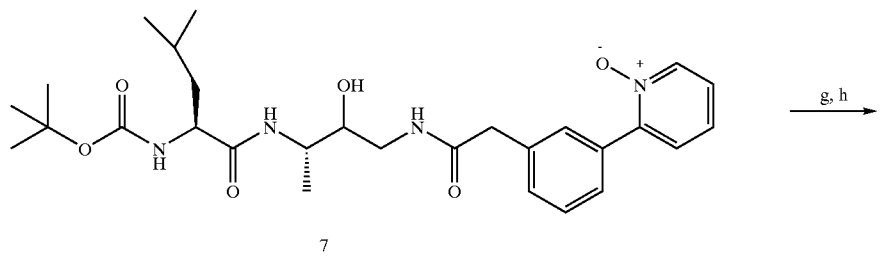

7

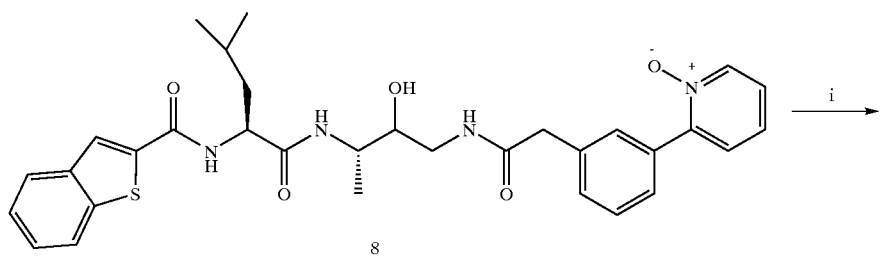

8

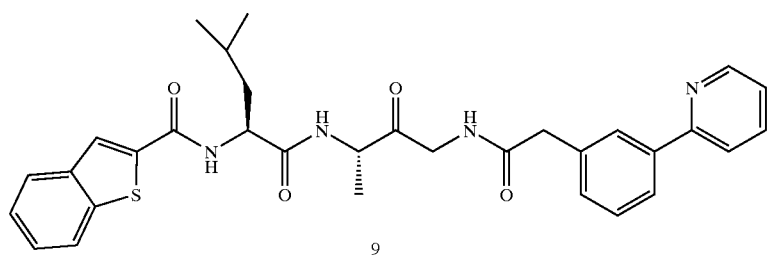

9 a) Pd(PPh$_3$)$_4$, Me$_3$SnSnMe$_3$, LiCl, dioxane, reflux, 16 h; b) lithium hydroxide. THF, water; c) HBTU, NMM, DMF d) 4M HCl/dioxane; e) Boc-LeuOH, HBTU, NMM, DMF; f) mCPBA, CH$_2$Cl$_2$; g) 4M HCl/dioxane; h) thianaphthenyl-2-carboxylic acid, HBTU, NMM, DMF; i) Dess-Martin periodinane, CH$_2$Cl$_2$ Palladium catalyzed cross-coupling of 3-bromophenyl acetic acid methyl ester (1-Scheme 1) and trimethyl stannyl pyridine (2-Scheme 1) provided the 3-(2-pyridyl)-phenyl acetic acid methyl ester, which was then saponified to the corresponding carboxylic acid (3-Scheme 1). Coupling of the acid with amine (4-Scheme 1) (cf. J. Med. Chem. 1989, 32, 165–170) with a coupling reagent such as HBTU/NMM or EDCI or DIC provided alcohol (5-Scheme 1). Removal of the Boc protecting group can be accomplished by using acidic conditions such as 4M HCl/dioxane or TFA. Coupling of the amine with Boc-L-leucine can be accomplished, again, using a variety of coupling reagents such as as HBTU/NMM or EDCI or DIC to provide alcohol (6-Scheme 1). Oxidation of the pyridine to the corresponding N-oxide (7-Scheme 1) can be accomplished with an oxidant such as mCPBA. Deprotection, again, can be accomplished by using acidic conditions such as 4M HCl/dioxane or TFA. Coupling of the amine with a carboxylic acid such as thianaphthenyl-2-carboxylic acid can be accomplished, again, using a variety of coupling reagents such as as HBTU/NMM or EDCI or DIC to provide alcohol (8-Scheme 1). Finally, oxidation of the alcohol to ketone (9-Scheme 1) can be accomplished with a variety of oxidants such as Dess-Martin periodinane (J. Org. Chem. 1983, 48, 4155–4156) or Swern conditions or Jones conditions, etc.

Also, by changing the order of the addition of the the 3-(2-pyridyl)-phenyl acetic acid and the Boc-L-leucine, analogs in which the methyl group at the alpha position of the ketone is moved to the alpha prime position can be prepared.

Scheme 2

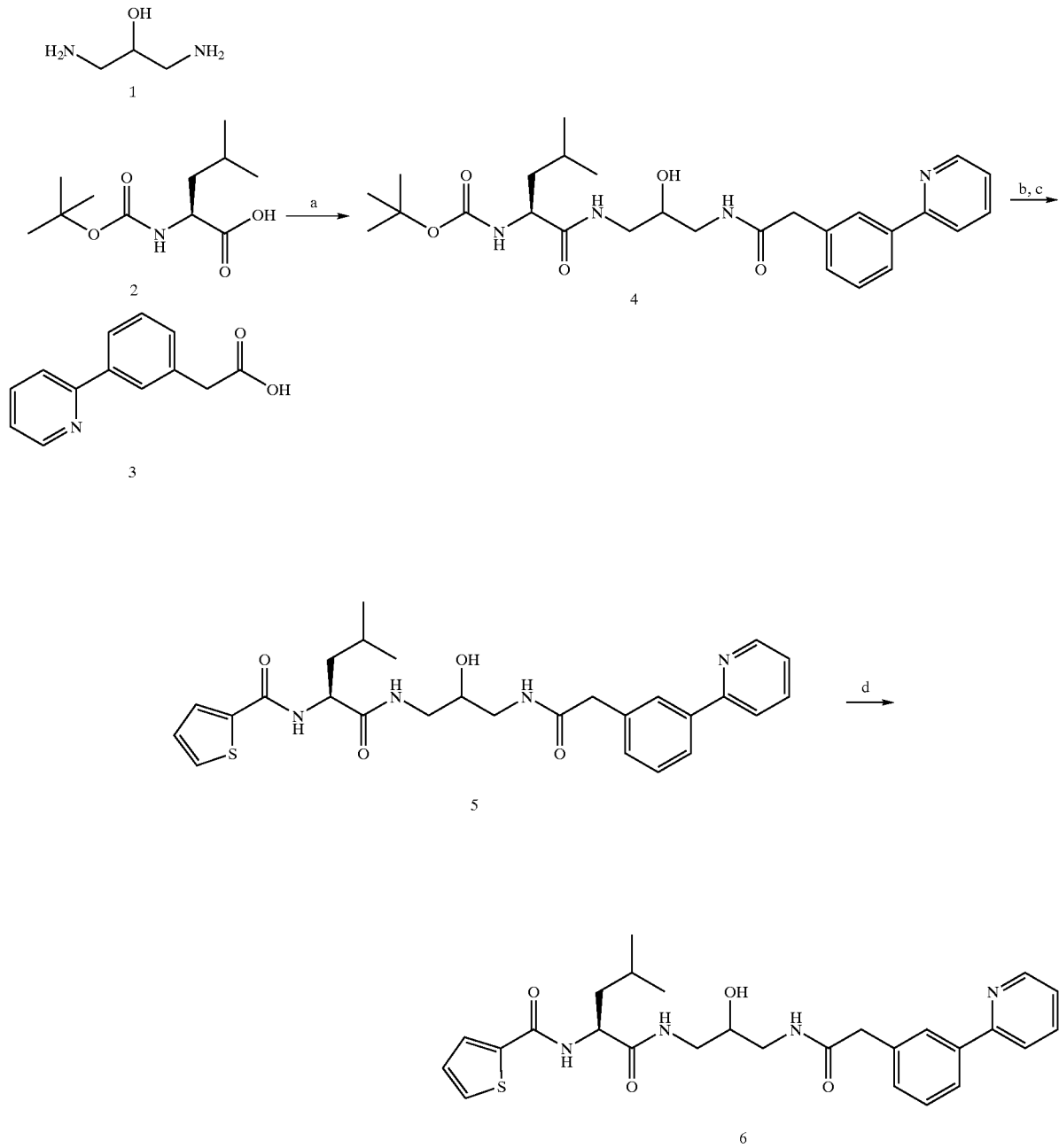

a) EDCI, HOBT-H$_2$O, DMF; b) 1.5:1 TFA; CH$_2$Cl$_2$; c) 2-thiophene carboxylic acid, EDCI, HOBT-H$_2$O, DMF; d) Dess-Martin periodinane. CH$_2$Cl$_2$ Coupling of 1,3-diaminopropanol (1-Scheme 2), Boc-L-leucine (2-Scheme 2), and 3-(2-pyridyl)-phenyl acetic acid was accomplished with a coupling reagent such as HBTU/NMM or EDCI or DIC providing alcohol (4-Scheme 2). Removal of the Boc protecting group can be accomplished by using acidic conditions such as 4M HCl/dioxane or TFA. Coupling of the amine with thiophene carboxylic acid can be accomplished, again, using a variety of coupling reagents such as HBTU/NMM or EDCI or DIC to provide alcohol (5-Scheme 2). Finally, oxidation of the alcohol to ketone (6-Scheme 2) can be accomplished with a variety of oxidants such as Dess-Martin periodinane or Swern conditions or Jones conditions, etc.

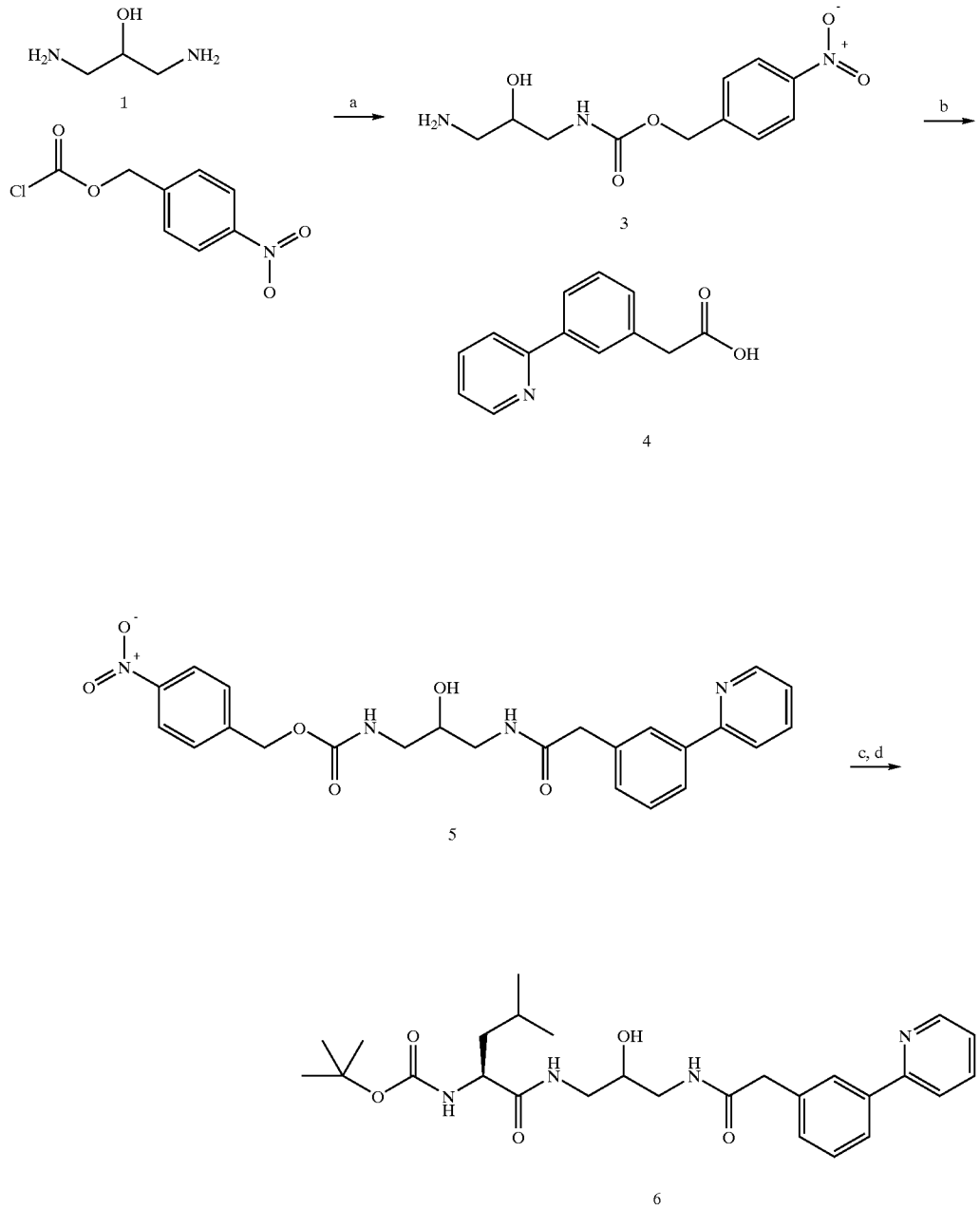

Scheme 3 a) CH$_2$Cl$_2$; b) EDCI, HOBT-H$_2$O, DMF; c) 10% Pd/C, H2; d) Boc-L-leucine, EDCI, HOBT-H$_2$O, DMF Coupling of 1,3-diaminopropanol (1-Scheme 3), p-nitro-benzyl chloroformate (2-Scheme 3), gave amino alcohol (3-Scheme 3). Coupling of amine (3-Scheme 3) with 3-(2-pyridyl)-phenyl acetic acid (4-Scheme 3) was accomplished with a coupling reagent such as HBTU/NMM or EDCI or DIC providing alcohol (4-Scheme 3). Removal of the p-nitro-benzyl carbamate protecting group can be accomplished by using conditions of hydrogenolysis such as Pd/C and 1 atmosphere of hydrogen gas. Coupling of the amine Boc-L-leucine provided the same intermediate as described in Scheme 2, compound (4)

Scheme 4

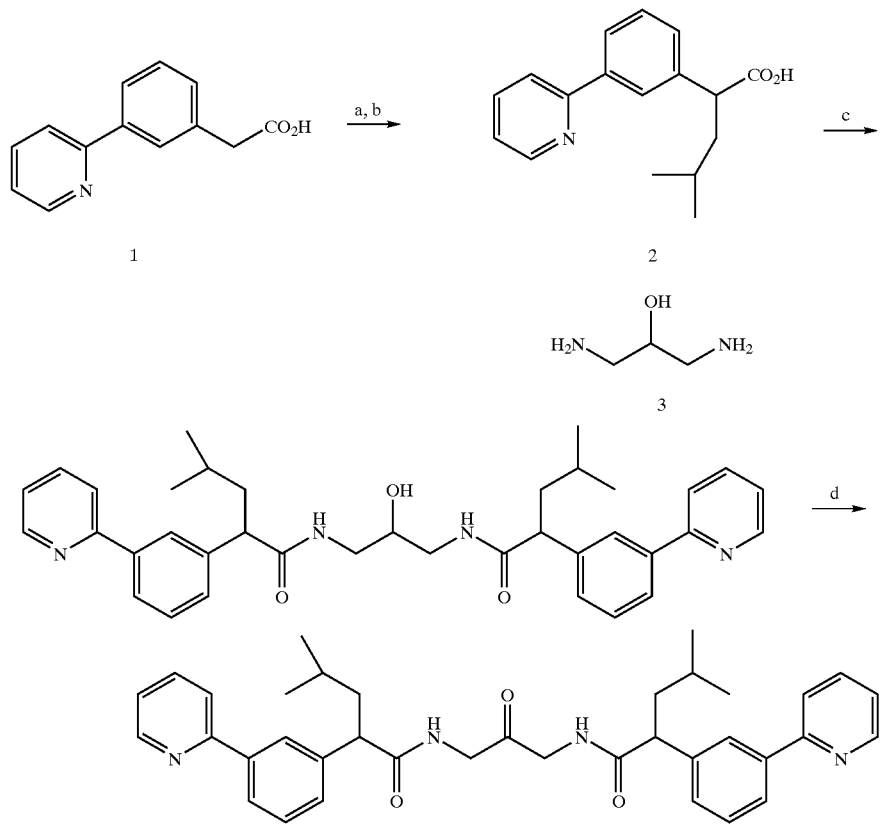

a) LDA, 3-bromo-2-methylpropene, THF; b) Pd/C, $H_2$; c) EDCI, HOBT-$H_2O$, DMF; d) Dess-Martin periodinane, $CH_2Cl_2$ Alkylation of 3-(2-pyridyl)-phenyl acetic acid (1-Scheme 4) by deprotonation with lithium diisopropyl amide and treatment with an alkylating agent such as 3-bromo-2-methylpropene gave the alpha alkylated intermediate, which was in turn reduced by hydrogenation to give carboxylic acid (2-Scheme 4). Coupling of 1,3-diaminopropanol (3-Scheme 4) with a coupling agent such as EDCI or HBTU or DIC or EDCI provided alcohol (4-Scheme 4). Finally, oxidation of the alcohol to ketone (5-Scheme 4) can be accomplished with a variety of oxidants such as Dess-Martin periodinane or Swern conditions or Jones conditions, etc.

Scheme 5

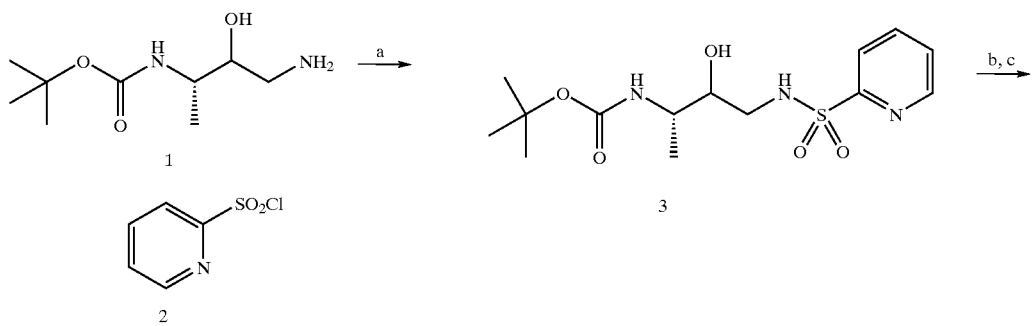

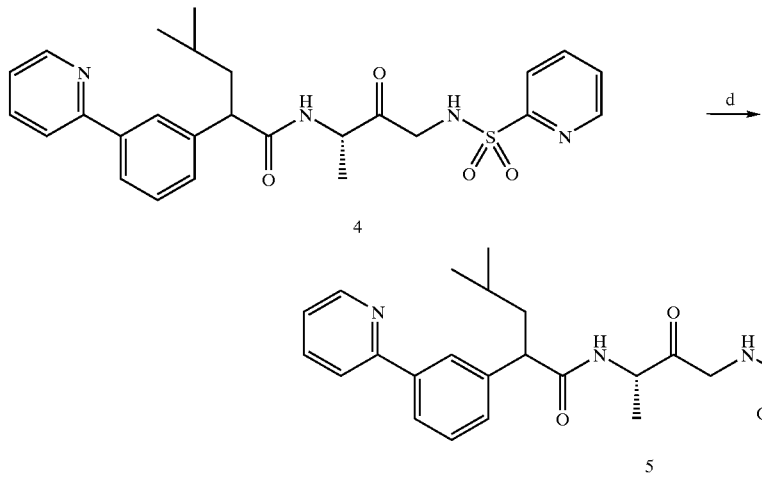

a) NMM, DMF; b) 3-(2-pyridyl)phenyl)-4-methyl valeric acid, EDCI, HOBT-H₂O, DMF; d) Dess-Martin periodinane, CH₂Cl₂

Coupling of amine (1-Scheme 5) and 2-pyridine sulfonyl chloride (2-Scheme 5) (gave alcohol (3-Scheme 5). Removal of the Boc protecting group can be accomplished by using acidic conditions such as 4M HCl/dioxane or TFA. Coupling of the amine with 3-(2-pyridyl)phenyl)-4-methyl valeric acid (or Boc-L-leucine, followed by deprotection and coupling to a different carboxylic acid as shown in Scheme 1 can be accomplished using a variety of coupling reagents such as as HBTU/NMM or EDCI or DIC to provide alcohol (6-Scheme 1). Finally, oxidation of the alcohol to ketone (9-Scheme 1) can be accomplished with a variety of oxidants such as Dess-Martin periodinane or Swern conditions or Jones conditions, etc.

a) EDCI, HOBT-H₂O, DMF; b) LiOH, THF, water; c) ClCO₂isobutyl, Et₃N, THF; CH₂N₂, Et₂O; d) HBr, acetic acid e) 4-methoxy-antiine, DMF.

Coupling of amine (9-Scheme 6) and carboxylic acid (1-Scheme 6) gave and amide which was then hydrolyzed to carboxylic acid (3-Scheme 6). Conversion of (3-Scheme 6) to a mixed anhydride with isobutyl chioro fomate, followed by treatment with diazomethane gave an intermediate diazo ketone which was then converted to the alpha bromo ketone (4-Scheme 6). S$_N$2 displacement of the bromide with p-methoxy-aniline gave ketone (5-Scheme 6).

Referring lo the methods of preparing the compounds of Formula I set forth in Schemes 1–6 above, the skilled artisan will appreciate that the present invention includes all novel intermediates required to make the compounds of Formula I.

Scheme 6

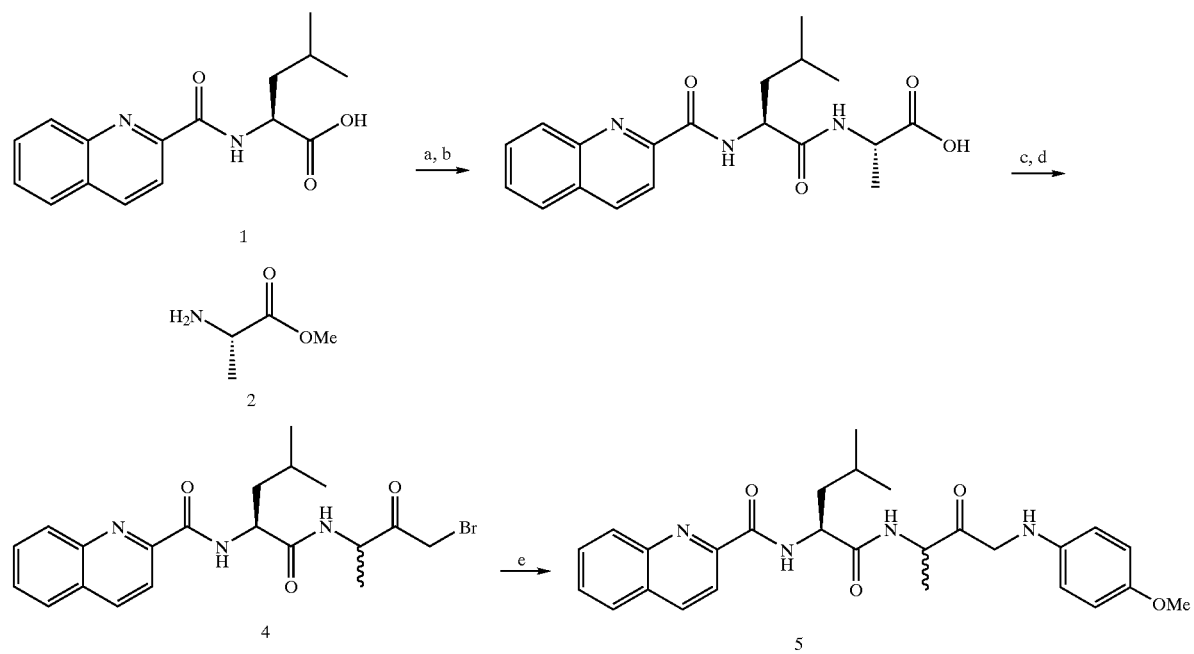

The starting materials used herein are commercially available amino acids or are prepared by routine methods well known to those of ordinary skill in the art and can be found in standard reference books, such as the COMPENDIUM OF ORGANIC SYNTHETIC METHODS. Vol. I–VI (published by Wiley-lnterscience).

Coupling methods to form amide bonds herein are generally well known to the art. The methods of peptide synthesis generally set forth by Bodansky et al., THE PRACTICE OF PEPTIDE SYNTHESIS, Springer-Verlag, Berlin, 1984; E. Gross and J. Meienhofer, THE PEPTIDES, Vol. 1, 1–284 (1979), and J. M. Stewart and J. D. Young, SOLID PHASE PEPTIDE SYNTHESIS, 2d Ed., Pierce Chemical Co., Rockford, Ill., 1984, are generally illustrative of the technique and are incorporated herein by reference.

Synthetic methods to prepare the compounds of this invention frequently employ protective groups to mask a reactive functionality or minimize unwanted side reactions. Such protective groups are described generally in Green, T. W, PROTECTIVE GROUPS IN ORGANIC SYNTHESIS. John Wiley & Sons, New York (1981). The term "amino protecting groups" generally refers to the Boc, acetyl, benzoyl, Fmoc and Cbz groups and derivatives thereof as known to the art. Methods for protection and deprotection, and replacement of an amino protecting group with another moiety are well known.

Acid addition salts of the compounds of Formula I are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts. Halides, sulfate, phosphate, alkanoates (such as acetate and trifluoroacetate), benzoates, and sulfonates (such as mesylate) are examples of anions present in pharmaceutically acceptable salts.

This invention also provides a pharmaceutical composition which comprises a compound according to Formula I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

Utility of the Present Invention

The compounds of Formula I are useful as protease inhibitors, particularly as inhibitors of cysteine and serine proteases, more particularly as inhibitors of cysteine proteases, even more particularly as inhibitors of cysteine proteases of the papain superfamily, yet more particularly as inhibitors of cysteine proteases of the cathepsin family, most particularly as inhibitors of cathepsin K. The present invention also provides useful compositions and formulations of said compounds, including pharmaceutical compositions and formulations of said compounds.

The present compounds are useful for treating diseases in which cysteine proteases are implicated, including infections by pneumocystis carinii, trypsanoma cruzi, trypsanoma brucei, and Crithidia fusiculata; as well as in schistosomiasis, malaria, tumor metastasis, metachromatic leukodystrophy, muscular dystrophy, amytrophy; and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease; hypercalcemia of malignancy, and metabolic bone disease.

Metastatic neoplastic cells also typically express high levels of proteolytic enzymes that degrade the surrounding matrix, and certain tumors and metastatic neoplasias may be effectively treated with the compounds of this invention.

The present invention also provides methods of treatment of diseases caused by pathological levels of proteases, particularly cysteine and serine proteases, more particularly cysteine proteases, even more particularly as inhibitors of cysteine proteases of the papain superfamily, yet more particularly cysteine proteases of the cathepsin family, which methods comprise administering to an animal, particularly a mammal, most particularly a human in need thereof a compound of the present invention. The present invention especially provides methods of treatment of diseases caused by pathological levels of cathepsin K, which methods comprise administering to an animal, particularly a mammal, most particularly a human in need thereof an inhibitor of cathepsin K, including a compound of the present invention. The present invention particularly provides methods for treating diseases in which cysteine proteases are implicated, including infections by pneumocystis carinii, trypsanoma cruzi, trypsanoma brucei, and Crithidia fusiculata; as well as in schistosomiasis, malaria, tumor metastasis, metachromatic leukodystrophy, muscular dystrophy, amytrophy, and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis. Paget's disease, hypercalcemia of malignancy, and metabolic bone disease.

This invention further provides a method for treating osteoporosis or inhibiting bone loss which comprises internal administration to a patient of an effective amount of a compound of Formula I, alone or in combination with other inhibitors of bone resorption, such as bisphosphonates (i.e., allendronate), hormone replacement therapy, anti-estrogens, or calcitonin. In addition, treatment with a compound of this invention and an anabolic agent, such as bone morphogenic protein, iproflavone, may be used to prevent bone loss or to increase bone mass.

For acute therapy, parenteral administration of a compound of Formula I is referred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compounds are administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention.

Biological Assays

The compounds of this invention may be tested in one of several biological assays to determine the concentration of compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 uM final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemitsry*, 1989, 28, 140):

$$v = V_m A / [K_a(1 + I/K_{i,\,app}) + A] \tag{1}$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC] = v_{ss}t + (v_0 - v_{ss})[1 - \exp(-k_{obs}t)]/k_{obs} \tag{2}$$

where [AMC] is the concentration of product formed over time t, $v_0$ is the initial reaction velocity and $v_{ss}$ is the final steady state rate. Values for $k_{obs}$ were then analyzed as a linear function of inhibitor concentration to generate an apparent second order rate constant ($k_{obs}$/inhibitor concentration or $k_{obs}/[I]$) describing the time-dependent inhibition. A complete discussion of this kinetic treatment has been fully described (Morrison et al., *Advz. Enzymol. Relat. Areas Mol. Biol.*, 1988, 61, 201).

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 min on ice The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 min on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to 1.5×10⁴/mL in EMEM medium, supplemented with 10% fetal calf serum and 1.7 g/liter of sodium bicarbonate. 3 mL aliquots of the cell suspension (per treatment) were decanted into 15 mL centrifuge tubes. These cells were pelleted by centrifugation. To each tube 3 mL of the appropriate treatment was added (diluted to 50 uM in the EMEM medium). Also included were appropriate vehicle controls, a positive control (87MEM1 diluted to 100 ug/mL) and an isotype control (IgG2a diluted to 100 ug/mL). The tubes were incubate at 37° C. for 30 min.

0.5 mL aliquots of the cells were seeded onto sterile dentine slices in a 48-well plate and incubated at 37° C. for 2 h. Each treatment was screened in quadruplicate. The slices were washed in six changes of warm PBS (10 mL/well in a 6-well plate) and then placed into fresh treatment or control and incubated at 37° C. for 48 h. The slices were then washed in phosphate buffered saline and fixed in 2% glutaraldehyde (in 0.2M sodium cacodylate) for 5 min., following which they were washed in water and incubated in buffer for 5 min at 37° C. The slices were then washed in cold water and incubated in cold acetate buffer/fast red garnet for 5 min at 4° C. Excess buffer was aspirated, and the slices were air dried following a wash in water.

The TRAP positive osteoclasts were enumerated by bright-field microscopy and were then removed from the surface of the dentine by sonication. Pit volumes were determined using the Nikon/Lasertec ILM21W confocal microscope.

General

Nuclear magnetic resonance spectra were recorded at either 250 or 400 MHz using, respectively, a Bruker AM 250 or Bruker AC 400 spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel.

Where indicated, certain of the materials were purchased from the Aldrich Chemical Co., Milwaukee, Wis., Chemical Dynamics Corp., South Plainfield, N.J., and Advanced Chemtech, Louisville, Ky.

EXAMPLES

In the following synthetic examples, temperature is in degrees Centigrade (° C.). Unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

Preparation of (S)-3N-(N-(Thianaphthenyl-2-carbonyl)-leucinyl)-amino-1N-(3-{2-(1-oxo)-pyridyl}phenylacetyl)-amino-butan-2-one a) 3-(2-Pyridyl)-phenyl Acetic Acid Methyl Ester Methyl 3-bromophenylacetate (25 g, 0.109 mol), 2-(trifluoro-methylsulfonyloxy)-pyridine (24.8 g, 0.109 mol), anhydrous lithium chloride (13.89 g, 0.3275 mol), and tetrakis(triphenylphosphine)palladium (6.31 g, 0.0055 mol) were combined, followed by hexamethylditin (35.8 g, 0.109 mol) and anhydrous dioxane (300 ml). The mixture was stirred at reflux for 16h, cooled, and poured into 1:1 saturated KF-EtOAc (1.6 L). The mixture was stirred at RT for 2 h, filtered, and the filtrate was washed with saturated aqueous $NaHCO_3$ (200 ml) and with brine (200 ml), dried ($MgSO_4$), and concentrated in vacuo to give a brown oil. The residue was flash chromatographed (silica gel, 1:4 EtOAc:hexane) to give the title compound as a yellow oil (11.9 g. 48% yield): MS(ES⁺) 228.1 (MH⁺). cf. *Tetrahedron Letters*, 1995, 36, 9085–9088 b) 3-(2-Pyridyl)phenyl Acetic Acid

To a solution of the compound of 3-(2-pyridyl)-phenyl acetic acid methyl ester (3.8 g, 16.7 mmol) in THF (50 mL) was added a solution of LiOH.H₂O (780.2 mg, 18.6 mmol) in $H_2O$ (10 mL). The reaction was stirred at room temperature until TLC analysis indicated the complete consumption of starting material (2 h). The reaction mixture was concentrated to remove THF, then neutralized to pH=7 by the addition of IN HCl, diluted with brine (50 mL), and washed with $CHCl_3$ (100 mL) The aqueous layer was readjusted back to pH=7 by the addition on IN NaOH and washed with fresh $CHCl_3$ (100 mL). After repeating this procedure once more, the organic layers were combined, dried, filtered ($MgSO_4$) and concentrated to give 3.79 g of the title compound: MS (ES⁺) 214.3 (MH⁺).

c) (S)-N-Boc-3-amino-1-N-(3-(2-pyridyl)-phenyl Acetyl)-amino-butan-2-ol (S)-N-Boc-3-amino-2-hydroxy-butyl amine (as described in *J. Med. Chem.* 1989, 32, 165–170) (6.4 g, 31.37 mmol) was dissolved in DMF (60 ml). Then N-methyl morpholine (3.5 ml, 31.7 mmol), 3-(2-pyridyl)-phenyl acetic acid (6.7 g, 31.37 mmol), and HBTU (12 g, 31.7 mmol) were added, and the reaction mixture was stirred overnight. Then the reaction mixture was concentrated in vacuo, then chromatographed on silica gel to yield the title compound as a white solid (5.7 g, 45%): MS (ES+) 400.2 (M+H⁺).

d) (S)-3-Amino-1N-(3-(2-pyridyl)-phenyl Acetyl)-amino-butan-2-ol (S)-N-Boc-3-amino-1-N-(3-(2-pyridyl)-phenyl acetyl)-amino-butan-2-ol (2.6 g, 65 mmol) was dissolved in 4 M HCl in dioxane (80 ml) and was stirred at RT overnight. Toluene (200 ml) was added, then the reaction mixture was concentrated in vacuo and the resulting title compound was used in the following reaction without further purification: MS (ES+) 300.3 (M+H⁺).

e) (S)-3-N-(N-Boc-leucinyl)-amino-1-N-(3-(2-pyridyl)-phenyl Acetyl)-amino-butan-2-ol (S)-3-amino-1N-(3-(2-pyridyl)-phenyl acetyl)-amino-butan-2-ol (2.4 g, 6.5 mmol) was dissolved in DMF (25 ml).

Then N-methyl morpholine (3.5 ml. 31.7 mmol), Boc-leucine (2.0 g, 8 mmol). and HBTU (3.0 g, 8 mmol), were added, and the reaction mixture was stirred overnight. Then the reaction mixture was concentrated in vacuo, then the crude product was triturated in ether and the white solid was used in the next reaction without further purification (2.65 g, 80%): MS (ES+) 513.4 (M+H$^+$).

f) (S)-3-N-(N-Boc-leucinyl)-amino-1-N-({2-(1-oxo)-pyridyl}phenylacetyl)-amino-butan-2-ol (S)-3-N-(N-Boc-leucinyl)-amino-1-N-(3-(2-pyridyl)-phenyl acetyl)-amino-butan-2-ol (0.45 g, 0.8 mmol) was suspended in methylene chloride (10 ml), then metachloroperbenzoic acid (0.34 g, 1.96 mmol) was added. The reaction became homogeneous stirring at RT for 6 h. The reaction mixture was extracted with 7% aq. NaHCO$_3$, dried with magnesium sulfate and was used in the next reaction without further purification: MS (ES+) 529.4 (M+H$^+$).

g) (S)-3N-(Leucinyl)-amino-1-N-(3-{2-(1-oxo)-pyridyl}phenylacetyl)-amino-butan-2-ol (S)-3-N-(N-Boc-leucinyl)-amino-1-N-({2-(1-oxo)-pyridyl}phenylacetyl)-amino-butan-2-ol (0.42 g. 0.8 mmol) was dissolved in 4 M HCl in dioxane (10 ml) and was stirred at RT for 2 h. Toluene (30 ml) was added, then the reaction mixture was concentrated in vacuo and the resulting title compound was used in the following reaction without further purification: MS (ES+) 429.2 (M+H$^+$).

h) (S)-3N-(N-Thianaphthenyl-2-carbonyl-leucinyl)-amino-1-N-(3-{2-(1-oxo)-pyridyl}phenylacetyl)-amino-butan-2-ol (S)-3N-(leucinyl)-amino-1-N-(3-({2-(1-oxo)-pyridyl}phenylacetyl)-amino-butan-2-ol (0.185 g, 0.4 mmol) was dissolved in DMF (4 ml). Then N-methyl morpholine (0.13 ml, 1.2 mmol), thianaphthenyl-2-carboxylic acid (0.07 g 0.4 mmol), and HBTU (0.17 g, 0.44 mmol) were added, and the reaction mixture was stirred overnight. Then the reaction mixture was concentrated in vacuo, then the crude product was triturated in ether and the white solid was used in the next reaction without further purification (0.13 g, 55%): MS (ES+) 589.2 (M+H$^+$).

i) (S)-3N-(N-(Thianaphthenyl-2-carbonyl)-leucinyl)-amino-1N-(3-{2-(1-oxo)-pyridyl}phenylacetyl)-amino-butan-2-one Dess-Martin periodinane (J. Org. Chem. 1983, 48, 4155–4156)(0.14 g, 0.33 mmol) was added to a solution of (S)-3N-(N-thianaphthenyl-2-carbonyl-leucinyl)-amino-1-N-(3-{2-(1-oxo)-pyridyl}phenylacetyl)-amino-butan-2-ol (0.13 g, 0.22 mmol) in DCM (6 ml) and was stirred at RT for 1 h. The crude reaction was diluted with 10 ml DCM, then 10% aqueous Na$_2$S$_2$O$_3$ (10 ml) and aqueous 10% NaHCO$_3$ (10 ml) was added and the reaction was stirred for 10 min. The organic layer was dried (MgSO$_4$), filtered, concentrated in vacuo, and chromatographed on silica gel (7%MeOH, DCM) to yield the title compound as a white solid (87.2 mg, 68%): MS (ES+) 587.2 (M+H$^+$).

Example 2

Preparation of (S)-3N-(N-(Benzyloxycarbonyl)-L-leucinyl)amino-1N-[3-{2-(1-oxo)-pyridyl}phenylacetyl]amino-2-butanone a) (S)-3N-(N-(Benzyloxycarbonyl)-L-leucinyl)amino-1N-[3-{2-(1-oxo)-pyridyl}phenylacetyl]amino-2-butanone Following the procedure of Example 1(a–d), 1(f), and 1(i), except substituting "Cbz-leucine" for "Boc-leucine", the title compound was prepared: MS (ES+) 561.3 (M+H$^+$), 1121.4 (2M+H$^+$).

Example 3

Preparation of (S)-3N-[N-((5-Morpholinoethyloxy) benzofuryl-2-carbonyl)-L-leucinyl)]amino-1N-[3-(2-(1-oxo)pyridyl)phenylacetyl]amino-2-butanone a) Ethyl 5-Hydroxybenzofuran-2-carboxylate To a mixture of aluminum chloride (6.3 g, 47.7 mmol) and ethanethiol (4.5 g, 72.9 mmol) in dichloromethane (81 mL) at 0° C. was added ethyl 5-methoxybenzofuran-2-carboxylate (3.0 g, 13.6 mmol). After stirring for 16 h at room temperature, the mixture was poured into water, acidified with 3N HCl and extracted with dichloromethane (2x). The organic layers were combined, washed with brine, collected, dried (MgSO$_4$), filtered and concentrated. The residue was purified by column chromatography (silica gel, ethyl acetate/hexane) to yield the title compound as a white solid (2.16 g, 77%). $^1$H NMR (400 MHz, CDCl$_3$) δ 7.45 (m, 2H), 7.08 (m, 1H), 7.02 (m, 1H), 5.35 (s b, 1H), 4.44 (q, 2H), 1.42 (t, 3H).

b) Ethyl 5-(2-N-Morpholino)ethoxybenzofuran-2-carboxylate

To a solution of the compound of Example 169(a) (0.200 g 0.971 mmol), 4-(2-hydroxyethyl)morpholine (0.165 g, 1.26 mmol), and triphenylphosphine (0.331 g, 1.26 mmol) in THF (4 mL) at 0° C. was added dropwise diisopropylazodicarboxylate (0.254 g, 1.26 mmol). After stirring at room temperature or 16 h, the solution was concentrated and purified by column chromatography (silica gel, ethyl acetate/hexane) to yield the title compound as a white solid (0.235 g, 76%). $^1$H NMR (400 MHz, CDCl$_3$) δ 7.48 (m, 2H), 7.07 (m, 2H), 4.43 (q, 2H), 4.14 (m, 2H), 3.76 (m, 4H), 2.86 (m, 2H), 2.61 (m, 4H), 1.40 (t, 3H).

c) 5-(2-N-Morpholino)ethoxybenzofuran-2-carboxylic Acid

A solution of the compound of Example 49(b) (0.235 g, 0.736 mmol) and lithium hydroxide monohydrate (0.033 g, 0.810 mmol) in THF (2 mL) and water (2 mL) was stirred at reflux for 2 h. The solution was concentrated, and the residue dissolved in water and acidified with 1.1 eq of 1N HCl. The solution was placed on a lyophilizer for 16 h to yield the title compound as a white solid (0.150 g, 70%). MS (ESI): 292.1 (M+H)$^+$.

d) (S)-3-[(5-Morpholinoethyloxy)benzofuryl-2-carbonyl-L-leucinyl)]amino-1-[3-(2-(1-oxo)pyridyl)phenylacetyl] amino-2-butanol Following the procedure of Example 1(a–h), except substituting "(5-morpholinoethyloxy)benzofuryl-2-carboxylic acid" for "thianaphthenyl-2-carboxylic acid", the title compound was prepared: MS (ES+) 702.4 (M+H$^+$), e) (S)-3N-[N-((5-Morpholinoethyloxy)benzofuryl-2-carbonyl)-L-leucinyl)]amino-1N-[3-(2-(1-oxo)pyridyl) phenylacetyl]amino-2-butanone (S)-3-[(5-Morpholinoethyloxy)benzofuryl-2-carbonyl-L-leucinyl)]amino-1-[3-(2-(1-oxo)pyridyl)phenylacetyl] amino-2-butanol (0.06 g, 0.086 mmol) was dissolved in DMSO (2 ml) and triethyl amine (0.083 ml, 1.2 mmol). Then sulfur trioxide-pyridine complex (0.041 g, 0.52 mmol) was added and the reaction was stirred 1 h. Then an additional portion of sulfur trioxide-pyridine complex (0.041 g, 0.52 mmol) and triethyl amine (0.083 ml. 1.2 mmol) was added and the reaction was stirred an additional hour. The reaction mixture was concentrated in vacuo and chromatographed (silica gel. 0.8% NH$_4$OH. 5% MeOH, CH$_2$Cl$_2$) to yield the title compound as a white solid (44.7 mg, 52%): MS (ES+) 700.4 (M+H$^+$).

Example 4

Preparation of 1N-(N-(Thiophene-2-carbonyl)-leucinyl)-amino-3N-(3-(2-pyridyl)-phenyl Acetyl)-amino-propan-2-one a)1-N-(N-Boc-leucinyl)-amino-3-N-(3-(2-pyridyl)-phenyl Acetyl)-amino-propan-2-ol 1,3-Diamino-propan-2-ol (5.61 g, 22.5 mmol) was dissolved in DMF (36 ml). Then HOBT-hydrate (3.34 g, 24.75 mmol). Boc-L-leucine (5.61 g, 22.5 mmol), and EDCI (4.73 g. 24.75 mmol) were added, and the reaction mixture was stirred for 4 h; then 3-(2-pyridyl)-phenyl acetic acid (1.68 g, 7.875 mmol, Example 1(a)–(b)) was added, followed by HOBT-hydrate (1.276 g, 9.45 mmol) and EDCI (1.81 g, 9.45 mmol), and the reaction was stirred an additional 12 h. The reaction mixture was concentrated in vacuo, then chromatographed on silica gel to yield the title compound as a white solid (1.70 g, 43%): MS (ES+) 499.3 (M+H$^+$).

b)1-N-(Leucinyl)-amino-3-N-(3-(2-pyridyl)-phenyl Acetyl)-amino-propan-2-ol

1-N-(N-Boc-leucinyl)-amino-3-N-(3-(2-pyridyl)-phenyl acetyl)-amino-propan-2-ol (0.3 g, 0.6 mmol) was dissolved in 1.5:1 TFA:DCM (25 ml) and was stirred at RT for 2 h. Toluene (10 ml) was added, then the reaction mixture was concentrated in vacuo and the resulting title compound was used in the following reaction without further purification: MS (ES+) 399.2 (M+H$^+$).

c) 1-N-(N-(Thiophene-2-carbonyl)-leucinyl)-amino-3-N-(3-(2-pyridyl)-phenyl Acetyl)-amino-propan-2-ol EDCI (0.138 g, 0.722 mmol) was added to a solution of 1-N-(leucinyl)-amino-3-N-(3-(2-pyridyl)-phenyl acetyl)-amino-propan-2-ol (0.6 mmol), DIEA (0.315 ml, 1.81 mmol), HOBT (0.097 g, 0.722 mmol), and thianaphthenyl-2-carboxylic acid (0.077 g, 0.6 mmol) in DMF (10 ml). The reaction mixture was stirred overnight, then was washed with brine/EtOAc; the combined organics were dried (MgSO$_4$), filtered, concentrated in vacuo, and chromatographed on silica gel to yield the title compound as a white foam (0.15 g, 49%): MS(ES) (ES+) 509.3 (M+H$^{+)\cdot}$ d)1N-(N-(Thiophene-2-carbonyl)-leucinyl)-amino-3N-(3-(2-pyridyl)-phenyl acetyl)-amino-propan-2-one Dess-Martin periodinane (*J. Org. Chem.* 1983, 48, 4155–4156)(0.091 g, 0.324 mmol) was added to a solution of 1-N-(N-(thiophene-2-carbonyl)-leucinyl)-amino-3-N-(3-(2-pyridyl)-phenyl acetyl)-amino-propan-2-ol (0.11 g, 0.216 mmol) in DCM (10 ml) and was stirred for 3 h. The reaction was diluted with 10 ml DCM, then 10% aqueous Na$_2$S$_2$O$_3$ (10 ml) and aqueous 10% NaHCO$_3$ (10 ml) was added and the reaction was stirred for 10 min. The organic layer was dried (MgSO$_4$), filtered, concentrated in vacuo, and chromatographed on silica gel to yield the title compound as a white solid (70 mg, 64%): MS (ES+) 507.4 (M+H$^+$).

Example 5

Preparation of 1N-(N-(3,4-Dichlorobenzoyl)-L-leucinyl)amino-3N-[3-(2-pyridyl)phenylacetyl]amino-2-propanone a) 1N-(N-(3,4-Dichlorobenzoyl)-L-leucinyl)amino-3N-[3-(2-pyridyl)-phenylacetyl]amino-2-propanone Following the procedure of Example 4(a–d), except substituting "3,4-dichlorobenzoic acid" for "thianaphthenyl-2-carboxylic acid", gave the title compound: MS (ES+) 569.2 (M+H$^+$).

Example 6

Preparation of 1N-(N-(Methylpiperidine-4-carbonyl)-L-leucinyl)amino-3N-[3-(2-pyridyl) phenylacetyl]amino-2-propanone a) 1N-(N-(Methylpiperidine-4-carbonyl)-L-leucinyl)amino-3N-[3-(2-pyridyl)phenylacetyl]amino-2-propanone Following the procedure of Example 4(a–d), except substituting "N-methylpiperidine-4-carboxylic acid" for "thianaphthenyl-2-carboxylic acid", gave the title compound: MS (ES+) 522.3 (M+H$^+$).

Example 7

Preparation of 1-(N-4-((7-Nitro-2,1,3-benzooxadiazole)-L-pyrroiidinyl-)-N-(L-leucinyl))-amino-3N-[3-(2-pyridyl)phenylacetyl]amino-2-propanone a) 1-(N-4-((7-Nitro-2,1,3-benzooxadiazole)-L-pyrrolidinyl-)-N-(L-leucinyl))-amino-3N-[3-(2-pyridyl) phenylacetyl]amino-2-propanone Following the procedure of Example 4(a–d), except substituting "(7-nitro-2,1,3-benzoxadiazol-4-yl)-L-proline" for "thianaphthenyl-2-carboxylic acid", gave the title compound: MS (ES+) 657.2 (M+H$^+$).

Example 8

Preparation of 1N-(N-(5-Methylimidazolyl-4-carbonyl)-L-leucinyl)amino-3N-[3-(2-pyridyl) phenylacetyl]amino-2-propanone a) 1N-(N-(5-Methylimidazolyl-4-carbonyl)-L-leucinyl) amino-3N-[3-(2-pyridyl)phenylacetyl]amino-2-propanone Following the procedure of Example 4(a–d), except substituting "5-methylimidazolyl-4-carboxylic acid" for "thianaphthenyl-2-carboxylic acid", gave the title compound: MS (ES+) 505.3 (M+H$^+$).

Example 9

Preparation of 1N-(N-(5-Butylpyridine-2-carbonyl)-L-leucinyl)amino-3N-[3-(2-pyridyl)phenylacetyl] amino-2-propanone a) 1N-(N-(5-Butylpyridine-2-carbonyl)-L-leucinyl)amino-3N-[3-(2-pyridyl)phenylacetyl]amino-2-propanone Following the procedure of Example 4(a–d), except substituting "5-butylpyridine-2-carboxylic acid" for "thianaphthenyl-2-carboxylic acid", gave the title compound: MS (ES+) 558.5 (M+H$^+$).

Example 10

Preparation of 1N-[N-(Cbz-2-(N,N-Dimethylamino) ethyl)-glycyl-N-L-leucinyl]amino-3N-[3-(2-pyridyl) phenylacetyl]amino-2-propanone a) 1N-[N-(Cbz-2-(N,N-Dimethylamino)ethyl)-glycyl-N-L-leucinyl]amino-3-[3-(2-pyridyl)phenylacetyl]amino-2-propanone Following the procedure of Example 4(a–d), except substituting "N-Cbz-2-(N,N-dimethylamino)ethylglycine" for "thianaphthenyl-2-carboxylic acid", gave the title compound: MS (ES+) 659.5 (M+H$^+$).

Example 11

Preparation of 1N-1N-(5-(Morpholinoethyloxy) benzofuryl-2-carbonyl)-L-leucinyl]amino-3N-[3-(2-pyridyl)phenylacetyl]amino-2-propanone a) 1-[5-(Morpholinoethyloxy)benzofuryl-2-carbonyl-L-leucinyl]amino-3-[3-(2-pyridyl)phenylacetyl]amino-2-propanol Following the procedure of Example 4(a–c), except substituting "5-(Morpholinoethyloxy)benzofuryl-2-carboxylic acid" (Example 3(a)–(c) for preparation) for "thianaphthenyl-2-carboxylic acid", gave the title compound: MS (ES+) xxx.x (M+H$^+$).

b) 1N-[N-(5-(Morpholinoethyloxy)benzofuryl-2-carbonyl)-L-leucinyl]amino-3-[3-(2-pyridyl)phenylacetyl]amino-2-propanone Following the procedure of Example 3(e), except substituting "1-[5-morpholinoethyloxy)benzofuryl-2-carbonyl-L-leucinyl]amino-3-[3-(2-pyridyl)phenylacetyl]amino-2-propanol" for "(S)-3-[(5-morpholinoethyloxy)benzofuryl-2-carbonyl-L-leucinyl)]amino-1-[3-(2-(1-oxo)pyridyl) phenylacetyl]amino-2-butanol", gave (the title compound: MS (ES+) 670.3 (M+H$^+$).

Example 12

Preparation of (S)-3N-(N-(Benzothiazolidyl-6-carbonyl)-L-Leucinyl)amino-1N-[3-(2-pyridyl) phenylacetyl]amino-2-butanone a) (S)-3N-(N-(Benzothiazolidyl-6-carbonyl)-L-Leucinyl) amino-1N-[3-(2-pyridyl)phenylacetyl]amino-2-butanone Following the procedure of Example 1(a–e) and 1(g–i) except substituting "benzothiazolidyl-6-carboxylic acid" for "thianaphthenyl-2-carboxylic acid", gave the title compound: MS (ES+) 572.3 (M+H$^+$).

Example 13

Preparation of 1-(Benzyloxycarbonyl-L-leucinyl) amino-3-[3-(phenyl)phenylacetl]amino-2-propanone a) 3-Bromo-phenyl Methyl Acetate 3-Bromo phenyl acetic acid (2.15 g, 10 mmol) was dissolved in MeOH, then concentrated sulfuric acid was added and the reaction mixture was refluxed for 1.5 h, concentrated in vacuo, dissolved in EtOAc, extracted with water, and the combined organic extracts were dried with magnesium sulfate, filtered, concentrated in vacuo and was used in the next reaction without further purification: 1H NMR: 7.4–7.1 (m, 4H), 3.7 (s, 3H), 3.6 (s, 2H).

b) 3-Biphenyl Methyl Acetate 3-bromo-phenyl methyl acetate (2.29 g, 10 mmol) was dissolved in toluene (30 ml). Then, phenyl boronic acid (1.46 g, 12 mmol) was added followed by aqueous sodium carbonate (2M. 4.24 ml, 40 mmol), then tetrakis (triphenylphosphine) palladium (0.35 g, 0.3 mmol) and was refluxed overnight. The reaction was cooled to RT, diluted with saturated ammonium chloride, then extracted with EtOAc (2×10 ml). The combined organics were dried with magnesium sulfate, filtered, concentrated, and chromatographed (silica gel, 5% EtOAc:hexanes) to provide the desired product as a white solid (1.93 g, 84%): MS(ES) 263 (M +H$^+$).

c) 3-Biphenyl Acetic Acid

3-Biphenyl acetyl methyl ester was dissolved in MeOH (40 ml) and water (6 ml), then LiOH-hydrate (0.7 g, 16.8 mmol) was added, and the reaction was stirred at RT for 2 h. The reaction was diluted with water, acidified with 6N hydrochloric acid (1 ml), then with EtOAc (2×10 ml). The combined organics were dried with magnesium sulfate, filtered, and concentrated to give the desired product as a white solid (1.66 g, 93%): 1H NMR: d: 7.6–7.25 (m. 9H), 3.7 (s, 2H)

d)1-(Benzyloxycarbonyl-L-leucinyl)amino-3-[3-(phenyl) phenylacetyl]amino-2-propanone Following the procedure of Example 4(a–d), except substituting "Cbz-leucine" for "Boc-leucine" and "3-(phenyl) phenylacetic acid" for "3-(2-pyridyl)phenylacetic acid" gave the title compound: MS (ES+) 530.3 (M+H$^+$), 552.2 (M+Na$^+$).

Example 14

Preparation of (S)-3N-(N-(5-Methoxycarbonylbenzofuryl-2-carbonyl)-L-leucinyl) amino-1N-[3-(2-pyridyl)phenylacetyl]amino-2-butanone a) 4-Benzyloxycarbonylmethoxy-3-formylbenzaldehyde To a mixture of 5-formylsalicylaldehyde (2.2 g, 14.7 mmol) and potassium bromide (5.0 g, 36.8 mmol) in acetone (50 mL) was added benzyl bromoacetate (4.8 g, 16.1 mmol). After stirring at reflux for 6 h, the mixture was diluted with ethyl acetate and washed with water and brine. The organic layer was collected, dried (MgSO$_4$), filtered and concentrated to yield the title compound (4.13 g, 94%). $^1$H NMR (400 MHz, CDCl$_3$) δ 10.56 (s, 1H), 9.95 (s, 1H), 8.38 (s, 1H), 8.07 (d, 1H), 7.38 (m, 5H), 6.95 (d, 1H), 5.26 (s, 2H), 4.91 (s, 2H).

b) Benzyl 5-Formylbenzofuran-2-carboxylate

A mixture of 4-benzyloxycarbonylmethoxy-3-formylbenzaldehyde (4.12 g, 13.8 mmol) and potassium carbonate (4.8 g, 35 mmol) was stirred at 80° C. in DMF (20 mL) for 5 h. The mixture was cooled and partitioned between ethyl acetate and water. The organic layer was washed with water and brine then dried (MgSO$_4$), filtered and concentrated. The residue was purified by column chromatography (silica gel, ethyl acetate/hexane) to yield the title compound as a white solid (1.78 g, 46%). $^1$H NMR (400 MHz, CDCl$_3$) δ 10.09 (s, 1H), 8.24 (s, 1H), 8.05 (d, 1H), 7.71 (d, 1H), 7.68 (s, 1H), 7.42 (m, 5H), 5.43 (s, 2H).

c) Benzyl 5-Carboxybenzofuran-2-carboxylate

To a solution of benzyl 5-formylbenzofuran-2-carboxylate (0.380 g, 0.1.36 mmol) in THF (5 mL) and t-butanol (1 mL) was added slowly a solution of sodium chlorite (0.245 g 2.71 mmol) and sulfamic acid (0.277 g, 2.86 mmol) in water (2 mL). After stirring at room temperature for 3 h, the solution was partitioned between ethyl acetate and water. The organic layer was washed successively with water, saturated aqueous sodium bicarbonate, and brine then collected, dried (MgSO$_4$), filtered and concentrated to yield the title compound as an off-white solid (0.272 g, 68%). $^1$H NMR (400 MHz, CDCl$_3$) δ 8.52 (s, 1H), 8.23 (d, 1H), 7.67 (m, 2H), 7.49 (m, 2H), 7.41 (m, 3H), 5.46 (s, 2H).

d) Benzyl Methoxy-carbonylbenzofuran-2-carboxylate

To a solution of the benzyl 5-carboxybenzofuran-2-carboxylate(0.8 g, 2.7 mmol) in Et$_2$O (3 mL) was added a solution of diazomethane in Et$_2$O (8.1 mmol) After stirring at RT for 45 min, argon was bubbled through the solution for 10 minutes. Then, the solution was concentrated in vacuo and was used in the next reaction without further purification (0.144 g, 45%): 1H NMR:

e) 5-Methoxy-carbonylbenzofuran-2-carboxylic Acid

To a solution of benzyl methoxy-carbonylbenzofuran-2-carboxylate (0.144 g, 0.409 mmol) in ethyl acetate (20 mL) was added 10% palladium on carbon (0.072 g, 50% w/w). After stirring under a hydrogen atmosphere for 2 h, the mixture was filtered through Celite. The filtrate was concentrated to yield the title compound as a white solid (0.098 g, 91%): 1H NMR:

f) (S)-3N-(N-(5-Methoxycarbonylbenzofuryl-2-carbonyl)-L-leucinyl)amino-1N-[3-(2-pyridyl)phenylacetyl]amino-2-butanone Following the procedure of Example 1(a–e) and 1(g–i) except substituting "5-methoxycarbonylbenzofuryl-2-carboxylic acid" for "thianaphthenyl-2-carboxylic acid", gave the title compound: MS (ES+) 613.2 (M+H$^+$).

Example 15

Preparation of (S)-3N-[N-{4-Methoxy-3-(N,N-dimethylaminoethyl)oxy}benzoyl-L-leucinyl]amino-1N-[3-(2-pyridyl)phenylacetyl]amino-2-butanone a) (S)-3N-[N-{4-Methoxy-3-(N,N-dimethylaminoethyl) oxy}benzoyl-L-leucinyl]amino-1N-[3-(2-pyridyl) phenylacetyl]amino2-butanone Following the procedure of Example 1(a–e) and Example 3(e) except substituting "4-methoxy-3-(N,N-dimethylaminoethyl)oxy}benzoic acid" for "thianaphthenyl-2-carboxylic acid", gave the title compound: MS (ES+) 632.4 (M+H$^+$).

Example 16

Preparation of (S)-3N-[N-(3-(4-Methylpiperazinyl))-benzoyl}-L-leucinyl]amino-1N-[3-(2-pyridyl) phenylacetyl]amino-2-propanone a) 3-Bromo-benzoic Acid Tert-butyl Ester 2,4,6-Trichlorobenzoic acid (11.7 ml, 75 mmol) was added dropwise to a solution of 3-bromobenzoic acid (15 g, 75 mmol), triethyl amine (10.5 ml, 75 mmol) in THF (25 ml) at RT. The reaction was stirred 15 min. Then, t-butanol (7.1 ml, 150 mmol) and DMAP (18.3 g, 150 mmol) were added and the reaction was stirred overnight. The crude reaction was filtered through a pad of silica gel, concentrated, and was used in the next reaction without further purification.
b) 3-(4-Methylpiperazinyl)-benzoic Acid tert-butyl Ester 3-Bromo-benzoic acid tert-butyl ester (6.7 g, 26 mmol), N-methyl piperizine (3.4 ml, 31.2 mmol), sodium t-butoxide (3.5 g, 36.4 mmol). 2,2'-bis(diphenylphosphino)-1,1'-binaphthyl (0.12 g, 0.195 mmol), tris(dibenzylideneacetone) dipalladium(0) (0.067 g, 0.065 mmol) were combined in toluene (200 ml), then was heated to 80 degrees C. Argon gas was then bubbled through the solution for 5 minutes. The reaction mixture was heated and stirred for 5 h. The reaction was then cooled to RT, concentrated in vacuo, and chromatographed (silica gel, 4% MeOH: $CH_2Cl_2$) to yield the title compound (4.12 g, 58%).
c) 3-(4-Methylpiperazinyl)-benzoic Acid 3-(4-Methylpiperazinyl)-benzoic acid tert-butyl ester (4.1 g, 14.9 mmol) was dissolved in TFA: $CH_2Cl_2$ (70 ml, 1:1) and the reaction was stirred for 2 h at RT. The reaction mixture was diluted with toluene (100 ml), then was concentrated in vacuo and was used in the next reaction without further purification: MS (ES+) 221.3 (M+H$^+$).
d) (S)-3N-[N-(3-(4-Methylpiperazinyl))-benzoyl}-L-leucinyl]amino-1N-[3-(2-pyridyl)phenylacetyl]amino-2-propanone Following the procedure of Example 1(a–e) and Example 3(e) except substituting "3-(4-Methylpiperazinyl)benzoic acid" for "thianaphthenyl-2-carboxylic acid", gave the title compound: MS (ES+) 613.4 (M+H$^+$).

Example 17

Preparation of (S)-3N-[N-{(N-Methyl-N'-(4-(1-methylpiperidinyl)amino}benzoyl}-L-leucinyl] amino-1N-[3-(2-pyridyl)phenylacetyl]amino-2-butanone a) 3-{(N-Methyl-N'-(4-(1-methylpiperidinyl) amino}benzoic Acid Following the procedure of Example 16(a–c) "N-Methyl-N'-(4-(1-methylpiperidinyl)amine" for "N-methyl-piperizine", gave the title compound: MS (ES+) 249.4 (M+H$^+$).
b) (S)-3N-[N-{(N-Methyl-N'-(4-(1-methylpiperidinyl) amino}benzoyl}-Lleucinyl]amino-1N-[3-(2-pyridyl) phenylacetyl]amino-2-butanone Following the procedure of Example 1(a–e) and Example 3(e) except substituting "3-(3-{(N-Methyl-N'-(4-(1-methylpiperidinyl)amino}benzoic acid" for "thianaphthenyl-2-carboxylic acid", gave the title compound: MS (ES+) 641.4 (M+H$^+$).

Example 18

Preparation of (S)-3N-[N-{(N-Methyl-N'-(beta-N,N-dimethylaminoethyl)amino}benzoyl-L-leucinyl] amino-1N-[3-(2-pyridyl)phenylacetyl]amino-2-butanone a) [3-{(N-Methyl-N'-(beta-N,N-dimethylaminoethyl) amino}benzoic acid Following the procedure of Example 16(a–c) "N-Methyl-N'-(beta-N,N-dimethylaminoethyl)amine" for "N-methyl-piperizine", gave the title compound.
b) (S)-3N-[N-{(N-Methyl-N'-(beta-N,N-dimethylaminoethyl)amino}benzoyl-L-leucinyl]amino-1N-[3-(2-pyridyl)phenylacetyl]amino-2-butanone Following the procedure of Example 1(a–e) and Example 3(e) except substituting "3-{(N-Methyl-N'-(beta-N,N-dimethylaminoethyl)amino}benzoic acid" for "thianaphthenyl-2-carboxylic acid", gave the title compound: MS (ES+) 615.5 (M+H$^+$).

Example 19

Preparation of (S)-3N-[N-(5-(Morpholinoethyloxy) benzofuryl-2-carbonyl)-L-leucinyl]amino-1N-[3-(2-pyridyl)phenylacetyl]amino-2-butanone a) (S)-3N-[N-(5-(Morpholinoethyloxy)benzofuryl-2-carbonyl)-L-leucinyl]amino-1N-[3-(2-pyridyl) phenylacetyl]amino-2-butanone Following the procedure of Example 1(a–e) and Example 3(e) except substituting "5-(Morpholinoethyloxy) benzofuryl-2-carboxylic acids" for "thianaphthenyl-2-carboxylic acid", gave the title compound: MS (ES+) 684.5 (M+H$^+$).

Example 20

Preparation of (S)-3N-{N-(4-Methyl[4-trifluoromethyl)phenyl]thiazole-5-carbonyl)-L-leucinyl)[}-amino-1N-[3-(2-pyridyl)phenylacetyl] amino-2-butanone a) (S)-3N-{N-(4-Methyl[4-trifluoromethyl)phenyl]thiazole-5-carbonyl)-L-leucinyl)]}-amino-1N-[3-(2-pyridyl) phenylacetyl]amino-2-butanone Following the procedure of Example 1(a–e), Example 3(e) except substituting "4-Methyl[4-trifluoromethyl) phenyl]thiazole-5-carboxylic acid" (purchased from Maybridge Chemicals) for "thianaphthenyl-2-carboxylic acid", gave the title compound: MS (ES+) 680.2 (M+H$^+$).

Example 21

Preparation of 1N-(N-(Biphenyl)-4-carbonyl)-leucinyl)-amino-3N-(3-(2-pyridyl)-phenylacetyl)-amino-propan-2-one a) 1N-(N-(Biphenyl)-4-carbonyl)-leucinyl)-amino-3N-(3-(2-pyridyl)-phenylacetyl)-amino-propan-2-one Following the procedure of Example 4(a–d), except substituting "biphenyl-4-carboxylic acid" for "thianaphthenyl-2-carboxylic acid", gave the title compound: MS (ES+) 577.3 (M+H$^+$).

Example 22

Preparation of 1-N-(N-(Indole-2-carbonyl)-leucinyl)-amino-3-N-(3-(2-pyridyl)-phenylacetyl)-amino-propan-2-one Following the procedure of Example 4(a–d), except substituting "indole-2-carboxylic acid" for "thianaphthenyl-2-carboxylic acid", gave the title compound: MS (ES+) 540.2 (M+H$^+$).

Example 23

Preparation of 1N-(N-(Indole-6-carbonyl)-leucinyl)-amino-3N-(3-(2-pyridyl)-phenylacetyl)-amino-propan-2-one a) 1N-(N-(Indole-6-carbonyl)-leucinyl)-amino-3N-(3-(2-pyridyl)-phenylacetyl)-amino-propan-2-one Following the procedure of Example 4(a–d), except substituting "indole-6-carboxylic acid" for "thianaphthenyl-2-carboxylic acid", gave the title compound: MS (ES+) 540.2 (M+H$^+$).

Example 24

Preparation of 1N-(N-(Adamantane-1-carbonyl)-leucinyl)-amino-3N-(3-(2-pyridyl)-phenylacetyl)-amino-propan-2-one a) 1N-(N-(Adamantane-1-carbonyl)-leucinyl)-amino-3N-(3-(2-pyridyl)-phenylacetyl)-amino-propan-2-one Following the procedure of Example 4(a–d), except substituting "adamantane-1-carboxylic acid" for "thianaphthenyl-2-carboxylic acid", gave the title compound: MS (ES+) 559.3 (M+H$^+$).

Example 25

Preparation of 1N-(N-(1-Methoxy-2-naphthoyl)-leucinyl)-amino-3N-(3-(2-pyridyl)-phenylacetyl)-amino-propan-2-one a) 1-N-(N-(1-Methoxy-2-naphthoyl)-leucinyl)-amino-3-N-(3-(2-pyridyl)-phenylacetyl)-amino-propan-2-one Following the procedure of Example 4(a–d), except substituting "1-methoxy-2-naphthoic acid" for "thianaphthenyl-2-carboxylic acid", gave the title compound: MS (ES+) 581.2 (M+H$^+$).

Example 26

Preparation of 1N-(N-(Benzoyl)-leucinyl)-amino-3N-(3-(2-pyridyl)-phenylacetyl)-amino-propan-2-one a) 1N-(N-(Benzoyl)-leucinyl)-amino-3N-(3-(2-pyridyl)-phenylacetyl)-amino-propan-2-one Following the procedure of Example 4(a–d), except substituting "benzoic acid" for "thianaphthenyl-2-carboxylic acid", gave the title compound: MS (ES+) 501.2 (M+H$^+$).

Example 27

Preparation of 1N-(N-(Thieno[3.2-b]thiophene-2-carbonyl)-leucinyl)-amino-3N-(3-(2-pyridyl)-phenylacetyl)-amino-propan-2-one a) 1N-(N-(Thieno[3,2-b]thiophene-2-carbonyl)-leucinyl)-amino-3N-(3-(2-pyridyl)-phenylacetyl)-amino-propan-2-one Following the procedure of Example 4(a–d), except substituting "thieno[3,2-b]thiophene-2-carboxylic acid" for "thianaphthenyl-2-carboxylic acid", gave the title compound: MS (ES+) 563.2 (M+H$^+$).

Example 28

Preparation of 1N-(N-(4-Cyclohexylbenzoyl)-leucinyl)-amino-3N-(3-(2-pyridyl)-phenylacetyl)-amino-propan-2-one a) 1N-(N-(4-cyclohexylbenzoyl)-leucinyl)-amino-3N-(3-(2-pyridyl)-phenylacetyl)-amino-propan-2-one Following the procedure of Example 4(a–d), except substituting "4-cyclohexylbenzoic acid" for "thianaphthenyl-2-carboxylic acid", gave the title compound: MS (ES+) 583.4 (M+H$^+$).

Example 29

Preparation of 1N-(N-(1-Methylpyrrole-2-carbonyl)-leucinyl)-amino-3N-(3-(2-pyridyl)-phenylacetyl)-amino-propan-2-one a) 1N-(N-(1-Methylpyrrole-2-carbonyl)-leucinyl)-amino-3N-(3-(2-pyridyl)-phenylacetyl)-amino-propan-2-one Following the procedure of Example 4(a–d), except substituting "1-methylpyrrole-2-carboxylic acid" for "thianaphthenyl-2-carboxylic acid", gave the title compound: MS (ES+) 504.4 (M+H$^+$).

Example 30

Preparation of 1N-(N-(4-Methoxybenzoyl)-leucinyl)-amino-3N-(3-(2-pyridyl)-phenylacetyl)-amino-propan-2-one a) 1N-(N-(4-Methoxybenzoyl)-leucinyl)-amino-3N-(3-(2-pyridyl)-phenylacetyl)-amino-propan-2-one Following the procedure of Example 4(a–d), except substituting "4-methoxybenzoic acid" for "thianaphthenyl-2-carboxylic acid", gave the title compound: MS (ES+) 531.4 (M+H$^+$).

Example 31

Preparation of 1N-(N-(Thiophene-3-carbonyl)-leucinyl)-amino-3N-(3-(2-pyridyl)-phenylacetyl)-amino-propan-2-one a) 1N-(N-(Thiophene-3-carbonyl)-leucinyl)-amino-3N-(3-(2-pyridyl)-phenylacetyl)-amino-propan-2-one Following the procedure of Example 4(a–d), except substituting "thiophene-3-carboxylic acid" for "thianaphthenyl-2-carboxylic acid", gave the title compound: MS (ES+) 507.2 (M+H$^+$).

Example 32

Preparation of 1N-(N-(4-(4'-Ethylbiphenyl)carbonyl)-leucinyl)-amino-3N-(3-(2-pyridyl)-phenylacetyl)-amino-propan-2-one a) 1N-(N-(4-(4'-Ethylbiphenyl)carbonyl)-leucinyl)-amino-3N-(3-(2-pyridyl)-phenylacetyl)-amino-propan-2-one Following the procedure of Example 4(a–d), except substituting "4-(4'-ethylbiphenyl)carboxylic acid" for "thianaphthenyl-2-carboxylic acid", gave the title compound: MS (ES+) 605.3 (M+H$^+$).

Example 33

Preparation of 1N-(N-(Pyrazine-2-carbonyl)-leucinyl)-amino-3N-(3-(2-pyridyl)-phenylacetyl)-amino-propan-2-one a) 1N-(N-(Pyrazine-2-carbonyl)-leucinyl)-amino-3N-(3-(2-pyridyl)-phenylacetyl)-amino-propan-2-one Following the procedure of Example 4(a–d), except substituting "pyrazine-2-carboxylic acid" for "thianaphthenyl-2-carboxylic acid", gave the title compound: MS (ES+) 503.3 (M+H$^+$).

Example 34

Preparation of 1N-(N-(Pyrimidine-4-carbonyl)-leucinyl)-amino-3N-(3-(2-pyridyl)-phenylacetyl)-amino-propan-2-one a) 1N-(N-(Pyrimidine-4-carbonyl)-leucinyl)-amino-3N-(3-(2-pyridyl)-phenylacetyl)-amino-propan-2-one Following the procedure of Example 4(a–d), except substituting "pyrimidine-4-carboxylic acid" for "thianaphthenyl-2-carboxylic acid", gave the title compound: MS (ES+) 503.3 (M+H$^+$).

Example 35

Preparation of 1N-(N-(2,7-Dimethylpyrazolo[1,5-a]pyrimidine-6-carbonyl)-leucinyl)-amino-3N-(3-(2-pyridyl)-phenylacetyl)-amino-propan-2-one a) 1N-(N-(2,7-Dimethylpyrazolo[1,5-a]pyrimidine-6-carbonyl)-leucinyl)-amino-3N-(3-(2-pyridyl)-phenylacetyl)-amino-propan-2-one Following the procedure of Example 4(a–d), except substituting "2,7-dimethylpyrazolo[1,5-a]pyrimidine-6-carboxylic acid" for "thianaphthenyl-2-carboxylic acid", gave the title compound: MS (ES+) 570.2 (M+H$^+$).

Example 36

Preparation of 1N-(N-(4,7-Dimethylpyrazolo[5.1-c][1,2,4triazine-3-carbonyl)-leucinyl)-amino-3N-(3-(2-pyridyl)-phenylacetyl)-amino-propan-2-one a) 1N-(N-(4,7-Dimethylpyrazolo[5,1-c][1,2,4]triazine-3-carbonyl)-leucinyl)-amino-3N-(3-(2-pyridyl)-phenylacetyl)-amino-propan-2-one Following the procedure of Example 4(a–d), except substituting "4,7-dimethylpyrazolo[5,1-c][1,2,4]triazine-3-carbonxylic acid" for "thianaphthenyl-2-carboxylic acid", gave the title compound: MS (ES+) 571.3 (M+H$^+$).

Example 37

Preparation of 1N-(N-Thianaphthenyl-2-carbonyl)-leucinyl)-amino-3N-(3-(6-methyl-2-pyridyl)-phenylacetyl)-amino-propan-2-one a) 1N-(N-Thianaphthenyl-2-carbonyl)-leucinyl)-amino-3N-(3-(6-methyl-2-pyridyl)-phenylacetyl)-amino-propan-2-one Following the general procedure of Example 1(a–e), (g–i), except substituting "2-bromo-6-methylpyridine" for "2-(trifluoromethylsulfonyloxy)-pyridine," gave the title compound: MS (ES+) 571.3 (M+H$^+$).

Example 38

Preparation of 1N-(N-thianaphthenyl-2-carbonyl)-leucinyl)-amino-3N-(3-(5-methyl-2-pyridyl)-phenylacetyl)-amino-propan-2-one a) 1N-(N-Thianaphthenyl-2-carbonyl)-leucinyl)-amino-3N-(3-(5-methyl-2-pyridyl)-phenylacetyl)-amino-propan-2-one Following the general procedure of Example 1(a–e), (g–i), except substituting "2-bromo-5-methylpyridine" for "2-(trifluoromethylsulfonyloxy)-pyridine," gave the title compound: MS (ES+) 571.3 (M+H$^+$).

Example 39

Preparation of 1N-(N-(4-Trifluoromethylbenzoyl)-leucinyl)-amino-3N-(3-(6-methyl-2-pyridyl)-phenylacetyl)-amino-propan-2-one a) 1N-(N-(4-Trifuoromethylbenzoyl)-leucinyl)-amino-3N-(3-(6-methyl-2-pyridyl)-phenylacetyl)-amino-propan-2-one Following the procedure of Example 37, except substituting "4-(trifluoromethyl)benzoic acid" for "thianaphthenyl-2-carboxylic acid," gave the title compound: MS (ES+) 583.3 (M+H$^+$).

Example 40

Preparation of 1N-(N-(4-Trifluoromethylbenzoyl)-leucinyl)-amino-3N-(3-(4-methyl2-pyridyl)-phenylacetyl)-amino-propan-2-one a) 1N-(N-(4-Trifuoromethylbenzoyl)-leucinyl)-amino-3N-(3-(4-methyl-2-pyridyl)-phenylacetyl)-amino-propan-2-one Following the procedure of Example 39, except substituting "2-bromo-4-methylpyridine" for "2-bromo-6-methylpyridine," gave the title compound: MS (ES+) 583.2 (M+H$^+$).

Example 41

Preparation of 1N-(N-(N-tert-butoxycarbonyl-leucinyl)-amino-3N-(3-(2-pyridyl)phenylacetyl)-amino-propan-2-one a) 1-N-(N-(4-Nitrophenylmethoxycarbonyl)amino-3-amino-propan-2-ol A solution of 1,3-diamino-2-propanol (13.5 g, 0.15 mol) in DCM (500 ml) was stirred in an ice bath and treated with a solution of 4-nitrobenzyl chloroformate (6.5 g, 30 mmol) in DCM (50 ml) added dropwise. The mixture was stirred for 30 min, allowed to warm to RT, and stirred for 16 h. The supernatant was decanted from the gum which formed, concentrated in vacuo, and the residue was chromatographed (silica gel, 0–10%–20% MeOH-DCM) to give the title compound (3.6 g, 52%): MS (ES+) 276 (M+H$^+$).

b) 1-N-(N-(4-Nitrophenylmethoxycarbonyl)-amino-3-N-(3-(2-pyridyl)phenylacetyl)-amino-propan-2-ol A mixture of the compound of 1-N-(N-(4-nitrophenylmethoxycarbonyl)amino-3-amino-propan-2-ol (3.6 g, 13.3 mmol), 3-(2-pyridyl)phenyl acetic acid (2.8 g, 13.3 mmol), EDCI (2.56 g, 13.3 mmol), HOBT (1.8 g, 13.3 mmol), and triethylamine (1.9 ml, 13.3 mmol) in DMF was stirred at RT for 16 h, concentrated in vacuo, and the residue was partitioned between 5% aqueous Na$_2$CO$_3$ and DCM. The combined organic extract was dried (MgSO$_4$), filtered, concentrated in vacuo, and the residue was chromatographed (silica gel, 5% MeOH-DCM) to give the title compound (5.35 g 86%): MS (ES+) 465 (M+H$^+$).

c) 1-Amino-3-N-(3-(2-pyridyl)phenylacetyl)-amino-propan-2-ol

1-N-(N-(4-nitrophenylmethoxycarbonyl)-amino-3-N-(3-(2-pyridyl)phenylacetyl)-amino-propan-2-ol (5.35 g, 11.5 mmol) was divided into two portions, and each was suspended in EtOH (35 ml) containing 10% Pd/C (0.25 g) and shaken in a hydrogen atmosphere (45 psi) for 4 h. The mixtures were degassed, filtered, combined, and concentrated in vacuo. The residues were dissolved in DCM, filtered, and the filtrate was dried (MgSO$_4$) and concentrated in vacuo to afford the title compound: MS (ES+) 286 (M+H$^+$).

d) 1N-(N-(N-Tert-butoxycarbonyl-leucinyl)-amino-3N-(3-(2-pyridyl)phenylacetyl)-amino-propan-2-ol A mixture of 1-amino-3-N-(3-(2-pyridyl)phenylacetyl)-amino-propan-2-ol (3.3 g, 11.5 mmol), Boc-L-leucine (2.86 g, 11.5 mmol), EDCI (2.2 g, 11.5 mmol) and HOBT (1.55 g, 11.5 mmol) in DMF was stirred at RT for 16 h, concentrated in vacuo, diluted with 5% aqueous Na$_2$CO$_3$, and extracted with DCM. The combined organic extract was dried (MgSO$_4$), filtered, and concentrated in vacuo. The residue was chromatographed (silica gel, 5% MeOH-DCM) to give the title compound: MS (ES+) 499 (M+H$^+$).

e) 1N-(N-(N-Tert-butoxycarbonyl-leucinyl)-amino-3N-(3-(2-pyridyl)phenylacetyl)-amino-propan-2-one A mixture of 1N-(N-(N-tert-butoxycarbonyl-leucinyl)-amino-3N-(3-(2-pyridyl)phenylacetyl)-amino-propan-2-ol (0.5 g, 1 mmol), sulfur trioxide pyridine complex (0.48 g, 3 mmol), and triethylamine (0.8 ml, 6 mmol) in DMSO (20 ml) was stirred for 2 h. Additional, sulfur trioxide pyridine complex (0.1 g) was added and the mixture stirred for 6 h, concentrated in vacuo, diluted with H$_2$O, and extracted with DCM. The combined organic extract was dried (MgSO$_4$), filtered, concentrated in vacuo and the residue chromatographed (silica gel, 5% MeOH-DCM) to afford the title compound (0.2 g): MS (ES+) 497 (M+H$^+$).

Example 42

Preparation of 1N-(N-Tert-butoxycarbonyl-leucinyl)-amino-3N-(4-nitrophenylmethoxycarbonyl)-amino-propan-2-one a) 1N-(N-Tert-butoxycarbonyl-leucinyl)-amino-3N-(4-nitrophenylmethoxycarbonyl)-amino-propan-2-one Following the procedure of Example 1(a) and (d), except substituting "4-nitrophenylmethoxy-carbonyl chloride and N-methyl morpholine" for "3-(2-pyridyl)-phenyl acetic acid and EDCI" afforded the title compound: MS (ES+) 481 (M+H$^+$).

Example 43

Preparation of 1N-(N-(4-((2-Dimethylamino) ethoxy)-benzoyl)-leucinyl)-amino-3N-(3-(2-pyridyl) phenylacetyl)-amino-propan-2-one a) 1N-(N-(4-((2-Dimethylamino)ethoxy)-benzoyl)-leucinyl)-amino-3N-(3-(2-pyridyl)phenylacetyl)-amino-propan-2-ol Following the procedure of Example 4(a–c), except substituting "4-[(2-dimethylamino)ethoxy]benzoic acid" (*J. Med. Chem.*, 1984, 27, 1057) for "thianaphthenyl-2-carboxylic acid," gave the title compound: MS (ES+) 588 (M+H$^+$).

b) 1N-(N-(4-((2-Dimethylamino)ethoxy)-benzoyl)-leucinyl)-amino-3N-(3-(2-pyridyl)phenylacetyl)-amino-propan-2-one Following the procedure of Example 40(e), except substituting "1N-(N-(4-((2-dimethylamino)ethoxy)-benzoyl)-leucinyl)-amino-3N-(3-(2-pyridyl)phenylacetyl)-amino-propan-2-ol" for "1-N-(N-(N-tert-butoxycarbonyl-leucinyl)-amino-3-N-(3-(2-pyridyl)phenylacetyl)-amino-propan-2-ol" gave the title compound: MS (ES+) 588 (M+H$^+$).

Example 44

Preparation of 1N-(N-(4-((2-dimethylamino) ethoxy)-3-methoxy-benzoyl)-leucinyl)-amino-3N-(3-(2-pyridyl)phenylacetyl)-amino-propan-2-one a) 4-[(2-Dimethylamino)ethoxy]-3-methoxybenzoic Acid Following the general procedure of J. Med. Chem., 1984, 27, 1057, except substituting methyl 4-[(2-dimethylamino) ethoxy]-3-methoxybenzoate (GB 919126) for methyl 4-[2-(1-pyrrolidinyl)ethoxy]benzoate, gave the title compound: MS (ES+) 240 (M+H$^+$).

b) 1N-(N-(4-((2-Dimethylamino)ethoxy)-3-methoxy-benzoyl)-leucinyl)-amino-3N-(3-(2-pyridyl)phenylacetyl)-amino-propan-2-one Following the procedure of Example 43, except substituting "4-[(2-dimethylamino)ethoxy)-3-methoxybenzoic acid " for "4-[(2-dimethylamino)ethoxy]benzoic acid" gave the title compound: MS (ES+) 618 (M+H$^+$).

Example 45

Preparation of 1N-(N-(3-(Dimethylaminoethoxy) benzoyl)-leucinyl)-amino-3N-(3-(2-pyridyl) phenylacetyl)-amino-propan-2-one a) 3-[(2-Dimethylamino)ethoxy]benzoic Acid Following the procedure of J. Med. Chem., 1984, 27, 1057, except substituting methyl 3-hydroxybenzoate for methyl 4-hydroxybenzoate, gave the title compound.

b) 1N-(N-(3-(Dimethylaminoethoxy)benzoyl)-leucinyl)-amino-3N-(3-(2-pyridyl)phenylacetyl)-amino-propan-2-one Following the procedure of Example 43, except substituting "3-[(2-dimethylamino)ethoxy]benzoic acid" for "4-[(2-dimethylamino)ethoxy]benzoic acid" gave the title compound: MS (ES+) 588 (M+H$^+$).

Example 46

Preparation of 1N-(N-(3-((2-Dimethylamino) ethoxy)-4-methoxy-benzoyl)-leucinyl)-amino-3N-(3-(2-pyridyl)phenylacetyl)-amino-propan-2-one a) 3-[(2-Dimethylamino)ethoxy]-4-methoxybenzoic Acid Following the procedure of J. Med. Chem., 1984, 27, 1057, except substituting "methyl 3-hydroxy-4-methoxybenzoate" for "methyl 4-hydroxybenzoate," gave the title compound: MS (ES+) 240 (M+H$^+$).

b) 1N-(N-(3-((2-Dimethylamino)ethoxy)-4-methoxy-benzoyl)-leucinyl)-amino-3N-(3-(2-pyridyl)phenylacetyl)-amino-propan-2-one Following the procedure of Example 4(a–c) and 13(e), except substituting "3-[(2-dimethylamino)ethoxy]-4-methoxybenzoic acid" for "thianaphthenyl-2-carboxylic acid," gave the title compound: MS (ES+) 618.0 (M+H$^+$).

Example 47

Preparation of 1N-(N-(3-((2-(Piperidinyl)ethoxy)-4-methoxy-benzoyl)-leucinyl)-amino-3N-(3-(2-pyridyl)phenylacetyl)-amino-propan-2-one a) 4-Methoxy-3-((2-(piperidin-1-yl)ethoxy)benzoic Acid Following the procedure of Example 44(a), except substituting "2-(piperidin-1-yl)ethyl chloride hydrochloride" for "2-(dimethylamino)ethyl chloride hydrochloride" and "methyl 3-hydroxy-4-methoxybenzoate" for "methyl 3-hydroxybenzoate," gave the title compound: MS (ES+) 280 (M+H$^+$).

b) 1N-(N-(3-((2-(Piperidinyl)ethoxy)-4-methoxy-benzoyl)-leucinyl)-amino-3N-(3-(2-pyridyl)phenylacetyl)-amino-propan-2-one Following the procedure of Example 43(a–b), except substituting "4-methoxy-3-((2-(piperidin-1-yl)ethoxy) benzoic acid" for "4-[(2-dimethylamino)ethoxy]benzoic acid," gave the title compound: MS (ES+) 658 (M+H$^+$).

Example 48

Preparation of 1N-(N-(3-Phenylpropionyl)-leucinyl)-amino-3N-(3-(2-pyridyl)phenylacetyl)-amino-propan-2-one a) 1N-(N-(3-Phenylpropionyl)-leucinyl)-amino-3N-(3-(2-pyridyl)phenylacetyl)-amino-propan-2-one Following the procedure of Example 4(a–d), except substituting "3-phenylpropionic acid" for "thianaphthenyl-2-carboxylic acid," gave the title compound: MS (ES+) 529 (M+H$^+$).

Example 49

Preparation of 1N-(N-(1,2,3,4-Tetrahydroisoquinoline-2-carbonyl)-leucinyl)-amino-3N-(3-(2-pyridyl)phenylacetyl)-amino-propan-2-one a) 1N-(N-(1,2,3,4-Tetrahydroisoquinoline-2-carbonyl)-leucinyl)-amino-3N-(3-(2-pyridyl)phenylacetyl)-amino-propan-2-ol A solution of triphosgene (98 mg, 0.3 mmol) in DCM (10 ml) was stirred in an ice bath and treated with a solution of 1,2,3,4-tetrahydroisoquinoline (133 mg, 1 mmol) and triethylamine (0.42 ml, 3 mmol) in DCM (25 ml) added dropwise. The ice bath was removed and the mixture stirred for 30 min, treated with the compound of Example 1x (c) (0.47 g, mmol), stirred for 16 h, diluted with DCM, washed with 5% aqueous NaHCO$_3$ and then with H$_2$O, dried (MgSO$_4$), filtered, and the filtrate was concentrated in vacuo. The residue was chromatographed (silica gel, 5% MeOH-DCM) to give the title compound. MS (ES+) 558 (M+H$^+$).

b) 1N-(N-(1,2,3,4-Tetrahydroisoquinoline-2-carbonyl)-leucinyl)-amino-3N-(3-(2-pyridyl)phenylacetyl)-amino-propan-2-one Following the procedure of Example 42(b), except substituting the compound of Example "1N-(N-(1,2,3,4-tetrahydroisoquinoline-2-carbonyl)-leucinyl)-amino-3N-(3-(2-pyridyl)phenylacetyl)-amino-propan-2-ol" for "1-N-(N-ten-butoxycarbonyl-leucinyl)-amino-3-N-(4-nitrophenylmethoxy-carbonyl)-amino-propan-2-ol" gave the title compound. MS (ES+) 556 (M+H$^+$).

Example 50

Preparation of 1N-(N-(Piperazine-1-carbonyl)-leucinyl)-amino-3N-(3-(2-pyridyl)phenylacetyl)-amino-propan-2-one a) N-(Piperazin-1-yl)carbonyl-L-leucine A mixture of 1-(tert-butoxycarbonyl)piperazine (60 mg, 0.036 mmol) and N-(4-nitrophenoxycarbonyl)-L-leucine tert-butyl ester (128 mg, 0.36 mmol) in DMF was stirred at 60° C. for 1 h. concentrated in vacuo and the residue treated with 4 M HCl in dioxane (5 ml) for 16 h. The mixture was concentrated in vacuo, azeotroped with toluene and treated with 4 M HCl in dioxane (5 ml) for 16 h. The mixture was concentrated in vacuo to afford the title compound.

b) 1-N-[(4-Tert-Butoxycarbonyl)piperazin-1-yl]carbonyl-L-leucine

A mixture of N-(piperazin-1-yl)carbonyl-L-leucine (120 mg, 0.43 mmol), di-tert-butyl dicarbonate (103 mg, 0.47 mmol), and triethylamine (0.15 ml, 1.1 mmol) in DCM was stirred for 16 h, concentrated in vacuo, and partitioned between DCM and H$_2$O. The combined organic extract was washed with 1 N hydrochloric acid and with H$_2$O, dried (MgSO$_4$), filtered, and the filtrate was concentrated in vacuo to afford the title compound: MS (ES+) 344 (M+H$^+$).

c) 1N-(N-(Piperazine-1-carbonyl)-leucinyl)-amino-3N-(3-(2-pyridyl)phenylacetyl)-amino-propan-2-ol A mixture of 1-N-[(4-tert-butoxycarbonyl)piperazin-1-yl] carbonyl-L-leucine (100 mg, 0.3 mmol), the compound of Example 22x (c) (83 mg, 0.3 mmol), EDCI (67 mg, 0.35 mmol), and HOBT (39 mg, 0.03 mmol) in DMF was stirred for 16 h, concentrated in vacuo, and partitioned between DCM and 5% aqueous Na$_2$CO$_3$. The combined organic extract was washed with H$_2$O, dried (MgSO$_4$), filtered, and the filtrate was concentrated in vacuo. The residue was chromatographed (silica gel, 5% MeOH-DCM) to give the title compound: MS (ES+) 611 (M+H$^+$).

d) 1N-(N-(Piperazine-1-carbonyl)-leucinyl)-amino-3N-(3-(2-pyridyl)phenylacetyl)-amino-propan-2-one Following the procedure of Example 42(b), except substituting "1N-(N-(piperazine-1-carbonyl)-leucinyl)-amino-3N-(3-(2-pyridyl)phenylacetyl)-amino-propan-2-ol" for "1-N-(N-tert-butoxycarbonyl-leucinyl)-amino-3-N-(4-nitrophenylmethoxy-carbonyl)-amino-propan-2-ol," followed by treatment of the residue with 4 M HCl in dioxane, concentration in vacuo, and azeotroping with toluene gave the title compound: MS (ES+) 509 (M+H$^+$).

Example 51

Preparation of 1N-(N-(4-Methylpiperazine-1-carbonyl)-leucinyl)-amino-3N-(3-(2-pyridyl)phenylacetyl)-amino-propan-2-one a) N-(4-Methyl-piperazin-1-yl)carbonyl-L-leucine Following the procedure of Example 50(a), except substituting "1-methyl-piperazine" for "1-(tert-butoxycarbonyl)piperazine," gave the title compound.

b) 1N-(N-(4-Methylpiperazine-1-carbonyl)-leucinyl)-amino-3N-(3-(2-pyridyl)phenylacetyl)-amino-propan-2-one Following the procedure of Example 50(c–d), except substituting "N-(4-methyl-piperazin-1-yl)carbonyl-L-leucine" for "1-N-[(4-tert-butoxycarbonyl)piperazin-1-yl] carbonyl-L-leucine" gave the title compound: MS (ES+) 523 (M+H$^+$).

Example 52

Preparation of 1N-(N-((2-Pyridyl) methoxycarbonyl)-leucinyl)-amino-3N-(3-(2-pyridyl)phenylacetyl)-amino-propan-2-one a) 1N-(N-((2-Pyridyl)methoxycarbonyl)-leucinyl)-amino-3N-(3-(2-pyridyl)phenylacetyl)-amino-propan-2-one Following the procedure of Example 50(c–d), except substituting "N-[(2-pyridinylmethoxy)carbonyl]-L-leucine" (WO 9716433) for "1-N-[(4-tert-butoxycarbonyl)piperazin-1-yl]carbonyl-L-leucine" gave the title compound: MS (ES+) 532 (M+H$^+$).

Example 53

Preparation of 1N-(N-(4-Phenoxybenzenesulfonyl)-leucinyl)-amino-3N-(3-(2-pyridyl)phenylacetyl)-amino-propan-2-one a) 1N-(N-(4-Phenoxybenzenesulfonyl)-leucinyl)-amino-3N-(3-(2-pyridyl)phenylacetyl)-amino-propan-2-one Following the procedure of Example 4(a–d), except substituting "4-phenoxybenzenesulfonyl chloride and N-methyl morpholine" for "thianaphthenyl-2-carboxylic acid and EDCI," gave the title compound: MS (ES+) 629.2 (M+H$^+$).

Example 54

Preparation of 1N-(N-(4-Methoxy-3-(2-(4-morpholinyl)ethoxy)benzoyl)-leucinyl)-amino-3N-(3-(2-pyridyl)phenylacetyl)-amino-propan-2-one a) 3-[2-(4-Morpholinyl)ethoxyl]-4-methoxybenzoic Acid Following the procedure of Example 46(a), except substituting "2-(4-morpholinyl)ethyl chloride hydrochloride" for "2-(piperldin-1-yl)ethyl chloride hydrochloride," gave the title compound.

b) 1N-(N-(4-Methoxy-3-(2-(4-morpholinyl)ethoxy) benzoyl)-leucinyl)-amino-3N-(3-(2-pyridyl)phenylacetyl)-amino-propan-2-one Following the procedure of Example 4(a–c), and Example 3(e) except "3-[2-(4-morpholinyl)ethoxy]-4-methoxybenzoic acid" for "thianaphthenyl-2-carboxylic acid," gave the title compound: MS (ES+) 660.4 (M+H$^+$).

Example 55

Preparation of 1N-(N-(3-Methoxy-2-naphthoyl)-amino-3N-(3-(2-pyridyl)phenylacetyl)-amino-propan-2-one a) 1N-(N-(3-Methoxy-2-naphthoyl)-amino-3N-(3-(2-pyridyl)phenylacetyl)-amino-propan-2-one Following the procedure of Example 4(a–d), except substituting "3-methoxy-2-naphthoic acid" for "thianaphthenyl-2-carboxylic acid", gave the title compound: MS (ES+) 581.2 (M+H$^+$).

Example 56

Preparation 1N-(N-(Cyclohexene-1-carbonyl)-amino-3N-(3-(2-pyridyl)phenylacetyl)-amino-propan-2-one a) 1N-(N-(Cyclohexene-1-carbonyl)-amino-3N-(3-(2-pyridyl)phenylacetyl)-amino-propan-2-one Following the procedure of Example 4(a–d), except substituting "cyclohexene-1-carboxylic acid" for

Example 57

Preparation of 1N-(N-(4-(Benzoyl)benzoyl)-
leucinyl)-amino-3N-(3-(2-pyridyl)phenylacetyl)-
amino-propan-2-one a) 1N-(N-(4-(Benzoyl)benzoyl)-leucinyl)-amino-3N-(3-(2-pyridyl)phenylacetyl)-amino-propan-2-one Following the procedure of Example 4(a–d), except substituting "4-(benzoyl)benzoic acid" for "thianaphthenyl-2-carboxylic acid", gave the title compound: MS (ES+) 605.2 (M+H$^+$).

Example 58

Preparation of 1N-(N-(4-(Phenylmethoxy)benzoyl)-
leucinyl)-amino-3N-(3-(2-pyridyl)phenylacetyl)-
amino-propan-2-one a) 1N-(N-(4-(Phenylmethoxy)benzoyl)-leucinyl)-amino-3N-(3-(2-pyridyl)phenylacetyl)-amino-propan-2-one Following the procedure of Example 4(a–d), except substituting "4-(phenylmethoxy)benzoic acid" for "thianaphthenyl-2-carboxylic acid", gave the title compound: MS (ES+) 607.4 (M+H$^+$);

Example 59

Preparation of 1N-(N-(4-(4-Cyanophenoxy)
benzoyl)-leucinyl)-amino-3N-(3-(2-pyridyl)
phenylacetyl)-amino-propan-2-one a) 1N-(N-(4-(4-Cyanophenoxy)benzoyl)-leucinyl)-amino-3N-(3-(2-pyridyl)phenylacetyl)-amino-propan-2-one Following the procedure of Example 4(a–d), except substituting "4-(4-cyanophenoxy)benzoic acid" for "thianaphthenyl-2-carboxylic acid", gave the title compound: MS (ES+) 618.3 (M+H$^+$).

Example 60

Preparation of 1N-(N-(9-oxo-9H-Xanthene-2-
carbonyl)-leucinyl)-amino-3N-(3-(2-pyridyl)
phenylacetyl)-amino-propan-2-one a) 1N-(N-(9-oxo-9H-Xanthene-2-carbonyl)-leucinyl)-amino-3N-(3-(2-pyridyl)phenylacetyl)-amino-propan-2-one Following the procedure of Example 4(a–d), except substituting "9-oxo9H-xanthene-2-carboxylic acid" for "thianaphthenyl-2-carboxylic acid", gave the title compound: MS (ES+) 619.4 (M+H$^+$).

Example 61

Preparation of 1N-(N-(2-(Pyrrol-1-yl)benzothiazole-
6-carbonyl)-leucinyl)-amino-3N-(3-(2-pyridyl)
phenylacetyl)-amino-propan-2-one a) 1N-(N-(2-(Pyrrol-1-yl)benzothiazole-6-carbonyl)-leucinyl)-amino-3N-(3-(2-pyridyl)phenylacetyl)-amino-propan-2-one Following the procedure of Example 4(a–d), except substituting "N-(2-(pyrrol-1-yl)benzothiazole-6-carboxylic acid" for "thianaphthenyl-2-carboxylic acid", gave the title compound: MS (ES+) 623.4 (M+H$^+$).

Example 62

Preparation of 1N-(N-(4-(Phenylmethyl)benzoyl)-
leucinyl)-amino-3N-(3-(2-pyridyl)phenylacetyl)-
amino-propan-2-one a) 1N-(N-(4-(Phenylmethyl)benzoyl)-leucinyl)-amino-3N-(3-(2-pyridyl)phenylacetyl)-amino-propan-2-one Following the procedure of Example 4(a–d), except substituting "4-(phenylmethyl)benzoic acid" for "thianaphthenyl-2-carboxylic acid", gave the title compound: MS (ES+) 591.3 (M+H$^+$).

Example 63

Preparation of 1N-(N-(4-(4-Nitrophenoxy)benzoyl)-
leucinyl)-amino-3N-(3-(2-pyridyl)phenylacetyl)-
amino-propan-2-one a) 4-(4-Nitrophenoxy)benzoic Acid Following the general procedure of J. Polym. Sci., Polym. Chem. Ed. (1980), 18(10). 3069–80, 4-hydroxybenzoic acid, 1-chloro-4-nitro-benzene and sodium methoxide were heated in DMSO at 130° C. to afford the title compound.

b) 1N-(N-(4-(4-Nitrophenoxy)benzoyl)-leucinyl)-amino-3N-(3-(2-pyridyl)phenylacetyl)-amino-propan-2-one Following the procedure of Example 4(a–d), except substituting "4-(4-nitrophenoxy)benzoic acid " for "thianaphthenyl-2-carboxylic acid", gave the title compound: MS (ES+) 638.3 (M+H$^+$).

Example 64

Preparation of 1N-(N-(4-(4-(Trifluoromethyl)
phenoxy)benzoyl)-leucinyl-amino-3N-(3-(2-
pyridyl)phenylacetyl)-amino-propan-2-one a) 4-(4-(Trifluoromethyl)phenoxy)benzoic Acid Following the general procedure of J. Polym. Sci., Polym. Chem. Ed. (1980), 18(10), 3069–80, 4-hydroxybenzoic acid, 4-nitro-1-(trifluoromethyl)benzene, and sodium hydride in DMF were heated at 130° C. to afford the title compound.

b) 1N-(N-(4-(4-(Trifluoromethyl)phenoxy)benzoyl)-leucinyl)-amino-3N-(3-(2-pyridyl)phenylacetyl)-amino-propan-2-one Following the procedure of Example 4(a–d), except substituting "4-(4-(trifluoromethyl)phenoxy)benzoic acid" for "thianaphthenyl-2-carboxylic acid", gave the title compound: MS (ES+) 661.2 (M+H$^+$).

Example 65

Preparation of 1N-(N-(Benzoxazole-6-carbonyl)-
leucinyl)-amino-3N-(3-(2-pyridyl)phenylacetyl)-
amino-propan-2-one a) 1N-(N-(Benzoxazole-6-carbonyl)-leucinyl)-amino-3N-(3-(2-pyridyl)phenylacetyl)-amino-propan-2-one Following the procedure of Example 4(a–d), except substituting "benzoxazole-6-carboxylic acid" for "thianaphthenyl-2-carboxylic acid", gave the title compound: MS (ES+) 542.3 (M+H$^+$).

Example 66

Preparation of 1N-(N-(Benzoxazole-5-carbonyl)-
leucinyl)-amino-3N-(3-(2-pyridyl)phenylacetyl)-
amino-propan-2-one a) 1N-(N-(Benzoxazole-5-carbonyl)-leucinyl)-amino-3N-(3-(2-pyridyl)phenylacetyl)-amino-propan-2-one Following the procedure of Example 4(a–d), substituting, "benzoxazole-5-carbonyl" for "thianaphthenyl-2-carboxylic acid", gave the title compound: MS (ES+) 542.3 (M+H$^+$).

Example 67

Preparation of 1N-[N-(3-(2-Pyridyl)-benzoyl)-L-
leucinyl)amino-3N-[3-(phenyl)phenylacetyl]amino-
2-propanone a) 1N-[N-(3-(2-Pyridyl)-benzoyl)-L-leucinyl)amino-3N-[3-(phenyl)phenylacetyl]amino-2-propanone Following the procedure of Example 4(a–d), substituting "3-(phenyl)phenylacetic acid" for "3-(2-pyridyl) phenylacetic acid" and "3-(2-pyridyl)benzoic acid" for "thianaphthenyl-2-carboxylic acid" gave the title compound: MS (ES+) 577.3 (M+H$^+$).

Example 68

Preparation of 1N-(N-(2-Quinolinylcarbonyl)-L-leucinyl)amino-3N-[3-(phenyl)phenylacetyl]amino-2-propanone a) 1N-(N-(2-Quinolinylcarbonyl)-L-leucinyl)amino-3N-[3-(phenyl)phenylacetyl]amino-2-propanone Following the procedure of Example 4(a–d), "3-(phenyl) phenylacetic acid" for "3-(2-pyridyl)phenylacetic acid" and "2-quinolinylcarboxylic acid" for "thianaphthenyl-2-carboxylic acid" gave the title compound: MS (ES+) 551.4 (M+H$^+$).

Example 69

Preparation of 1N-(N-(3-Quinolinylcarbonyl)-L-leucinyl)amino-3N-[3-(phenyl)phenylacetyl]amino-2-propanone a) 1N-(N-(3-Quinolnylcarbonyl)-L-leucinyl)amino-3N-[3-(phenyl)phenylacetyl]amino-2-propanone Following the procedure of Example 4(a–d), "3-(phenyl) phenylacetic acid" for "3-(2-pyridyl)phenylacetic acid" and "3-quinolinylcarboxylic acid" for "thianaphthenyl-2-carboxylic acid" gave the title compound: MS (ES+) 551.4 (M+H$^+$).

Example 70

Preparation of 1N-(N-(6-Quinolinylcarbonyl)-L-leucinyl)amino-3N-[3-(phenyl)phenylacetyl]amino-2-propanone a) 1N-(N-(6-Quinolinylcarbonyl)-L-leucinyl)amino-3N-[3-(phenyl)phenylacetyl]amino-2-propanone Following the procedure of Example 4(a–d), "3-(phenyl) phenylacetic acid" for "3-(2-pyridyl)phenylacetic acid" and "6-quinolinylcarboxylic acid" for "thianaphthenyl-2-carboxylic acid" gave the title compound: MS (ES+) 551.4 (M+H$^+$).

Example 71

Preparation of (S)-3N-[N-{-4-Methoxy-3-(N,N-dimethylaminoethyl)oxy}benzoyl-L-leucinyl]amino-1N-[3-(3-(biphenyl)acetyl]amino-2-butanone a) (S)-3N-[N-{4-Methoxy-3-(N,N-dimethylaminoethyl) oxy}benzoyl-L-leucinyl]amino-1N-[3-(3-(biphenyl)acetyl] amino-2-butanone Following the procedure of Example 1(a–e) and (g–h) and Example 3(e), except substituting "3-(phenyl)phenylacetic acid" for "3-(2-pyridyl)phenylacetic acid and "4-methoxy-3-(N,N-dimethylaminoethyl)oxy}benzoic acid" for "thianaphthenyl-2-carboxylic acid" gave the title compound: MS (ES+) 631.4.4 (M+H$^+$).

Example 72

Preparation of (S)-3N-[N-{3-(4-Methylpiperazinyl) benzoyl}-L-leucinyl]amino-1N-[3-(biphenyl)acetyl)]amino-2-butanone a) (S)-3N-[N-{3-(4-Methylpiperazinyl)benzoyl}-L-leucinyl]amino-1N-{3-(biphenyl)acetyl)]amino-2-butanone Following the procedure of Example 1(a–e) and (g–h) and Example 3(e), except substituting "3-(phenyl)phenylacetic acid" for "3-(2-pyridyl)phenylacetic acid and "{3-(4-methylpiperazinyl)benzoic acid" for "thianaphthenyl-2-carboxylic acid" gave the title compound: MS (ES+) 612.4 (M+H$^+$).

Example 73

Preparation of 1N-(N-(3,4-Dichlorobenzoyl)-leucinyl)-amino-3N-(2-pyridyl-sulfonyl)-amino-propan-2-one a) 1-N-(N-Boc-lecinyl)-amino-3-N-(2-pyridyl-sulfonyl)-amino-propan-2-ol 1,3-Diamino-propan-2-ol (3.375 g, 37.5 mmol) was dissolved in DMF (65 ml). Then HOBT-hydrate (5.5 g, 40.7 mmol), Boc-L-leucine (9.34 g, 37.5 mmol), EDCI (7.77 g, 40.7 mmol), NMM (4.4 ml, 40 mmol) were added, and the reaction mixture was stirred for 4 h; then 2-pyridyl-sulfonyl chloride (3.7 g, 20.8 mmol) was added reaction was stirred an additional 2 h. The reaction mixture was concentrated in vacuo, then chromatographed on silica gel to yield a white solid (4.3 g, 26%): MS (ES+) 445.2 (M+H$^+$).

b) 1-N-(Leucinyl)-amino-3-N-(2-pyridyl-sulfonyl)-amino-propan-2-ol

1-N-(N-Boc-leucinyl)-amino-3-N-(2-pyridyl-sulfonyl)-amino-propan-2-ol (2.1 g, 4.73 mmol) was dissolved in 1:1 TFA:DCM (60 ml) and was stirred at RT for 1 h. Toluene (100 ml) was added then the reaction mixture was concentrated in vacuo and was used in the following reaction without further purification (1.6 g, quant.).

c) 1N-(N-(3,4-Dichlorobenzoyl)-leucinyl)-amino-3N-(2-pyridyl-sulfonyl)-amino-propan-2-ol Following the procedure of Example 4(c), except substituting "3,4-dichlorobenzoic acid" for "thianaphthenyl-2-carboxylic acid" gave the title compound: MS (ES+) 517.2, 519.2 (M+H$^+$)

d) 1N-(N-(3,4-Dichlorobenzoyl)-leucinyl)-amino-3N-(2-pyridyl-sulfonyl)-amino-propan-2-one Following the procedure of Example 4(d), of "1N-(N-(3, 4-Dichlorobenzoyl)-leucinyl)-amino-3N-(2-pyridyl-sulfonyl)-amino-propan-2-ol" for "1-N-(N-(thiophene-2-carbonyl)-leucinyl)-amino-3-N-(3-(2-pyridyl)-phenyl acetyl)-amino-propan-2-ol" gave the title compound: MS (ES+) 515.1, 517.1 (M+H$^+$).

Example 74

Preparation of 1N-(N-(Benzofuran-2-carbonyl)-L-leucinyl)amino-3N-(2-pyridylsulfonyl)amino-2-propanone a) 1N-(N-(Benzofuran-2-carbonyl)-L-leucinyl)amino-3N-(2-pyridylsulfonyl)amino-2-propanone Following the procedure of Example 73(a–d) except substituting "benzofuran-2-carboxylic acid" for "thianaphthenyl-2-carboxylic acid" gave the title compound: MS (ES+)487.2 (M+H$^+$).

Example 75

Preparation of (S)-3N-[N-(4-Methoxy-3-(N,N-dimethylaminoethoxy)benzoyl)-L-leucinyl]amino-1N-[(2-pyridyl)sulfonyl]amino-2-butanone

Example 75

Preparation of (S)-3N-[N-(4-Methoxy-3-(N,N-dimethylaminoethoxy)benzoyl)-L-leucinyl]amino-1N-[(2-pyridyl)sulfonyl]amino-2-butanone a) (S)-3N-[N-(4-Methoxy-3-(N,N-dimethylaminoethoxy) benzoyl)-L-leucinyl]amino-1N-[(2-pyridyl)sulfonyl]amino-2-butanone Following the procedure of Example 73(a–c) and Example 3(e) except, substituting "4-methoxy-3-(N,N-dimethylaminoethoxy)benzoic acid" for "thianaphthenyl-2-carboxylic acid" and of "1-N-(leucinyl)-amino-3-N-(2-pyridyl-sulfonyl)-amino-propan-2-ol" for "(S)-3-[(5-Morpholinoethyloxy)benzofuryl-2-carbonyl-L-leucinyl)]amino-1-[3-(2-(1-oxo)pyridyl)phenylacetyl]amino-2-butanol" gave the title compound: MS (ES+) 578.4 (M+H$^+$).

Example 76

Preparation of (S)-3N-(N-(Thianaphthenyl-2-carbonyl)-L-leucinyl)amino-1N-[(2-pyridyl)sulfonyl]amino-2-butanone a) (S)-3N-(N-(Thianaphthenyl-2-carbonyl)-L-leucinyl)amino-1N-[(2-pyridyl)sulfonyl]amino-2-butanone Following the procedure of Example 75 except, substituting "thianaphthenyl-2-carboxylic acid" for "4-methoxy-3-(N,N-dimethylaminoethoxy)benzoic acid" gave the title compound: MS (ES+) 517.1 (M+H$^+$), 1033.6 (2M+H$^+$).

Example 77

Preparation of (S)-3N-[N-(4-Trifluoromethylbenzoyl)-L-leucinyl]amino-1N-[(2-pyridyl)sulfonyl]amino-2-butanone a) (S)-3N-[N-(4-Trifluoromethylbenzoyl)-L-leucinyl]amino-1N-[(2-pyridyl)sulfonyl]amino-2-butanone Following the procedure of Example 75 except, substituting "4-trifluoromethylbenzoic acid" for "4-methoxy-3-(N,N-dimethylaminoethoxy)benzoic acid" gave the title compound: MS (ES+) 529.3.1 (M+H$^+$), 1057.6 (2M+H$^+$).

Example 78

Preparation of 1N-(N-(Benzofuran-2-carbonyl)-L-leucinyl)amino-3N-(2-pyridylsulfonyl)amino-2-propanone a) 1N-(N-(Benzofuran-2-carbonyl)-L-leucinyl)amino-3N-(2-pyridylsulfonyl)amino-2-propanone Following the procedure of Example 73 except, substituting "benzofuran-2-carboxylic acid" for "3,4-dichlorobenzoic acid" gave the title compound: MS (ES+) 487.2 (M+H$^+$).

Example 79

Preparation of 1N-(N-(3,4-Dimethoxybenzoyl)-L-leucinyl)amino-3N-[2-(3-(2-pyridyl)phenyl)-propionyl]amino-2-propanone a) 2-(3-(2-Pyridyl)phenyl)-propionic Acid nBuLi (ml, 2.5 M in hexanes, 52.16 mmol) was added dropwise to a solution of diisopropyl amine (5.2 ml, 37.6 mmol) in THF (20 ml) at −78 degrees C. The reaction was stirred 20 minutes warming to 0 degrees C., then the reaction was cooled to −78 degrees C. The LDA solution was then added dropwise into a cooled solution of 3-(2-pyridyl)phenyl acetic acid (2.0 g, 9.4 mmol) in THF (10 ml) at −78 degrees C. After addition, the reaction mixture was warmed to 0 degrees C., then cooled again to −78 degrees C Methyl iodide (1.2 ml, 18.6 mmol) was then added dropwise. The reaction mixture was stirred for 1 h. then warmed to RT, then quenched with water (20 ml). The THF from the reaction mixture was then removed in vacuo, then the pH of the solution was adjusted to 7 by adding con HCl and pH 7 buffer (1 M). The aqueous reaction mixture was then extracted twice with CHCl$_3$. The combined organic extracts were dried with magnesium sulfate, concentrated in vacuo, and chromatographed (silica gel, 1% AcOH, 3% MeOH—CH$_2$Cl$_2$) to yield a white solid (1.3 g, 61%): MS ES(+) 228.1 (M+H$^+$).

b) 1N-(N-(3,4-Dimethoxybenzoyl)-L-leucinyl)amino-3N-[2-(3-(2-pyridyl)phenyl)-propionyl]amino-2-propanone Following the procedure of Example 4(a–d) except, substituting "2-(3-(2-pyridyl)phenyl)-propionic acid" for "3-(2-pyridyl)-phenyl acetic acid " and "3,4-dimethoxybenzoic acid" for "thianaphthenyl-2-carboxylic acid " gave the title compound: MS (ES+) 575.3 (M+H$^+$).

Example 80

Preparation of (S)-3N-(N-(2-Thianaphthenylcarbonyl)-L-leucinyl)amino-1N-[2-(3-(2-pyridyl)phenyl)-propionyl]amino-2-butanone a) (S)-3N-(N-(2-Thianaphthenylcarbonyl)-L-leucinyl)amino-1N-[2-(3-(2-pyridyl)phenyl)-propionyl]amino-2-butanone Following the procedure of Example 1(c–e) and 1(g–i) except, substituting "2-(3-(2-pyridyl)phenyl)-propionic acid" for "3-(2-pyridyl)-phenyl acetic acid" gave the title compound: MS ES(+) 585.3 (M+H$^+$).

Example 81

Preparation of (S)-3N-(N-(Benzofuranyl-2-carbonyl)-L-leucinyl)amino-1N-[2-(3-(2-pyridyl)phenyl)-propionyl]amino-2-butanone a) (S)-3N-(N-(Benzofuranyl-2-carbonyl)-L-leucinyl)amino-1N-[2-(3-(2-pyridyl)phenyl)-propionyl]amino-2-butanone Following the procedure of Example 80 except, substituting "benzofuranyl-2-carboxylic acid" for "2-thianaphthenylcarboxylic acid" gave the title compound: 569.2 (M+H$^+$).

Example 82

Preparation of (S)-3N-(n-((Morpholinoethoxy)benzofuryl-2-carbonyl)-L-leucinyl)amino-1N-[2-(3-(2-pyridyl)phenyl)-propionyl]amino-2-butanone a) (S)-3N-(n-((Morpholinoethoxy)benzofuryl-2-carbonyl)-L-leucinyl)amino-1N-[2-(3-(2-pyridyl)phenyl)-propionyl]amino-2-butanone Following the procedure of Example 19 except, substituting "2-(3-(2-pyridyl)phenyl)-propionic acid" for "3-(2-pyridyl)-phenyl acetic acid" gave the title compound: MS ES(+) 698.4 (M+H$^+$).

Example 83

Preparation of 1N-(N-(5-(Morpholinoethyloxy)benzofuryl-2-carbonyl)-L-leucinyl)amino-3N-[2-(3-(2-pyridyl)phenyl)-propionyl]amino-2-propanone a) 1N-(N-(5-(Morpholinoethyloxy)benzofuryl-2-carbonyl)-L-leucinyl)amino-3N-[2-(3-(2-pyridyl)phenyl)-propionyl]amino-2-propanone Following the procedure of Example 11 except, substituting "2-(3-(2-pyridyl)phenyl)-propionic acid" for "3-(2-pyridyl)-phenyl acetic acid" gave the title compound: MS ES(+) 684.3 (M+H$^+$).

Example 84

Preparation of (S)-3N-[N-{4-Methoxy-3-(N,N-dimethylaminoethyl)oxy}benzoyl)-L-leucinyl)amino-1N-[2-(3-(2-pyridyl)phenyl)-propionyl]amino-2-butanone a) (S)-3N-[N-(4-Methoxy-3-(N,N-dimethylaminoethyl)oxy)benzoyl)-L-leucinyl)amino-1N-[2-(3-(2-pyridyl)phenyl)-propionyl]amino-2-butanone Following the procedure of Example 71 except, substituting "2-(3-(2-pyridyl)phenyl)-propionic acid" for "3-(2-pyridyl)-phenyl acetic acid" gave the title compound: MS ES(+) 646.4 (M+H$^+$).

Example 85

Preparation of 1N-(N-(Cbz)-L-Leucinyl)amino-3N-[2-methyl-2-[3-(2-pyridyl)phenyl]propionyl]amino]-2-propanone a) 2-Methyl-2-[3-bromophenyl]propionic Acid Methyl Ester 2-Methyl-2-[3-bromophenyl]propionitrile (0.56 g, 2.5 mmol) was refluxed in sulfuric acid (2 ml), water (3 ml) and acetic acid (2.5 ml) overnight. The reaction mixture was poured in water, then extracted with Et2O. The combined organic extracts were dried with magnesium sulfate, filtered, concentrated, and chromatographed (silica gel, 10% EtOAc, 1% HOAc) to give the title compound as a white solid (0.2 g, 36%), which was converted to the methyl ester with diazo methane in Et$_2$O and was used in the next reaction without further purification.

b) 2-Methyl-2-[3-(2-pyridyl)phenyl]propionic Acid Methyl Ester

Following the procedure of Example 1(a), except substituting "2-methyl-2-[3-bromophenyl]propionic acid methyl ester" for "methyl 3-bromophenylacetate" the title compound was prepared: MS (ES) 256.1 (M+H$^+$)

c) 2-Methyl-2-[3-(2-pyridyl)phenyl]propionic Acid

Following the procedure of Example 88(a), except substituting "2-methyl-2-[3-(2-pyridyl)phenyl]propionic acid methyl ester" for "(S)-3-(5-Methoxycarbonylbenzofuryl-2-carbonyl-L-leucinyl)amino-1-[3-(2-pyridyl)phenylacetyl]amino-2-butanone" the title compound was prepared and was used in the next reaction without further purification.

d) 1N-(N-(Cbz)-L-Leucinyl)amino-3N-[2-methyl-2-[3-(2-pyridyl)phenyl]propionyl]amino]-2-propanone Following the procedure of Example 13 except, substituting "2-methyl-2-[3-(2-pyridyl)phenyl]propionic acid" for "3-biphenyl acetic acid" gave the title compound: MS ES(+) 559.2 (M+H$^+$).

Example 86

Preparation of 1N-(N-(Benzofuranyl-2-carbonyl)-L-leucinyl)amino-3N-[[3-(3-methyl)butyl]amino]-2-propanone a) 1N-(N-(Benzofuranyl-2-carbonyl)-L-leucinyl)amino-3N-[[3-(3-methyl)butyl]amino]-2-propanone Following the procedure of Example 4(a–d) except, substituting "4-methyl valeric acid" for "3-(2-pyridyl)-phenyl acetic acid" and "2-benzofuranyl-carboxylic acid" for "thianaphthenyl-2-carboxylic acid" gave the title compound: MS ES(+) 444.4 (M+H$^+$).

Example 87

Preparation of 1N-[N-(5-(Morpholinoethyloxy)benzofuran-2-yl)carbonyl)-L-leucinyl)-amino]-3N-[[3-(3-methyl)butyl-carbonyl]amino]-2-propanone a) 1N-[N-(5-(Morpholinoethyloxy)benzofuran-2-yl)carbonyl)-L-leucinyl)-amino]-3N-[[3-(3-methyl)butyl-carbonyl]amino]-2-propanone Following the procedure of Example 4(a–c) and Example 3(e) except, substituting "4-methyl valeric acid" for "3-(2-pyridyl)-phenyl acetic acid" and "5-(morpholinoethyloxy)benzofuran-2-yl)carboxylic acid " for "thianaphthenyl-2-carboxylic acid" gave the title compound: MS ES(+)573.4 (M+H$^+$).

Example 88

Preparation of (S)-3N-(n-(5-Carboxylbenzofuryl-2-carbonyl)-L-leucinyl)amino-1N-[3-(2-pyridyl)phenylacetyl]amino-2-butanone a) (S)-3N-(n-(5-Carboxylbenzofuryl-2-carbonyl)-L-leucinyl)amino-1N-[3-(2-pyridyl)phenylacetyl]amino-2-butanone (S)-3-(5-Methoxycarbonylbenzofuryl-2-carbonyl-L-leucinyl)amino-1-[3-(2-pyridyl)phenylacetyl]amino-2-butanone (0.095 g, 0.155 mmol) was dissolved in THF: water (5 ml: 1 ml). Then lithium hydroxide hydrate was added (11 mg, 0.26 mmol) and the reaction mixture was refluxed for 1 h. The reaction mixture was then neutralized with pH 7 buffer, extracted with EtOAc, dried with magnesium sulfate, concentrated in vacuo, and chromatographed (silica gel, 1% AcOH. 4% MeOH: CH$_2$Cl$_2$) to yield a white solid (5 mg, 50%): MS ES(+)599.4 (M+H$^+$).

Example 89

Preparation of (+/-)-1,3-N,N-Bis[2-{3-(2-pyridyl)phenyl}-4-methylvaleryl]amino-2-propanone a) 4-Methyl-3-(2-pyridyl)phenyl-pent-4-enoic Acid nBuLi (21 ml, 2.5 M in hexanes, 52.16 mmol) was added dropwise to a solution of diisopropyl amine (5.3 ml, 52.5 mmol) in THF (60 ml) at 0 degrees C. The reaction was stirred 20 minutes, then cooled to –78 degrees C. The LDA solution was then added dropwise into a cooled solution of 3-(2-pyridyl)phenyl acetic acid (5.0 g, 23.5 mmol) in THF (20 ml) at –78 degrees C. After addition, the reaction mixture was warmed to 0 degrees C., then cooled again to –78 degrees C. 3-Bromo-2-methylpropene (3.55 ml, 35.2 mmol) was then added rapidly. The reaction mixture was stirred for 1 h. then quenched with water (20 ml). The THF from the reaction mixture was then removed in vacuo, then the pH of the solution was adjusted to 7 by adding con HCl and pH 7 buffer (1 M). The aqueous reaction mixture was then extracted twice with CHCl$_3$. The combined organic extracts were dried with magnesium sulfate, concentrated in vacuo, and chromatographed (silica gel, 3% MeOH-CH$_2$Cl$_2$) to yield a white solid (4.8 g, 77%): MS ES(+) 268.3 (M+H$^+$).

b) 4-Methyl-3-(2-pyridyl)phenyl-valeric Acid

4-Methyl-3-(2-pyridyl)phenyl-pent-4-enoic acid (0.5 g, 1.87 mmol) was dissolved in EtOH (15 ml) and 6N HCl (0.15 ml). 10% Palladium on carbon (0.08 g) was added and the reaction mixture was stirred under a balloon of hydrogen gas overnight. Then, additional 10% palladium on carbon (0.09 g) and 6N HCl (0.2 ml) were added and the reaction was stirred under a balloon of hydrogen gas for an additional 6 h. The reaction mixture was then filtered through a pad of Celite, azeotroped with toluene (40 ml) and was suspended in water (3 ml). Aqueous sodium hydroxide (1 M) was then added dropwise until the pH was adjusted to 7. The aqueous layer was then extracted with chloroform 2 times and the combined organics were dried with magnesium sulfate, concentrated in vacuo, and triturated with hexanes/Et$_2$O to yield a white solid (0.3 g, 60%): MS ES(+) 270.1 (M+H$^+$).

c) (+/-)-1,3-N,N-Bis[2-{3-(2-pyridyl)phenyl}-4-methylvaleryl]amino-2-propanol

4-Methyl-3-(2-pyridyl)phenyl-valeric acid (54 mg, 0.2 mmol), 1,3-diamino-propan-2-ol (9 mg, 0.1 mmol) was dissolved in DMF (36 ml). Then HOBT-hydrate (30 mg, 0.22 mmol), and EDCI (42 mg. 0.22 mmol) were added, and the reaction mixture was stirred for overnight. The reaction mixture was concentrated in vacuo, then chromatographed on silica gel (3% MeOH—CH$_2$Cl$_2$) to yield the title compound as a white solid (38 mg, 64%): MS (ES+) 593.6 (M+H$^+$).

d) (+/-)-1,3-N,N-Bis[2-{3-(2-pyridyl)phenyl}-4-methylvaleryl]amino-2-propanone

Following the procedure of Example 1(i), except substituting "(+/-)-1,3-N,N-Bis[2-{3-(2-pyridyl)phenyl}-4-methylvaleryl]amino-2-propanol" for "(S)-3N-(N-thianaphthenyl-2-carbonyl-leucinyl)-amino-1-N-(3-{2-(1-oxo)-pyridyl}phenylacetyl)-amino-butan-2-ol", the title compound was prepared: MS (ES+) 591.4 (M+H$^+$).

Example 90

Preparation of (R)-1N-[2-{3-(2-Pyridyl)phenyl}-4-methylvaleryl]amino-1-3N-[(2-pyridyl)sulfonyl]amino-2-butanone a) 1-N-(Boc-leucinyl)-amino-3-N-(2-pyridyl-sulfonyl)-amino-propan-2-ol 2-Pyridine sulfonyl chloride (2.4 g, 13.5 mmol) was added to a solution of (S)-N-Boc-3-amino-2-hydroxy-butyl amine (as described in *J. Med. Chem.* 1989, 32. 165–170) (2.75 g, 13.52 mmol), N-methyl morpholine (2.2 ml. 20 mmol) in DMF (12 ml) at RT. The reaction was stirred for 2 h, then quenched with brine, and extracted with EtOAc, dried with magnesium sulfate, concentrated in vacuo and triturated with 1:1 EtOAc: hexanes to yield the title compound which was used in the next reaction without further purification: MS ES(+) 346.1 (M+H$^+$).

b) 1-N-(Leucinyl)-amino-3-N-(2-pyridyl-sulfonyl)-amino-propan-2-ol

Following the procedure of Example 1(d), except substituting "1-N-(Boc-leucinyl)-amino-3-N-(2-pyridyl-sulfonyl)-amino-propan-2-ol " for "(S)-N-Boc-3-amino-1-N-(3-(2-pyridyl)-phenyl acetyl)-amino-butan-2-ol", gave the title compound: MS (ES+) 246.1 (M+H$^+$).

c) (R)-1N-[2-{3-(2-Pyridyl)phenyl}-4-methylvaleryl]amino-1-3N-[(2-pyridyl)sulfonyl]amino-2-butanol HBTU (0.2 g, 0.53 mmol) was added to a solution of 4-methyl-3-(2-pyridyl)phenyl-valeric acid (0.315 g, 0.5 mmol), 1-N-(leucinyl)-amino-3-N-(2-pyridyl-sulfonyl)-amino-propan-2-ol (0.16 g, 0.5 mmol), N-methyl morpholine (0.23 ml, 2.1 mmol) in DMF (4 ml) and the reaction was stirred at RT for 2 h. The reaction mixture was concentrated in vacuo, chromatographed (silica gel, 4% MeOH-CH$_2$Cl$_2$) to yield the the title compound as a white solid (0.25 g, quant.): MS (ES+) 497.3 (M+H$^+$).

d) (S)-1N-[2-{3-(2-Pyridyl)phenyl}-4-methylvaleryl]amino-1-3N-[(2-pyridyl)sulfonyl]amino-2-butanone Following the procedure of Example 3(e), except substituting "(S)-1N-[2-{3-(2-Pyridyl)phenyl}-4-methylvaleryl]amino-1-3N-((2-pyridyl)sulfonyl]amino-2-butanol" for "(S)-3-[(5-Morpholinoethyloxy)benzofuryl-2-carbonyl-L-leucinyl)]amino-1-[3-(2-(1-oxo)pyridyl)phenylacetyl]amino-2-butanol", gave the title compound: MS (ES+) 495.2 (M+H$^+$).

Example 91

Preparation of (+/-)-1N-[2-{3-(2-Pyridyl)phenyl}-4-methylvaleryl]amino-3N-[3-(3-methyl-2-pyridyl)phenylacetyl]amino-2-propanone a) (+/-)-1N-[2-{3-(2-Pyridyl)phenyl}-4-methylvaleryl]amino-3N-[3-(3-methyl-2-pyridyl)phenylacetyl]amino-2-propanone Following the procedure of Example 41(a–e), except substituting "2-{3-(2-Pyridyl)phenyl}-4-methylvaieric acid" for "3-(2-pyridyl)phenyl acetic acid", and "3-(3-methyl-2-pyridyl)phenylacetic acid" for "Boc-L-leucine", gave the title compound: MS (ES+) 548.9 (M+H$^+$).

Example 92

Preparation of (+/-)-1N-[2-{3-(2-Pyridyl)phenyl}-4-methylvaleryl]amino-3N-(4-fluorophenylsulfonyl)amino-2-propanone a) (+/-)-1N-[2-{-3-(2-Pyridyl)phenyl}-4-methylvaleryl]amino-3N-(4-fluorophenylsulfonyl)amino-2-propanone Following the procedure of Example 91, except substituting "2-{3-(2-Pyridyl)phenyl}-4-methylvaleric acid" for "3-(2-pyridyl)phenyl acetic acid", and "4-fluorophenylsulfonyl chloride and N-methyl morpholine" for "3-(3-methyl-2-pyridyl)phenylacetic acid and EDCI, and HOBT-hydrate" gave the title compound: MS (ES+) 497.8 (M+H$^+$).

Example 93

Preparation of (+/-)-1N-[2-{3-(2-Pyridyl)phenyl}-4-methylvaleryl]amino-3N-(4-trifluoromethylbenzenesulfonyl)amino-2-propanone a) (+1-)-1N-[2-{3-(2-Pyridyl)phenyl}-4-methylvaleryl] amino-3N-(4-trifluoromethylbenzenesulfonyl)amino-2-propanone Following the procedure of Example 92, except substituting "4-trifluoromethylbenzenesulfonyl chloride" for "4-fluorophenylsulfonyl chloride" gave the title compound: MS (ES+) 548.3 (M+H$^+$).

Example 94

Preparation of (+/-)-1N-[2-{3-(2-Benzofuryl)phenyl}-4-methylvaleral]amino-3N-[3-(6-methyl-2-pyridyl)phenylacetyl]amino-2-propanone a) 2-{3-(2-Benzofuryl)phenyl}-4-methyl Valeric Acid Following the procedure of Example 13(a–c) and Example 86(a–b), except substituting "2-Benzofuran boronic acid" for "phenyl boronic acid" gave the title compound: 1H NMR:

b) (+/-)-1N-[2-{3-(2-Benzofuryl)phenyl}-4-methylvaleryl] amino-3N-[3-(6-methyl-2-pyridyl)phenylacetyl]amino-2-propanone Following the procedure of Example 91, except substituting "2-{3-(2-Benzofuryl)phenyl}-4-methylvaleric acid" for "2-{3-(2-Pyridyl)phenyl}-4-methylvaleric acid" gave the title compound: MS (ES+) 588.0 (M+H$^+$).

Example 95

Preparation of (+/-)-1N-[2-{3-(2-Methylphenyl)phenyl}-4-methylvaleryl]amino-3N-[(2-pyridyl)sulfonyl]amino-2-propanone a) 2-{3-(6-Methyl-phenyl)phenyl}-4-methyl-valeric Acid Following the procedure of Example 13(a–c) and Example 86(a–b), except substituting "6-methylphenyl boronic acid" for "phenyl boronic acid" gave the title compound: 1H NMR: 7.2–7.4 (m, 8H), 3.7 (m, 8H), 3.7 (m, 1H), 2.25 (s, 3H), 1.95 (m, 1H), 1.75 (m, 1H), 1.5 (m, 1H0, 0.9 (d, 6H).

b) (+/-)-1N-[2-{3-(2-Methylphenyl)phenyl}-4-methylvaleryl]amino-3N-[(2-pyridyl)sulfonyl]amino-2-propanone Following the procedure of Example 93, except substituting "2-{3-(6-methyl-phenyl)phenyl}-4-methylvaleric acid" for "2-{3-(2-Pyridyl)phenyl}-4-methylvaleric acid" and "2-pyridyl)sulfonyl chloride" for "4-trifluoromethylbenzenesulfonyl chloride" gave the title compound: MS (ES+) 494.4 (M+H$^+$).

Example 96

Preparation of (+/-)-1N-[2-{3-(1-Piperidinyl)phenyl}-4-methylvaleryl]amino-3N-[3-(6-methyl-2-pyridyl)phenylacetyl]amino-2-propanone a) 2-(3-Bromo-phenyl)-4-methyl-4-valeric Acid Methyl Ester Following the procedure of Example 89(a–b) except substituting "3-bromophenyl acetic acid" for "3-(2-pyridyl) phenyl acetic acid" gave the title compound.

b) 2-{3-(1-Piperidinyl)phenyl}-4-methyl-valeric Acid

Following the procedure of Example 16(b) except substituting "2-(3-bromo-phenyl)-4-methyl-4-valeric acid methyl ester" for "3-bromo-benzoic acid" and "piperidine" for "N-methyl piperizine" gave the title compound: MS (ES+) 276.5 (M+H$^+$).

c) (+/−)-1N-[2-{3-(1-Piperidinyl)phenyl)-4-methylvaleryl] amino-3N-[3-(6-methyl-2-pyridyl)phenylacetyl]amino-2-propanone Following the procedure of Example 91, except substituting "2-{3-(1-Piperidinyl)phenyl}-4-methyl-valeric acid" for 2-{3-(2-Pyridyl)phenyl}-4-methylvaleric acid" gave the title compound: MS (ES+) 555.2 (M+H$^+$). (M+H$^+$).

Example 97

Preparation of (+/−)-1N-(N-(2-(3-Biphenyl)-4-methyl-valeryl)-amino-3N-(3-(phenylsulfonyl)-amino-propan-2-one a) (+/−)-1N-(N-(2-(3-Biphenyl)-4-methyl-valeryl)-amino-3N-(3-(phenylsulfonyl)-amino-propan-2-one Following the procedure of Example 90(a–c) and Example 4(d), except substituting "phenyl sulfonyl chloride" for "2-pyridyl sulfonyl chloride" and "2-(3-biphenyl)-4-methyl-valeric acid" for "4-methyl-3-(2-pyridyl)phenyl-valeric acid" gave the title compound: MS (ES+) 479.3 (M+H$^+$).

Example 98

Preparation of (R)-1N-(N-(2-(3-Biphenyl)-4-methyl-valeryl)-amino-3N-(3-(2-pyridyl)phenylacetyl)-amino-propan-2-one a) (R)-2-(3-Biphenyl)-4-methyl-valeric Acid (+/−)-2-(3-biphenyl)-4-methyl-valeric acid (16.6 g, 62 mmol) was dissolved in EtOH (100 ml) and EtOAc (200 ml). (S)-p-Bromo-a-methyl benzyl amine (12.31 g, 62 mmol) was added and the solution was heated to 65 degrees C. until the solid was completely in solution. The solution was cooled in a refrigerator and white crystals formed overnight. The crystals were collected then were dried in vacuo. Four recrystallizations from a 1:2 EtOAc/EtOH yielded crystalline white solid (3.05 g, 21% recovery). Chiral HPLC indicated an enantiomeric ratio of 99.3% (R) and 0.7% (S). The solid was then dissolved in EtOAc, extracted with 1 N aqueous HCl, and the combined organics were dried with magnesium sulfate, filtered, concentrated in vacuo and was used in the next reaction without further purification.

b) (R)-1N-(N-(2-(3-Biphenyl)-4-methyl-valeryl)-amino-3N-(3-(2-pyridyl)phenylacetyl)-amino-propan-2-one Following the procedure of Example 4(a–d) and Example 4(d), except substituting "(R)-2-(3-biphenyl)-4-methyl-valeric acid" for "Boc-L-leucine" gave the title compound: MS (ES+) 534 (M+H$^+$).

Example 99

Preparation of (R)-1N-(N-(2-(3-Biphenyl)-4-methyl-valeryl)-amino-3N-(3-(phenylsulfonyl)-amino-propan-2-one a) (R)-1N-(N-(2-(3-Biphenyl)-4-methyl-valeryl)-amino-3N-(3-(phenylsulfonyl)-amino-propan-2-one Following the procedure of Example 90(a–c) and Example 4(d), except substituting "phenyl sulfonyl chloride" for "2-pyridyl sulfonyl chloride" and "(S)-2-(3-biphenyl)-4-methyl-valeric acid" for "4-methyl-3-(2-pyridyl)phenyl-valeric acid" gave the title compound: MS (ES+) 479.3 (M+H$^+$).

Example 100

Preparation of 1N-(N-(2-Naphthyl-carbonyl)-leucinyl)-amino-3N-(2-pyridyl-sulfonyl)-amino-propan-2-one a) 1N-(N-(2-Naphthyl-carbonyl)-leucinyl)-amino-3N-(2-pyridyl-sulfonyl)-amino-propan-2-one Following the procedure of Example 70(a–d), except substituting "2-naphthoic acid" for "3,4-dichlorobenzoic acid" gave the title compound: MS (ES+)511.3 (M+H$^+$), 1021.5 (2M+H$^+$).

Example 101

Preparation of 1N-(N-(4-Fluorobenzoyl)-leucinyl)-amino-3N-(2-pyridyl-sulfonyl)-amino-propan-2-one a) 1N-(N-(4-Fluorobenzoyl)-leucinyl)-amino-3N-(2-pyridyl-sulfonyl)-amino-propan-2-one Following the procedure of Example 70(a–d), except "4-fluoro-benzoic acid" for "3,4-dichlorobenzoic acid" gave the title compound: MS (ES+) 479.3 (M+H$^+$).

Example 102

Preparation of 3N-(N-(8-Quinoline-2-carbonyl)-L-leucinyl)-amino-1N-(4-methoxy-phenyl)-amino-butane-2-one a) N-(8-Quinoline-2-carbonyl)-L-leucine Methyl Ester Following the procedure of Example 1(h), except "2-quinoline carboxylic acid" for "thianaphthenyl-2-carboxylic acid" and "leucine methyl ester" for "(S)-3N-(leucinyl)-amino-1-N-(3-{2-(1-oxo)-pyridyl}phenylacetyl)-amino-butan-2-ol" gave the title compound: $^1$H NMR: 8.60 (d, J=8.8 Hz, 1H), 8.30 (m, 2H), 8.17 (d, J=8.4 Hz, 1H), 8.17 (d, J=8.0 Hz, 1H), 7.78 (td, J=6.8. 1.6 Hz, 1H), 7.63 (td, J=6.8, 1.6 Hz, 1H), 4.91 (m, 1H), 4.91 (m, 1H), 3.79 (s, 3H), 1.82 (m, 3H), 1.02 (m, 6H).

b) N-(8-Quinoline-2-carbonyl)-L-leucine

Following the procedure of Example 88, except substituting "N-(8-quinoline-2-carbonyl)-L-leucine methyl ester" for "(S)-3-(5-Methoxycarbonylbenzofuryl-2-carbonyl-L-leucinyl)amino-1-[3-(2-pyridyl)phenylacetyl]amino-2-butanone" gave the title compound: $^1$H NMR: 8.67 (br, 1H), 8.26 (br, 2H), 8.12 (m, 1H), 7.80 (m, 1H), 7.71 (br, 1H), 7.57 (m, 1H), 4.87 (br, 1H), 1.78 (br, 3H), 0.95 (br, 6H).

c) N-(8-Quinoline-2-carbonyl-N-L-leucinyl)-L-alanine Methyl Ester

Following the procedure of Example 1(h), except "N-(8-quinoline-2-carbonyl)-L-leucine" for "thianaphthenyl-2-carboxylic acid" and "L-alanine methyl ester" for "(S)-3N-(leucinyl)-amino-1-N-(3-{2-(1-oxo)-pyridyl}phenylacetyl)-amino-butan-2-ol" gave the title compound: MS (ES+) 372.2 (M+H$^+$).

d) N-(8-Quinoline-2-carbonyl-N-L-leucinyl)-L-alanine

Following the procedure of Example 88, except substituting "N-(8-quinoline-2-carbonyl-N-L-leucinyl)-L-alanine methyl ester" for "(S)-3-(5-Methoxycarbonylbenzofuryl-2-carbonyl-L-leucinyl)amino-1-[3-(2-pyridyl)phenylacetyl]amino-2-butanone" gave the title compound: $^1$H NMR: 8.75 (d, J=8.0 Hz, 1H), 8.36 (br, 2H), 8.13 (d, J=8.0 Hz, 1H), 7.83 (d, J=8.0 Hz, 1H), 7.73 (m, 1H), 7.60 (m, 1H), 7.41 (br, 1H), 4.86 (m, 1H), 4.60 (m, 1H), 3.77 (s, 1H), 1.79 (m, 3H), 1.41 (d, J=8.8 Hz, 3H), 0.95 (br, 6H).

e) 3N-(N-(8-Quinoline-2-carbonyl)-L-leucinyl)-amino-1-bromo-butane-2-one

Isobutyl chloroformate (1.56 ml, 12.2 mmol) was added to a solution of N-(8-quinoline-2-carbonyl-N-L-leucinyl)-L-alanine (3.4 g, 9.5 mmol), N-methyl morpholine (12.2 mmol) in THF (20 ml), and the reaction was stirred 15 minutes. Then a solution of diazomethane in Et2O (prepared from 5.2 g of MNNA and 16 ml of 40% KOH in 140 ml of Et2O) was added dropwise. The mixture was stirred for 30 minutes at 0 degrees. Then, a solution of HBr (6.3 ml, 30% in HOAc) was added and the reaction was stirred for 30 minutes at 0 degrees. The reaction mixture was then filtered, partitioned between aqueous sodium bicarbonate and EtOAc. The combined organics were dried over magnesium sulfate, concentrated in vacuo, and used in the next reaction without further purification: MS (ES+) 436.0 (M+H$^+$).

f) 3N-(N-(8-Quinoline-2-carbonyl)-L-leucinyl)-amino-1N-(4-methoxy-phenyl)-amino-butane-2-one 4-Methoxy-aniline (0.2 g, 1.5 mmol) was added to a solution of 3N-(N-(8-quinoline-2-carbonyl)-L-leucinyl)-amino-1-bromo-butane-2-one (0.2 g, 0.46 mmol) in DMF (5 ml) at RT, and the reaction was stirred overnight. The reaction mixture was concentrated in vacuo, then diluted with EtOAc, and extracted with aq. sat. sodium bicarbonate. The combined organics The combined organics were dried over magnesium sulfate, concentrated in vacuo, and used in the next reaction without further purification: MS (ES+) 477.3 (M+H$^+$).

Example 103

Preparation of 3N-(N-(8-Quinoline-2-carbonyl)-L-leucinyl)-amino-1N-(4-fluoro-phenyl)-amino-butane-2-one a) 3N-(N-(8-Quinoline-2-carbonyl)-L-leucinyl)-amino-1N-(4-fluoro-phenyl)-amino-butane-2-one Following the procedure of Example 102(a–f), except substituting "4-fluoro-aniline" for "4-methoxy-aniline" gave the title compound: MS (ES+) 465.3 (M+H$^+$).

Example 104

Preparation of 3N-(N-(8-Quinoline-2-carbonyl)-L-leucinyl)-amino-1N-(4-carboxy methyl-phenyl)-1 amino-butane-2-one a) 3N-(N-(8-Quinoline-2-carbonyl)-L-leucinyl)-amino-1N-(4-carboxy methyl-phenyl)-1-amino-butane-2-one Following the procedure of Example 102(a–f), except substituting "4-carboxymethyl-aniline" for "4-methoxy-aniline" gave the title compound: MS (ES+) 505.2 (M+H$^+$).

Example 105

Preparation of 3N-(N-(8-Quinoline-2-carbonyl)-L-leucinyl)-amino-1N-(4-carboxy-phenyl)-amino-butane-2-one a) 3N-(N-(8-Quinoline-2-carbonyl)-L-leucinyl)-amino-1N-(4-carboxy-phenyl)-amino-butane-2-one Following the procedure of Example 88, except substituting "1-N-(8-quinoline-2-carbonyl-N-L-leucinyl)amino-3-N-amino-(4-carboxy methyl-phenyl)-2-butanone" for "(S)-3-(5-Methoxycarbonylbenzofuryl-2-carbonyl-L-leucinyl)amino-1-[3-(2-pyridyl)phenylacetyl]amino-2-butanone" gave the title compound: MS (ES+) 447.3 (M+H$^+$).

Example 106

Preparation of 3N-(N-(8-Quinoline-2-carbonyl)-L-leucinyl)-amino-1N-(3,4-dimethoxy-phenyl)-amino-butane-2-one a) 3N-(N-(8-Quinoline-2-carbonyl)-L-leucinyl)-amino-1N-(3,4-dimethoxy-phenyl)-amino-butane-2-one Following the procedure of Example 102(a–f), except substituting "3,4-dimethoxy-aniline" for "4-methoxy-aniline" gave the title compound: MS (ES+) 507.2 (M+H$^+$).

Example 107

Preparation of 3N-(N-(8-Quinoline-2-carbonyl)-L-leucinyl)-amino-1N-(2-pyridyl)-amino-butane-2-one a) 3N-(N-(8-Quinoline-2-carbonyl)-L-leucinyl)-amino-1N-(2-pyridyl)-amino-butane-2-one Following the procedure of Example 102(a–f), except substituting "2-amino-pyridine" for "4-methoxy-aniline" gave the title compound: MS (ES+) 453.3 (M+H$^+$).

Example 108

Preparation of 1N-(N-(2-Thianaphthenylcarbonyl)-L-phenylalaninyl)amino-3N-[3-(2-pyridyl)phenylacetyl]amino-2-butanone a) 1N-(N-(2-Thianaphthenylcarbonyl)-L-phenylalaninyl)amino-3N-[3-(2-pyridyl)phenylacetyl]amino-2-butanone Following the procedure of Example 1(a–e), (g–i) except substituting "Boc-L-phenylalanine" for "Boc-L-leucine" gave the title compound: MS (ES+) 605.2 (M+H$^+$).

Example 109

Preparation of 1N-(N-(3,4-Dimethoxy-benzoyl)-L-phenylalaninyl)amino-3N-[3-(2-pyridyl)phenylacetyl]amino-2-butanone a) 1N-(N-(3,4-Dimethoxy-benzoyl)-L-phenylalaninyl)amino-3N-[3-(2-pyridyl)phenylacetyl]amino-2-butanone Following the procedure of Example 1(a–e), (g–i) except substituting "3,4-dimethoxy-benzoic acid" for "2-thianaphthenylcarboxylic acid" and "Boc-L-phenylalanine" for "Boc-L-leucine" gave the title compound: MS (ES+) 609.3 (M+H$^+$).

Example 110

Preparation of 1N-(N-(8-Quinoline-carbonyl)-L-phenylalaninyl)amino-3-[3-(2-pyridyl)phenylacetyl]amino-2-butanone a) 1N-(N-(8-Quinoline-carbonyl)-L-phenylalaninyl)amino-3-[3-(2-pyridyl)phenylacetyl]amino-2-butanone Following the procedure of Example 1(a–e), (g–i) except substituting "8-quinoline-carboxylic acid" for "2-thianaphthenylcarboxylic acid" and "Boc-L-phenylalanine" for "Boc-L-leucine" gave the title compound: MS (ES+) 600.2 (M+H$^+$).

Example 111

Preparation of 1N-(N-(8-Quinoline-carbonyl)-L-leucinyl)amino-3-[3-(2-pyridyl)phenylacetyl]amino-2-butanone a) 1N-(N-(8-Quinoline-carbonyl)-L-leucinyl)amino-3-[3-(2-pyridyl)phenylacetyl]amino-2-butanone Following the procedure of Example 1(a–e), (g–i) except substituting "8-quinoline-carboxylic acid" for "2-thianaphthenylcarboxylic acid", gave the title compound: MS (ES+) 566.2 (M+H$^+$).

Example 112

Preparation of 1N-(N-(5-Quinoline-carbonyl)-L-phenylalaninyl)amino-3-[3-(2-pyridyl)phenylacetyl]amino-2-butanone a) 1N-(N-(5-Quinoline-carbonyl)-L-phenylalaninyl)amino-3-[3-(2-pyridyl)phenylacetyl]amino-2-butanone Following the procedure of Example 1(a–e), (g–i) except substituting "5-quinoline-carboxylic acid" for "2-thianaphthenylcarboxylic acid" gave the title compound: MS (ES+) 566.2 (M+H$^+$).

Example 113

Preparation of 1N-(N-(5-Quinoline-carbonyl)-L-phenylalaninyl)amino-3-[3-(2-pyridyl phenylacetyl] amino-2-butanone a) 1N-(N-(5-Quinoline-carbonyl)-L-phenylalaninyl)amino-3-[3-(2-pyridyl)phenylacetyl]amino-2-butanone Following the procedure of Example 1(a–e), (g–i) except substituting "5-quinoline-carboxylic acid" for "2-thianaphthenylcarboxylic acid" and "Boc-L-phenylalanine" for "Boc-L-leucine" gave the title compound: MS (ES+) 600.2 (M+H$^+$).

Example 114

Preparation of 1N-(N-(4-Trifluoromethyl-benzoyl)-L-phenylalaninyl)amino-3-[3-(2-pyridyl) phenylacetyl]amino-2-butanone a) 1N-(N-(4-Trifluoromethyl-benzoyl)-L-phenylalaninyl) amino-3-[3-(2-pyridyl)phenylacetyl]amino-2-butanone Following the procedure of Example 1(a–e), (g–i) except substituting "4-trifluoromethylbenzoic acid" for "2-thianaphthenylcarboxylic acid" and "Boc-L-phenylalanine" for "Boc-L-leucine" gave the title compound: MS (ES+) 617.1 (M+H$^+$).

Example 115

Preparation of 1N-[N-(5-(Morpholinoethyloxy) benzofuran-2-yl)carbonyl)-L-leucinyl)-amino-3-[[4-fluoro-phenyl sulfonyl]amino]-2-propanone a) 1N-[N-(5-(Morpholinoethyloxy)benzofuran-2-yl) carbonyl)-L-leucinyl)-amino]3-[[4-fluoro-phenyl sulfonyl] amino]-2-propanone Following the procedure of Example 4(a–c) and Example 3(e) except, substituting "4-fluoro-phenyl sulfonyl chloride" for "3-(2-pyridyl)-phenyl acetic acid and EDCI" and "5-(morpholinoethyloxy)benzofuran-2-yl)carboxylic acid" for "thianaphthenyl-2-carboxylic acid" gave the title compound: MS ES(+) 633.3 (M+H$^+$).

Example 116

Preparation of 1N-[N-(5-(Morpholinoethyloxy) benzofuran-2-yl)carbonyl)-L-leucinyl-amino]-3-propionyl-amino]-2-propanone a) 1N-[N-(5-(Morpholinoethyloxy)benzofuran-2-yl) carbonyl)-L-leucinyl-amino]-3-propionyl-amino]-2-propanone Following the procedure of Example 4(a–c) and Example 3(e) except, substituting "propionic acid" for "3-(2-pyridyl)-phenyl acetic acid" and "5-(morpholinoethyloxy) benzofuran-2-yl)carboxylic acid" for "thianaphthenyl-2-carboxylic acid" gave the title compound: MS ES(+) 531.3 (M+H$^+$).

Example 117

Preparation of 1N-[N(5-(Morpholinoethyloxy) benzofuran-2-yl)carbonyl)-L-leucinyl-amino-3N-[[phenylsulfonyl]amino]-2-propanone a) 1N-[N-(5-(Morpholinoethyloxy)benzofuran-2-yl) carbonyl)-L-leucinyl-amino-3N-[[phenylsulfonyl]amino]-2-propanone Following the procedure of Example 4(a–c) and Example 3(e) except, substituting "phenyl sulfonyl chloride" for "3-(2-pyridyl)-phenyl acetic acid and EDCI" and "5-(morpholinoethyloxy)benzofuran-2-yl)carboxylic acid" for "thianaphthenyl-2-carboxylic acid" gave the title compound: MS ES(+) 615.2 (M+H$^+$).

Example 118

Preparation of 1N-(N-(5-(Morpholinoethyloxy) benzofuran-2-yl)carbonyl)-L-leucinyl-amino-3N-[[acetyl]amino]-2-propanone a) 1N-(N-(5-(Morpholinoethyloxy)benzofuran-2-yl) carbonyl)-L-leucinyl-amino-3N-[[(acetyl]amino]-2-propanone Following the procedure of Example 4(a–c) and Example 3(e) except, substituting "acetic acid" for "3-(2-pyridyl)-phenyl acetic acid" and "5-(morpholinoethyloxy) benzofuran-2-yl)carboxylic acid" for "thianaphthenyl-2-carboxylic acid" gave the title compound: MS ES(+) 517.3 (M+H$^+$).

Example 119

Preparation of 1N-(N-(5-(Morpholinoethyloxy) benzofuran-2-yl)carbonyl)-L-leucinyl-amino-3N-[[3-butyl-carbonyl]amino]-2-propanone a) 1N-(N-(5-(Morpholinoethyloxy)benzofuran-2-yl) carbonyl)-L-leucinyl-amino-3N-[[3-butyl-carbonyl]amino]-2-propanone Following the procedure of Example 4(a–c) and Example 3(e) except, substituting "valeric acid" for "3-(2-pyridyl)-phenyl acetic acid" and "5-(morpholinoethyloxy) benzofuran-2-yl)carboxylic acid " for "thianaphthenyl-2-carboxylic acid" gave the title compound: MS ES(+) 559.4 (M+H$^+$).

Example 120

Preparation of (S)-1N-(N-(5-(Morpholinoethyloxy) benzofuryl-2-carbonyl-L-leucinyl-amino-3N-[3-(2-pyridyl)phenylacetyl]amino-2-butanone a) (S)-3N-Boc-amino-1N-(FMOC-leucinyl)-amino-2-butanol (S)-N-Boc-3-amino-2-hydroxy-butyl amine (as described in *J. Med. Chem.* 1989, 32, 165–170) (0.54 g, 2.6 mmol) was dissolved in DMF (20 ml). Then, FMOC-L-leucine (1.1 g, 3.2 mmol), and HOBT (0.61 g, 3.2 mmol), and EDCI (0.43 g, 3.2 mmol) were added, and the reaction mixture was stirred overnight. Then the reaction mixture was concentrated in vacuo, then chromatographed (silica gel, 1:2 hexanes/EtOAc) to yield the title compound as a white solid (0.62 g, 44%): MS (ES+) 540.2 (M+H$^+$).

b) (S)-3N-Boc-amino-1N-(leucinyl)-amino-2-butanol (S)-3N-Boc-amino-1N-(FMOC-leucinyl)-amino-2-butanol (0.62 g, 1.15 mmol) was dissolved in 20% piperidine/DMF (5 ml) and the reaction was stirred for 20 minutes at RT. The reaction mixture was concentrated in vacuo, then chromatographed (silica gel, 1% NH$_4$OH, 10% MeOH, CH$_2$Cl$_2$) to yield the title compound as a white solid (0.34 g, 93%): MS (ES+) 318.3 (M+H$^+$).

c) (S)-3-Boc-amino-1-[(5-Morpholinoethyloxy)benzofuryl-2-carbonyl-L-leucinyl)]amino-2-butanol Following the procedure of Example 3(d) and Example 3(e), except substituting "(S)-3N-Boc-amino-1N-(leucinyl)-amino-2-butanol" for "3-(2-pyridyl)-phenyl acetic acid" and "5-(morpholinoethyloxy)benzofuran-2-yl)carboxylic acid" for "(S)-3N-(leucinyl)-amino-1-N-(3-{2-(1-oxo)- pyridyl}phenylacetyl)-amino-butan-2-ol" gave the title compound: MS ES(+) 591.2 (M+H+).

d) (S)-1N-(N-(5-(Morpholinoethyloxy)benzofuryl-2-carbonyl)-L-leucinyl-amino-, 3-amino-2-butanol Following the procedure of Example 1(d) except, substituting (S)-3-Boc-amino-1-[(5-Morpholinoethyloxy) benzofuryl-2-carbonyl-L-leucinyl)]amino-2-butanol" for "(S)-N-Boc-3-amino-1-N-(3-(2-pyridyl)-phenyl acetyl)-amino-butan-2-ol " gave the title compound: MS ES(+) 491.5 (M+H+).

e) (S)-1N-(N-(5-(Morpholinoethyloxy)benzofuryl-2-carbonyl)-L-leucinyl-amino-3N-[3-(2-pyridyl) phenylacetyl]amino-2-butanol Following the procedure of Example 1(d) except, substituting (S)-3-amino-1-[(5-Morpholinoethyloxy)benzofuryl-2-carbonyl-L-leucinyl)]amino-2-butanol" for "(S)-3N-leucinyl)-amino-1-N-(3-{2-(1-oxo)-pyridyl}phenylacetyl)-amino-butan-2-ol" and "3-(2-pyridyl)phenyl acetic acid" for "thianaphthenyl-2-carboxylic acid" gave the title compound: MS ES(+) 686.3 (M+H+).

f) (S)-1N-(N-(5-(Morpholinoethyloxy)benzofuryl-2-carbonyl)-L-leucinyl-amino-3N-[3-(2-pyridyl) phenylacetyl]amino-2-butanone Following the procedure of Example 3(e) except, substituting "(S)-1N-(N-(5-(Morpholinoethyloxy)benzofuryl-2-carbonyl)-L-leucinyl-amino-3N-[3-(2-pyridyl) phenylacetyl]amino-2-butanol" for "(S)-3-[(5-Morpholinoethyloxy)benzofuryl-2-carbonyl-L-leucinyl) amino-1-[3-(2-(1-oxo)pyridyl)phenylacetyl]amino-2-butanol" gave the title compound: MS ES(+) 684.3 (M+H+).

Example 121

Preparation of 1N-[N-(5-(Morpholinoethyloxy) benzofuran-2-yl)carbonyl)-L-leucinyl-amino-3N-[[2-pyridyl-sulfonyl]amino]-2-propanone a) 1N-[N-(5-(Morpholinoethyloxy)benzofuran-2-yl) carbonyl)-L-leucinyl-amino-3N-[[2-pyridyl-sulfonyl] amino]-2-propanone Following the procedure of Example 4(a–c) and Example 3(e) except, substituting "2-pyridyl sulfonyl chloride" for "3-(2-pyridyl)-phenyl acetic acid and EDCI" and "5-(morpholinoethyloxy)benzofuran-2-yl)carboxylic acid" for "thianaphthenyl-2-carboxylic acid" gave the title compound: MS ES(+) 616 (M+H+).

Example 122

Preparation of (S)-1N-[N-(benzofuran-2-yl-carbonyl)-L-leucinyl-amino-3N-[[2-pyridyl-sulfonyl]amino]-2-butanone a) 1N-[N-(5-(Morpholinoethyloxy)benzofuran-2-yl) carbonyl)-L-leucinyl-amino-3N-[[2-pyridyl-sulfonyl] amino]-2-propanone Following the procedure of Example 4(a–c) and Example 3(e) except, substituting "2-pyridyl sulfonyl chloride" for "3-(2-pyridyl)-phenyl acetic acid and EDCI" and "5-(morpholinoethyloxy)benzofuran-2-yl)carboxylic acid " for "thianaphthenyl-2-carboxylic acid" gave the title compound: MS ES(+) 616.0 (M+H+).

Example 123

Preparation of 1N-[N-(5-(Morpholinoethyloxy) benzofuran-2-yl)carbonyl)-L-leucinyl)-amino]-3-[isopropylsulfonyl]amino]-2-propanone a) 1N-[N-(5-(Morpholinoethyloxy)benzofuran-2-yl) carbonyl)-L-leucinyl)-amino]-3-[isopropylsulfonyl]amino]-2-propanone Following the procedure of Example 115 except, substituting "isopropyl sulfonyl chloride " for "4-fluorophenyl sulfonyl chloride" gave the title compound: MS ES(+) 581.2 (M+H+).

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

We claim:

1. A compound of Formula I:

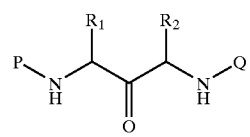

I $R_1$ and $R_2$ are independently H or $C_1$–$C_6$ alkyl, provided that $R_1$ and $R_2$ are not both $C_1$–$C_6$ alkyl;

P is

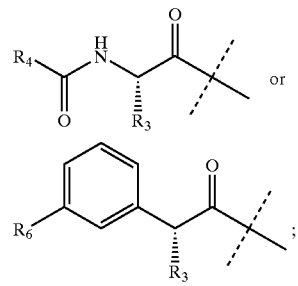

$R_3$ selected from the group consisting of: $CH_2CH(CH_3)_2$, $CH_2CH_2CH_3$, $CH_2CH=CH_2$, or $CH_2Ph$;

$R_4$ is selected from the group consisting of:
  $C_0$–$C_6$ alkyl;
  N-piperizine;
  N-tetrahydroisoquinoline;
  $C_0$–$C_6$ alkyl substituted with phenyl, thiophene, benzthiazole, 2-, 3-, 4-, 5-, 6-, or 7-quinoline, naphthyl, 1-(7-nitro-2,1,3-benzoxadiazol-4-yl)-L-prolyl, $C_0$–$C_6$alkyl pyrazole, N-Cbz-2-(N,N-dimethylamino)ethylglycyl-, N-methyl pyrrole, benzoxazole, benzyloxy, $C_1$–$C_6$ alkoxy; 2, 3, or 4-pyridinyloxy; adamantyl, thieno[3,2-b] thiophene;
  phenyl; thiophene; benzothiophene; benzofuran, benzothiazole; 2-, 3-, 4-, 5-, 6-, or 7-quinoline; naphthyl; and benzoxazole, each independently substituted with one or more of $C_1$–$C_6$ alkyl, halogen, nitro, cyano, hydroxy, $C_1$–$C_6$ alkoxy, trifluoromethyl, carboxyl, carboxy $C_1$–$C_6$ alkyl ester, $(C_0$–$C_6$ alkyl)$_2$N-$C_0$–$C_6$alkyl, $(C_0$–$C_6$ alkyl)$_2$NC$_0$–$C_6$alkoxy, N-($C_0$–$C_6$)-N-piperizine, N-(N-($C_0$–$C_6$)alkyl —N-piperidine)-4-($C_0$–$C_6$) alkyl -amine, $(C_0$–$C_6$ alkyl)$_2$N—$C_0$–$C_6$alkyl-($C_0$–$C_6$ alkyl)-amine, N-morpholino-$C_0$–$C_6$alkyl, N-morpholino-$C_0$–$C_6$alkoxy, phenyl, thiophene, benzthiazole, 2, 3, 4, 5, 6, or 7 quinoline, naphthyl, $C_0$–$C_6$alkyl pyrazole, N-methyl pyrrole, benzoxazole;

benzyloxy substituted with one or more C₁–C₆ alkyl, halogen, nitro, cyano, hydroxy, C₁–C₆ alkoxy, trifluoromethyl, carboxyl, carboxy C₁–C₆ alkyl ester, phenyl, thiophene, benzthiazole, 2, 3, 4, 5, 6, or 7 quinoline, naphthyl, C₀–C₆alkyl pyrazole, N-methyl pyrrole, and benzoxazole;

pyrazine;
pyrimidine;
2,7-dimethylpyrazolo[1,5-a]pyrimidine and 4,7-dimethylpyrazolo[5,1-c][1,2,4]-triazine, R₆ is selected from the group consisting of: phenyl and phenyl substituted with C₀–C₆ alkyl, N-piperidine, benzofuran; or 2, 3, or 4 pyridine;

Q is

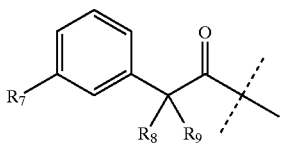

wherein:

R₇ is selected from the group consisting of: phenyl and phenyl substituted with (C₀–C₆ alkyl), N-piperidine, benzofuran; or 2, 3, or 4 pyridine;

R₈ is selected from the group consisting of: H, CH₂CH(CH₃)₂, CH₂CH₂CH₃, and CH₂CH=CH₂, CH₂Ph, when R₉ is H; or R₈ and R₉ are independently selected from the group consisting of: C₁–C₆ alkyl; 3-(2-pyridyl)-phenylacetyl; 3-biphenyl-acetyl; 2-C₁–C₆ alkyl substituted 3-(2-pyridyl)-phenylacetyl; 2-C₁–C₆ alkyl substituted 3-biphenyl-acetyl; 2,2-C₁–C₆ alkyl disubstituted 3-(2-pyridyl)-phenylacetyl; 2,2-C₁–C₆ alkyl disubstituted 3-biphenyl-acetyl; phenyl sulfonyl; 2-, 3-, or 4-pyrine sulfonyl; phenyl; C₀–C₆ alkyl sulfonyl; C₀–C₆ alkyl carbonyl; and phenyl sulfonyl; phenyl; C₀–C₆ alkyl sulfonyl; or C₀–C₆ alkyl carbonyl independently substituted with one or more of C₁–C₆ alkyl, halogen, nitro, cyano, hydroxy, C₁–C₆ alkoxy, trifluoromethyl, carboxyl, carboxy C₁–C₆ alkyl ester, phenyl, thiophene, benzthiazole, 2-, 3-, 4-, 5-, 6-, or 7-quinoline, naphthyl, C₀–C₆alkyl pyrazole, N-methyl pyrrole, benzoxazole;

and pharmaceutically acceptable salts, hydrates and solvates thereof.

2. A compound of claim 1 selected from the group consisting of:

(S)-3N-(N-(thianaphthenyl-2-carbonyl)-leucinyl)-amino-1N-(3-{2-(1-oxo)-pyridyl}phenylacetyl)-amino-butan-2-one;

(S)-3N-(N-(Benzyloxycarbonyl)-L-leucinyl)amino-1N-[3-{2-(1-oxo)-pyridyl}phenylacetyl]amino-2-butanone;

(S)-3N-[N-((5-Morpholinoethyloxy)benzofuryl-2-carbonyl)-L-leucinyl)]amino-1N-[3-(2-(1-oxo)pyridyl) phenylacetyl]amino-2-butanone;

1N-(N-(thiophene-2-carbonyl)-leucinyl)-amino-3N-(3-(2-pyridyl)-phenyl)-acetyl)-amino-propan-2-one; 1N-(N-(3,4-Dichlorobenzoyl)-L-leucinyl)amino-3N-[3-(2-pyridyl)phenylacetyl]amino-2-propanone;

1N-(N-(methylpiperidine-4-carbonyl)-L-leucinyl)amino-3N-[3-(2-pyridyl)phenylacetyl]amino-2-propanone;

1-(N-4-((7-nitro-2,1,3-benzooxadiazole)-L-pyrrolidinyl-)-N-(L-leucinyl))-amino-3N-[3-(2-pyridyl)phenylacetyl]amino-2-propanone;

1N-(N-(5-methylimidazolyl-4-carbonyl)-L-leucinyl) amino-3N-[3-(2-pyridyl)phenylacetyl]amino-2-propanone;

1N-(N-(5-butylpyridine-2-carbonyl)-L-leucinyl)amino-3N-[3-(2-pyridyl)phenylacetyl]amino-2-propanone;

1N-[N-(Cbz-2-(N,N-dimethylamino)ethyl)-glycyl-N-L-leucinyl]amino-3N-[3-(2-pyridyl)phenylacetyl]amino-2-propanone;

1N-[N-(5-(Morpholinoethyloxy)benzofuryl-2-carbonyl)-L-leucinyl]amino-3N-[3-(2-pyridyl)phenylacetyl] amino-2-propanone;

(S)-3N-(N-(Benzothiazolidyl-6-carbonyl)-L-Leucinyl) amino-1N-[3-(2-pyridyl)phenylacetyl]amino-2-butanone;

1N-(N-(Benzyloxy-carbonyl)-L-leucinyl)amino-3N-[3-(phenyl)phenylacetyl]amino-2-propanone;

(S)-3N-(N-(5-Methoxycarbonylbenzofuryl-2-carbonyl)-L-leucinyl)amino-1N-[3-(2-pyridyl)phenylacetyl] amino-2-butanone;

(S)-3N-[N-{4-Methoxy-3-(N,N-dimethylaminoethyl) oxy}benzoyl-L-leucinyl]amino-1N-[3-(2-pyridyl) phenylacetyl]amino-2-butanone;

(S)-3N-[N-(3-(4-Methylpiperazinyl))-benzoyl}-L-leucinyl]amino-1N-[3-(2-pyridyl)phenylacetyl]amino-2-propanone;

(S)-3N-[N-{(N-Methyl-N'-(4-(1-methylpiperidinyl) amino}benzoyl}-L-leucinyl]amino-1N-[3-(2-pyridyl) phenylacetyl]amino-2-butanone;

(S)-3N-[N-{(N-Methyl-N'-(beta-N,N-dimethylaminoethyl)amino}benzoyl-L-leucinyl] amino-1N-[3-(2-pyridyl)phenylacetyl]amino-2-butanone;

(S)-3N-[N-(5-(Morpholinoethyloxy)benzofuryl-2-carbonyl)-L-leucinyl]amino-1N-[3-(2-pyridyl) phenylacetyl]amino-2-butanone;

(S)-3N-{N-(4-Methyl[4-trifluoromethyl)phenyl]thiazole-5-carbonyl)-L-leucinyl)]}-amino-1N-[3-(2-pyridyl) phenylacetyl]amino-2-butanone;

1N-(N-(biphenyl)-4-carbonyl)-leucinyl)-amino-3N-(3-(2-pyridyl)-phenylacetyl)-amino-propan-2-one; 1N-(N-(indole-2-carbonyl)-leucinyl)-amino-3N-(3-(2-pyridyl)-phenylacetyl)-amino-propan-2-one;

1N-(N-(indole-6-carbonyl)-leucinyl)-amino-3N-(3-(2-pyridyl)-phenylacetyl)-amino-propan-2-one;

1N-(N-(adamantane-1-carbonyl)-leucinyl)-amino-3N-(3-(2-pyridyl)-phenylacetyl-amino-propan-2-one;

1N-(N-(1-methoxy-2-naphthoyl)-leucine)-amino-3N-(3-(2-pyridyl)-phenylacetyl)-amino-propan-2-one;

1N-(N-(benzoyl)-leucinyl)-amino-3N-(3-(2-pyridyl)-phenylacetyl)-amino-propan-2-one;

1N-(N-(thieno[3,2-b]thiophene-2-carbonyl)-leucinyl)-amino-3N-(3-(2-pyridyl)-phenylacetyl)-amino-propan-2-one;

1N-(N-(4-cyclohexylbenzoyl)-leucinyl)-amino-3N-(3-(2-pyridyl)-phenylacetyl)-amino-propan-2-one;

1N-(N-(1-methylpyrrole-2-carbonyl)-leucinyl)-amino-3N-(3-(2-pyridyl)-phenyacetyl)-amino-propan-2-one;

1N-(N-(4-methoxybenzoyl)-leucinyl)-amino-3N-(3-(2-pyridyl)-phenylacetyl)-amino-propan-2-one;

1N-(N-(thiophene-3-carbonyl)-leucinyl)-amino-3N-(3-(2-pyridyl)-phenylacetyl)-amino-propan-2-one;

1N-(N-(4-(4'-ethylbiphenyl)carbonyl)-leucinyl)-amino-3N-(3-(2-pyridyl)-phenylacetyl)-amino-propan-2-one;

1N-(N-(pyrazine-2-carbonyl)-leucinyl)-amino-3N-(3-(2-pyridyl)-phenylacetyl)-amino-propan-2-one;

1N-(N-(2,7-dimethylpyrazolo[1,5-a]pyrimidine-6-carbonyl)-leucinyl)-amino-3N-(3-(2-pyridyl)-phenylacetyl)-amino-propan-2-one;

1N-(N-(4,7-dimethylpyrazolo[5,1-c][1,2,4]triazine-3-carbonyl)-leucinyl)-amino-3N-(3-(2-pyridyl)-phenylacetyl)-amino-propan-2-one;

1N-(N-thianaphthenyl-2-carbonyl)-leucinyl)-amino-3N-(3-(6-methyl-2-pyridyl)-phenylacetyl)-amino-propan-2-one;

1N-(N-thianaphthenyl-2-carbonyl)-leucinyl)-amino-3N-(3-(5-methyl-2-pyridyl)-phenylacetyl)-amino-propan-2-one; 1N-(N-(4-trifluoromethylbenzoyl)-leucinyl)-amino-3N-(3-(6-methyl-2-pyridyl)-phenylacetyl)-amino-propan-2-one;

1N-(N-(4-trifluoromethylbenzoyl)-leucinyl)-amino-3N-(3-(4-methyl-2-pyridyl)-phenylacetyl)-amino-propan-2-one;

1N-(N-(N-tert-butoxycarbonyl-leucinyl)-amino-3N-(3-(2-pyridyl)phenylacetyl)-amino-propan-2-one;

1N-(N-(4-((2-dimethylamino)ethoxy)-benzoyl)-leucinyl)-amino-3N-(3-(2-pyridyl)phenylacetyl)-amino-propan-2-one; 1N-(N-(4-((2-dimethylamino)ethoxy)-3-methoxy-benzoyl)-leucinyl)-amino-3N-(3-(2-pyridyl)phenylacetyl)-amino-propan-2-one;

1N-(N-(3-(dimethylaminoethoxy)benzoyl)-leucinyl)-amino-3N-(3-(2-pyridyl)phenylacetyl)-amino-propan-2-one;

1N-(N-(3-((2-dimethylamino)ethoxy)-4-methoxy-benzoyl)-leucinyl)-amino-3N-(3-(2-pyridyl)phenylacetyl)-amino-propan-2-one;

1N-(N-(3-((2-(piperidinyl)ethoxy)4-methoxy-benzoyl)-leucinyl)-amino-3N-(3-(2-pyridyl)phenylacetyl)-amino-propan-2-one;

1N-(N-(1,2,3,4-tetrahydroisoquinoline-2-carbonyl)-leucinyl)-amino-3N-(3-(2-pyridyl)phenylacetyl)-amino-propan-2-one;

1N-(N-(piperazine-1-carbonyl)-leucinyl)-amino-3N-(3-(2-pyridyl)phenylacetyl)-amino-propan-2-one;

1N-(N-(4-methylpiperazine-1-carbonyl)-leucinyl)-amino-3N-(3-(2-pyridyl)phenylacetyl)-amino-propan-2-one; 1N-(N-(4-phenoxybenzenesulfonyl)-leucinyl)-amino-3N-(3-(2-pyridyl)phenylacetyl)-amino-propan-2-one;

1N-(N-(4-methoxy-3-(2-(4-morpholinyl)ethoxy)benzoyl)-leucinyl)-amino-3N-(3-(2-pyridyl)phenylacetyl)-amino-propan-2-one;

1N-(N-(3-methoxy-2-naphthoyl)-amino-3N-(3-(2-pyridyl)phenylacetyl)-amino-propan-2-one;

1N-(N-(cyclohexene-1-carbonyl)-amino-3N-(3-(2-pyridyl)phenylacetyl)-amino-propan-2-one;

1N-(N-(4-(benzoyl)benzoyl)-leucinyl)-amino-3N-(3-(2-pyridyl)phenylacetyl)-amino-propan-2-one;

1N-(N-(4-(phenylmethoxy)benzoyl)-leucinyl)-amino-3N-(3-(2-pyridyl)phenylacetyl)-amino-propan-2-one;

1N-(N-(4-(4-cyanophenoxy)benzoyl)-leucinyl)-amino-3N-(3-(2-pyridyl)phenylacetyl)-amino-propan-2-one;

1N-(N-(9-oxo-9H-xanthene-2-carbonyl)-leucinyl)-amino-3N-(3-(2-pyridyl)phenylacetyl)-amino-propan-2-one;

1N-(N-(2-(pyrrol-1-yl)benzothiazole-6-carbonyl)-leucinyl)-amino-3N-(3-(2-pyridyl)phenylacetyl)-amino-propan-2-one;

1N-(N(4-(phenylmethyl)benzoyl)-leucinyl)-amino-3N-(3-(2-pyridyl)phenylacetyl)-amino-propan-2-one; 1N-(N-(4-(4-nitrophenoxy)benzoyl)-leucinyl)-amino-3N-(3-(2-pyridyl)phenylacetyl)-amino-propan-2-one;

1N-(N-(4-(4-(trifluoromethyl)phenoxy)benzoyl)-leucinyl)-amino-3N-(3-(2-pyridyl)phenylacetyl)-amino-propan-2-one;

1N-(N-(benzoxazole-6-carbonyl)-leucinyl)-amino-3N-(3-(2-pyridyl)phenylacetyl)-amino-propan-2-one; 1N-(N-(benzoxazole-5-carbonyl)-leucinyl)-amino-3N-(3-(2-pyridyl)phenylacetyl)-amino-propan-2-one;

1N-[N-(3-(2-Pyridyl)-benzoyl)-L-leucinyl)amino-3N-[3-(phenyl)phenylacetyl]amino-2-propanone;

1N-(N-(2-Quinolinylcarbonyl)-L-leucinyl)amino-3N-[3-(phenyl)phenylacetyl]amino-2-propanone;

1N-(N-(3-Quinolinylcarbonyl)-L-leucinyl)amino-3N-[3-(phenyl)phenylacetyl]amino-2-propanone;

1N-(N-(6-Quinolinylcarbonyl)-L-leucinyl)amino-3N-[3-(phenyl)phenylacetyl]amino-2-propanone;

(S)-3N-[N-{4-Methoxy-3-(N,N-dimethylaminoethyl)oxy}benzoyl-L-leucinyl]amino-1N-[3-(3-(biphenyl)acetyl]amino-2-butanone;

(S)-3N-[N-{3-(4-Methylpiperazinyl)benzoyl}-L-leucinyl]amino-1N-[3-(biphenyl)acetyl)]amino-2-butanone;

1N-(N-(3,4-Dichlorobenzoyl)-leucinyl)-amino-3N-(2-pyridyl-sulfonyl)-amino-propan-2-one;

1N-(N-(Benzofuran-2-carbonyl)-L-leucinyl)amino-3N-(2-pyrdylsulfonyl)amino-2-propanone;

(S)-3N-[N-(4-Methoxy-3-(N,N-dimethylaminoethoxy)benzoyl)-L-leucinyl]amino-1N-[(2-pyridyl)sulfonyl]amino-2-butanone;

(S)-3N-(N-(Thianaphthenyl-2-carbonyl)-L-leucinyl)amino-1N-[(2-pyridyl)sulfonyl]amino-2-butanone;

(S)-3N-[N-(4-Trifluoromethylbenzoyl)-L-leucinyl]amino-1N-[(2-pyridyl)sulfonyl]amino-2-butanone;

1N-(N-(Benzofuran-2-carbonyl)-L-leucinyl)amino-3N-(2-pyridylsulfonyl)amino-2-propanone;

1N-(N-(3,4-cimethoxybenzoyl)-L-leucinyl)amino-3N-[2-(3-(2-pyridyl)phenyl)-propionyl]amino-2-propanone;

(S)-3N-(N-(2-thianaphthenylcarbonyl)-L-leucinyl)amino-1N-[2-(3-(2-pyridyl)phenyl)-propionyl]amino-2-butanone;

(S)-3N-(N-(benzofuranyl-2-carbonyl)-L-leucinyl)amino-1N-[2-(3-(2-pyridyl)phenyl)-propionyl]amino-2-butanone;

(S)-3N-(n-((Morpholinoethoxy)benzofuryl-2-carbonyl)-L-leucinyl)amino-1N-[2-(3-(2-pyridyl)phenyl)-propionyl]amino-2-butanone;

1N-(N-(5-(Morpholinoethyloxy)benzofuryl-2-carbonyl)-L-leucinyl)amino-3N-[2-(3-(2-pyridyl)phenyl)-propionyl]amino-2-propanone;

(S)-3N-[N-({4-Methoxy-3-(N,N-dimethylaminoethyl)oxy}benzoyl)-L-leucinyl)amino-1N-[2-(3-(2-pyridyl)phenyl)-propionyl]amino-2-butanone, 1N-(N-(Cbz)-L-leucinyl)amino-3N-[2-methyl-2-[3-(2-pyridyl)phenyl]propionyl]amino]-2-propanone;

1N-(N-(benzofuranyl-2-carbonyl)-L-leucinyl)amino-3N-[[3-(3-methyl)butyl]amino]-2-propanone;

1N-[N-(5-(Morpholinoethyloxy)benzofuran-2-y()carbonyl)-L-leucinyl)-amino]-3N-[[3-(3-methyl)butyl-carbonyl]amino]-2-propanone;

(S)-3N-(n-(5-Carboxylbenzofuryl-2-carbonyl)-L-leucinyl)amino-1N-[3-(2-pyridyl)phenylacetyl]amino-2-butanone;

(+/-)-1,3-N,N-Bis[2-{3-(2-pyridyl)phenyl}-4-methylvaleryl]amino-2-propanone;
(R)-1N-[2-{3-(2-Pyridyl)phenyl}-4-methylvaleryl]amino-1-3N-[(2-pyridyl)sulfonyl]amino-2-butanone;
(+/-)-1N-[2-{3-(2-Pyridyl)phenyl}-4-methylvaleryl]amino-3N-3-(3-methyl-2-pyridyl)phenylacetyl]amino-2-propanone;
(+/-)-1N-[2-{3-(2-Pyridyl)phenyl}-4-methylvaleryl]amino-3N-(4-fluorophenylsulfonyl)amino-2-propanone;
(+/-)-1N-[2-{3-(2-Pyridyl)phenyl}-4-methylvaleryl]amino-3N-(4-trifluoromethylbenzenesulfonyl)amino-2-propanone;
(+/-)-1N-[2-{3-(2-Benzofuryl)phenyl}-4-methylvaleryl]amino-3N-[3-(6-methyl-2-pyridyl)phenylacetyl]amino-2-propanone;
(+/-)-1N-[2-{3-(2-Methylphenyl)phenyl}-4-methylvaleryl]amino-3N-[(2-pyridyl)sulfonyl]amino-2-propanone;
(+/-)-1N-[2-{3-(1-Piperidinyl)phenyl}-4-methylvaleryl]amino-3N-[3-(6-methyl-2-pyridyl)phenylacetyl]amino-2-propanone;
(+/-)-1N-(N-(2-(3-biphenyl)-4-methyl-valeryl)-amino-3N-(3-(phenylsulfonyl)-amino-propan-2-one; (R)-1N-(N-(2-(3-biphenyl)-4-methyl-valeryl)-amino-3N-(3-(2-pyridyl)phenylacetyl)-amino-propan-2-one; (R)-1N-(N-(2-(3-biphenyl)-4-methyl-valeryl)-amino-3N-(3-(phenylsulfonyl)-amino-propan-2-one;
1N-(N-(2-naphthyl-carbonyl)-leucinyl)-amino-3N-(2-pyridyl-sulfonyl)-amino-propan-2-one;
1N-(N-(4-fluorobenzoyl)-leucinyl)-amino-3N-(2-pyridyl-sulfonyl)-amino-propan-2-one;
3N-(N-(8-quinoline-2-carbonyl)-L-leucinyl)-amino-1N-(4-methoxy-phenyl)-amino-butane-2-one;
3N-(N-(8-quinoline-2-carbonyl)-L-leucinyl)-amino-1N-(4-fluoro-phenyl)-amino-butane-2-one;
3N-(N-(8-quinoline-2-carbonyl)-L-leucinyl)-amino-1N-(4-carboxy methyl-phenyl)-1-amino-butane-2-one;
3N-(N-(8-quinoline-2-carbonyl)-L-leucinyl)-amino-1N-(4-carboxy-phenyl)-amino-butane-2-one;
3N-(N-(8-quinoline-2-carbonyl)-L-leucinyl)-amino-1N-(3,4-dimethoxy-phenyl)-amino-butane-2-one;
3N-(N-(8-quinoline-2-carbonyl)-L-leucinyl)-amino-1N-(2-pyridyl)-amino-butane-2-one;
1N-(N-(2-thianaphthenylcarbonyl)-L-phenylalaninyl)amino-3N-[3-(2-pyridyl)phenylacetyl]amino-2-butanone;
1N-(N-(3,4-dimethoxy-benzoyl)-L-phenylalaninyl)amino-3N-[3-(2-pyridyl)phenylacetyl]amino-2-butanone;
1N-(N-(8-quinoline-carbonyl)-L-phenylalaninyl)amino-3-[3-(2-pyridyl)phenylacetyl]amino-2-butanone;
1N-(N-(8-quinoline-carbonyl)-L-leucinyl)amino-3-[3-(2-pyridyl)phenylacetyl]amino-2-butanone,
1N-(N-(5-quinoline-carbonyl)-L-phenylalaninyl)amino-3-[3-(2-pyridyl)phenylacetyl]amino-2-butanone;
1N-(N-(5-quinoline-carbonyl)-L-phenylalaninyl)amino-3-[3-(2-pyridyl)phenylacetyl]amino-2-butanone;
1N-(N-(4-trifluoromethyl-benzoyl)-L-phenylalaninyl)amino-3-[3-(2-pyridyl)phenylacetyl]amino-2-butanone;
1N-[N-(5-(Morpholinoethyloxy)benzofuran-2-yl)carbonyl)-L-leucinyl)-amino]-3-[[4-fluoro-phenyl sulfonyl]amino]-2-propanone;
1N-[N-(5-(Morpholinoethyloxy)benzofuran-2-yl)carbonyl)-L-leucinyl-amino]-3-propionyl-amino]-2-propanone;
1N-[N-(5-(Morpholinoethyloxy)benzofuran-2-yl)carbonyl)-L-leucinyl-amino-3N-[[phenylsulfonyl]amino]-2-propanone;
1N-(N-(5-(Morpholinoethyloxy)benzofuran-2-yl)carbonyl)-L-leucinyl-amino-3N-[acetyl]amino]-2-propanone;
1N-(N-(5-(Morpholinoethyloxy)benzofuran-2-yl)carbonyl)-L-leucinyl-amino-3N-[[3-butyl-carbonyl]amino]-2-propanone;
(S)-1N-(N-(5-(Morpholinoethyloxy)benzofuryl-2-carbonyl)-L-leucinyl-amino-3N-[3-(2-pyridyl)phenylacetyl]amino-2-butanone;
1N-[N-(5-(Morpholinoethyloxy)benzofuran-2-yl)carbonyl)-L-leucinyl-amino-3N-[[2-pyridyl-sulfonyl]amino]-2-propanone;
(S)-1N-[N-(benzofuran-2-yl-carbonyl)-L-leucinyl-amino-3N-[[2-pyridyl-sulfonyl]amino]-2-butanone;
1N-[N-(5-(Morpholinoethyloxy)benzofuran-2-yl)carbonyl)-L-leucinyl)-amino]-3-[isopropylsulfonyl]amino]-2-propanone;
1N-(N-(pyrimidine-4-carbonyl)-leucinyl)-amino-3N-(3-(2-pyridyl)-phenylacetyl)-amino-propan-2-one;
1N-(N-(3-phenylpropionyl)-leucinyl)-amino-3N-(3(2-pyridyl)phenylacetyl)-amino-propan-2-one;
(+/-)-1n-(N-(2-(3-biphenyl)-4-methyl-valeryl)-amino-3N-(3-(phenylsulfonyl)-amino-propan-2-one; and
(R)-1N-(N-(2-(3-biphenyl)-4-methyl-valeryl)-amino-3N-(3-(phenylsulfonyl)-amino-propan-2-one.

3. A compound of claim 2 selected from the group consisting of:
(S)-3N-(N-(thianaphthenyl-2-carbonyl)-leucinyl)-amino-1N-(3-{2-(1-oxo)-pyridyl}phenylacetyl)-amino-butan-2-one;
(S)-3N-(N-(Benzyloxycparbonyl)-L-leucinyl)amino-1N-[3-{2-(1-oxo)-pyridyl}phenylacetyl]amino-2-butanone;
(S)-3N-[N-((5-Morpholinoethyloxy)benzofuryl-2-carbonyl)-L-leucinyl)]amino-1N-[3-(2-(1-oxo)pyridyl)phenylacetyl]amino-2-butanone;
1N-(N-(thiophene-2-carbonyl)-leucinyl)-amino-3N-(3-(2-pyridyl)-phenyl acetyl)-amino-propan-2-one; 1N-(N-(3,4-Dichlorobenzoyl)-L-leucinyl)amino-3N-[3-(2-pyridyl)phenylacetyl]amino-2-propanone;
1-(N-4-((7-nitro-2,1,3-benzooxadiazole)-L-pyrrolidinyl-)-N-(L-leucinyl))-amino-3N-[3-(2-pyridyl)phenylacetyl]amino-2-propanone;
1N-(N-(5-butylpyridine-2-carbonyl)-L-leucinyl)amino-3N-[3-(2-pyridyl)phenylacetyl]amino-2-propanone;
1N-[N-(5-(Morpholinoethyloxy)benzofuryl-2-carbonyl)-L-leucinyl]amino-3N-[3-(2-pyridyl)phenylacetyl]amino-2-propanone;
(S)-3N-(N-(Benzothiazolidyl-6-carbonyl)-L-Leucinyl)amino-1N-[3-(2-pyridyl)phenylacetyl]amino-2-butanone;
1N-(N-(Benzyloxy-carbonyl)-L-leucinyl)amino-3N-[3-(phenyl)phenylacetyl]amino-2-propanone;
(S)-3N-(N-(5-Methoxycarbonylbenzofuryl-2-carbonyl)-L-leucinyl)amino-1N-[3-(2-pyridyl)phenylacetyl]amino-2-butanone;
(S)-3N-[N-{4-Methoxy-3-(N,N-dimethylaminoethyl)oxy}benzoyl-L-leucinyl]amino-1N-[3-(2-pyridyl)phenylacetyl]amino-2-butanone;

(S)-3N-[N-(3-(4-Methylpiperazinyl))-benzoyl}-L-leucinyl]amino-1N-[3-(2-pyridyl)phenylacetyl]amino-2-propanone;

(S)-3N-[N-{(N-Methyl-N'-(4-(1-methylpiperidinyl)amino)benzoyl}-L-leucinyl]amino-1N-[3-(2-pyridyl)phenylacetyl]amino-2-butanone;

(S)-3N-[N-{(N-Methyl-N'-(beta-N,N-dimethylaminoethyl)amino}benzoyl-L-leucinyl]amino-1N-[3-(2-pyridyl)phenylacetyl]amino-2-butanone;

(S)-3N-[N-(5-(Morpholinoethyloxy)benzofuryl-2-carbonyl)-L-leucinyl]amino-1N-[3-(2-pyridyl)phenylacetyl]amino-2-butanone;

(S)-3N-{N-(4-Methyl[4-trifluoromethyl)phenyl]thiazole-5-carbonyl)-L-leucinyl)]}-amino-1N-[3-(2-pyridyl)phenylacetyl]amino-2-butanone;

1N-(N-(biphenyl)-4-carbonyl)-leucinyl)-amino-3N-(3-(2-pyridyl)-phenylacetyl)-amino-propan-2-one; 1N-(N-(indole-2-carbonyl)-leucinyl)-amino-3N-(3-(2-pyridyl)-phenylacetyl)-amino-propan-2-one;

1N-(N-(indole-6-carbonyl)-leucinyl)-amino-3N-(3-(2-pyridyl)-phenylacetyl)-amino-propan-2-one;

1N-(N-(adamantane-1-carbonyl)-leucinyl)-amino-3N-(3-(2-pyridyl)-phenylacetyl)-amino-propan-2-one;

1N-(N-(1-methoxy-2-naphthoyl)-leucinyl)-amino-3N-(3-(2-pyridyl)-phenylacetyl)-amino-propan-2-one;

1N-(N-(benzoyl)-leucinyl)-amino-3N-(3-(2-pyridyl)-phenylacetyl)-amino-propan-2-one;

1N-(N-(thieno[3,2-b]thiophene-2-carbonyl)-leucinyl)-amino-3N-(3-(2-pyridyl)-phenylacetyl)-amino-propan-2-one;

1N-(N-(4-cyclohexylbenzoyl)-leucinyl)-amino-3N-(3-(2-pyridyl)-phenylacetyl)-amino-propan-2-one;

1N-(N-(1-methylpyrrole-2-carbonyl)-leucinyl)-amino-3N-(3-(2-pyridyl)-phenylacetyl)-amino-propan-2-one;

1N-(N-(4-methoxybenzoyl)-leucinyl)-amino-3N-(3-(2-pyridyl)-phenylacetyl)-amino-propan-2-one;

1N-(N-(thiophene-3-carbonyl)-leucinyl)-amino-3N-(3-(2-pyridyl)-phenylacetyl)-amino-propan-2-one;

1N-(N-(4-(4'-ethylbiphenyl)carbonyl)-leucinyl)-amino-3N-(3-(2-pyridyl)-phenylacetyl)-amino-propan-2-one;

1N-(N-(pyrazine-2-carbonyl)-leucinyl)-amino-3N-(3-(2-pyridyl)-phenylacetyl)-amino-propan-2-one;

1N-(N-(pyrimidine-4-carbonyl)-leucinyl)-amino-3N-(3-(2-pyridyl)-phenylacetyl)-amino-propan-2-one; 1N-(N-(2,7-dimethylpyrazolo[1,5-a]pyrimidine-6-carbonyl)-leucinyl)-amino-3N-(3-(2-pyridyl)-phenylacetyl)-amino-propan-2-one;

1N-(N-(4,7-dimethylpyrazolo[5,1-c][1,2,4]triazine-3-carbonyl)-leucinyl)-amino-3N-(3-(2-pyridyl)-phenylacetyl)-amino-propan-2-one;

1N-(N-thianaphthenyl-2-carbonyl)-leucinyl)-amino-3N-(3-(6-methyl-2-pyridyl)-phenylacetyl)-amino-propan-2-one;

1N-(N-thianaphthenyl-2-carbonyl)-leucinyl)-amino-3N-(3-(5-methyl-2-pyridyl)-phenylacetyl)-amino-propan-2-one; 1N-(N-(4-trifluoromethylbenzoyl)-leucinyl)-amino-3N-(3-(6-methyl-2-pyridyl)-phenylacetyl)-amino-propan-2-one;

1N-(N-(4-trifluoromethylbenzoyl)-leucinyl)-amino-3N-(3-(4-methyl-2-pyridyl)-phenylacetyl)-amino-propan-2-one;

1N-(N-tert-butoxycarbonyl-leucinyl)-amino-3N-(4-nitrophenylmethoxycarbonyl)-amino-propan-2-one;

1N-(N-(4-((2-dimethylamino)ethoxy)-benzoyl)-leucinyl)-amino-3N-(3-(2-pyridyl)phenylacetyl)-amino-propan-2-one; 1N-(N-(4-((2-dimethylamino)ethoxy)-3-methoxy-benzoyl)-leucinyl)-amino-3N-(3-(2-pyridyl)phenylacetyl)-amino-propan-2-one;

1N-(N-(3-(dimethylaminoethoxy)benzoyl)-leucinyl)-amino-3N-(3-(2-pyridyl)phenylacetyl)-amino-propan-2-one;

1N-(N-(3-((2-dimethylamino)ethoxy)4-methoxy-benzoyl)-leucinyl)-amino-3N-(3-(2-pyridyl)phenylacetyl)-amino-propan-2-one;

1N-(N-(3-((2-(piperidinyl)ethoxy)-4-methoxy-benzoyl)-leucinyl)-amino-3N-(3-(2-pyridyl)phenylacetyl)-amino-propan-2-one;

1N-(N-(3-phenylpropionyl)-leucinyl)-amino-3N-(3-(2-pyridyl)phenylacetyl)-amino-propan-2-one; 1N-(N-(1,2,3,4-tetrahydroisoquinoline-2-carbonyl)-leucinyl)-amino-3N-(3-(2-pyridyl)phenylacetyl)-amino-propan-2-one;

1N-(N-(piperazine-1-carbonyl)-leucinyl)-amino-3N-(3-(2-pyridyl)phenylacetyl)-amino-propan-2-one;

1N-(N-(4-methylpiperazine-1-carbonyl)-leucinyl)-amino-3N-(3-(2-pyridyl)phenylacetyl)-amino-propan-2-one; 1N-(N-((2-pyridyl)methoxycarbonyl)-leucinyl)-amino-3N-(3-(2-pyridyl)phenylacetyl)-amino-propan-2-one;

1N-(N-(4-phenoxybenzenesulfonyl)-leucinyl)-amino-3N-(3-(2-pyridyl)phenylacetyl)-amino-propan-2-one;

1N-(N-(4-methoxy-3-(2-(4-morpholinyl)ethoxy)benzoyl)-leucinyl)-amino-3N-(3-(2-pyridyl)phenylacetyl)-amino-propan-2-one;

1N-(N-(3-methoxy-2-naphthoyl)-amino-3N-(3-(2-pyridyl)phenylacetyl)-amino-propan-2-one;

1N-(N-(cyclohexene-1-carbonyl)-amino-3N-(3-(2-pyridyl)phenylacetyl)-amino-propan-2-one;

1N-(N-(4-(benzoyl)benzoyl)-leucinyl)-amino-3N-(3-(2-pyridyl)phenylacetyl)-amino-propan-2-one;

1N-(N-(4-(phenylmethoxy)benzoyl)-leucinyl)-amino-3N-(3-(2-pyridyl)phenylacetyl)-amino-propan-2-one;

1N-(N-(4-(4-cyanophenoxy)benzoyl)-leucinyl)-amino-3N-(3-(2-pyridyl)phenylacetyl)-amino-propan-2-one;

1N-(N-(9-oxo-9H-xanthene-2-carbonyl)-leucinyl)-amino-3N-(3-(2-pyridyl)phenylacetyl)-amino-propan-2-one;

1N-(N-(2-(pyrrol-1-yl)benzothiazole-6-carbonyl)-leucinyl)-amino-3N-(3-(2-pyridyl)phenylacetyl)-amino-propan-2-one;

1N-(N-(4-(phenylmethyl)benzoyl)-leucinyl)-amino-3N-(3-(2-pyridyl)phenylacetyl)-amino-propan-2-one; 1N-(N-(4-(4-nitrophenoxy)benzoyl)-leucinyl)-amino-3N-(3-(2-pyridyl)phenylacetyl)-amino-propan-2-one;

1N-(N-(4-(4-(trifluoromethyl)phenoxy)benzoyl)-leucinyl)-amino-3N-(3-(2-pyridyl)phenylacetyl)-amino-propan-2-one;

1N-(N-(benzoxazole-6-carbonyl)-leucinyl)-amino-3N-(3-(2-pyridyl)phenylacetyl)-amino-propan-2-one; 1N-(N-(benzoxazole-5-carbonyl)-leucinyl)-amino-3N-(3-(2-pyridyl)phenylacetyl)-amino-propan-2-one;

1N-[N-(3-(2-Pyridyl)-benzoyl)-L-leucinyl)amino-3N-[3-(phenyl)phenylacetyl]amino-2-propanone;

1N-(N-(2-Quinolinylcarbonyl)-L-leucinyl)amino-3N-[3-(phenyl)phenylacetyl]amino-2-propanone;

1N-(N-(3-Quinolinylcarbonyl)-L-leucinyl)amino-3N-[3-(phenyl)phenylacetyl]amino-2-propanone;

1N-(N-(6-Quinolinylcarbonyl)-L-leucinyl)amino-3N-[3-(phenyl)phenylacetyl]amino-2-propanone;

(S)-3N-[N-{4-Methoxy-3-(N,N-dimethylaminoethyl)oxy}benzoyl-L-leucinyl]amino-1N-[3-(3-(biphenyl)acetyl]amino-2-butanone;

(S)-3N-[N-{3-(4-Methylpiperazinyl)benzoyl}-L-leucinyl]amino-1N-[3-(biphenyl)acetyl)]amino-2-butanone;

1N-(N-(3,4-Dichlorobenzoyl)-leucinyl)-amino-3N-(2-pyridyl-sulfonyl)-amino-propan-2-one;

1N-(N-(Benzofuran-2-carbonyl)-L-leucinyl)amino-3N-(2-pyridylsulfonyl)amino-2-propanone;

(S)-3N-[N-(4-Methoxy-3-(N,N-dimethylaminoethoxy)benzoyl)-L-leucinyl]amino-1N-[(2-pyridyl)sulfonyl]amino-2-butanone;

(S)-3N-(N-(Thianaphthenyl-2-carbonyl)-L-leucinyl)amino-1N-[(2-pyridyl)sulfonyl]amino-2-butanone;

(S)-3N-[N-(4-Trifluoromethylbenzoyl)-L-leucinyl]amino-1N-[(2-pyridyl)sulfonyl]amino-2-butanone;

1N-(N-(Benzofuran-2-carbonyl)-L-leucinyl)amino-3N-(2-pyridyl sulfonyl)amino-2-propanone;

1N-(N-(3,4-cimethoxybenzoyl)-L-leucinyl)amino-3N-[2-(3-(2-pyridyl)phenyl)-propionyl]amino-2-propanone;

(S)-3N-(N-(2-thianaphthenylcarbonyl)-L-leucinyl)amino-1N-[2-(3-(2-pyridyl)phenyl)-propionyl]amino2-butanone;

(S)-3N-(N-(benzofuranyl-2-carbonyl)-L-leucinyl)amino-1N-[2-(3-(2-pyridyl)phenyl)-propionyl]amino-2-butanone;

(S)-3N-(n-((Morpholinoethoxy)benzofuryl-2-carbonyl)-L-leucinyl)amino-1N-[2-(3-(2-pyridyl)phenyl)-propionyl]amino-2-butanone;

1N-(N-(5-(Morpholinoethyloxy)benzofuryl-2-carbonyl)-L-leucinyl)amino-3N-[2-(3-(2-pyridyl)phenyl)-propionyl]amino-2-propanone;

(S)-3N-[N-({4-Methoxy-3-(N,N-dimethylaminoethyl)oxy}benzoyl)-L-leucinyl)amino-1N-[2-(3-(2-pyridyl)phenyl)-propionyl]amino-2-butanone;

1N-(N-(Cbz)-L-leucinyl)amino-3N-[2-methyl-2-[3-(2-pyridyl)phenyl]propionyl]amino]-2-propanone;

1N-(N-(benzofuranyl-2-carbonyl)-L-leucinyl)amino-3N-[[3-(3-methyl)butyl]amino]-2-propanone;

1N-[N-(5-(Morpholinoethyloxy)benzofuran-2-yl)carbonyl)-L-leucinyl)-amino]-3N-[[3-(3-methyl)butyl-carbonyl]amino]-2-propanone;

(S)-3N-(n-(5-Carboxylbenzofuryl-2-carbonyl)-L-leucinyl)amino-1N-[3-(2-pyridyl)phenylacetyl]amino-2-butanone;

(+/−)-1N-[2-{3-(2-Pyridyl)phenyl}-4-methylvaleryl]amino-3N-(4-fluorophenylsulfonyl)amino-2-propanone;

(+/−)-1N-(N-(2-(3-biphenyl)-4-methyl-valeryl)-amino-3N-(3-(phenylsulfonyl)-amino-propan-2-one; (R)-1N-(N-(2-(3-biphenyl)-4-methyl-valeryl)-amino-3N-(3-(2-pyridyl)phenylacetyl)-amino-propan-2-one; (R)-1N-(N-(2-(3-biphenyl)-4-methyl-valeryl)-amino-3N-(3-(phenylsulfonyl)-amino-propan-2-one;

1N-(N-(2-naphthyl-carbonyl)-leucinyl)-amino-3N-(2-pyridyl-sulfonyl)-amino-propan-2-one;

1N-(N-(4-fluorobenzoyl)-leucinyl)-amino-3N-(2-pyridyl-sulfonyl)-amino-propan-2-one;

3N-(N-(8-quinoline-2-carbonyl)-L-leucinyl)-amino-1N-(4-methoxy-phenyl)-amino-butane-2-one;

3N-(N-(8-quinoline-2-carbonyl)-L-leucinyl)-amino-1N-(4-fluoro-phenyl)-amino-butane-2-one;

3N-(N-(8-quinoline-2-carbonyl)-L-leucinyl)-amino-1N-(4-carboxy methyl-phenyl)-1-amino-butane-2-one;

3N-(N-(8-quinoline-2-carbonyl)-L-leucinyl)-amino-1N-(4-carboxy-phenyl)-amino-butane-2-one;

3N-(N-(8-quinoline-2-carbonyl)-L-leucinyl)-amino-1N-(3,4-dimethoxy-phenyl)-amino-butane-2-one;

3N-(N-(8-quinoline-2-carbonyl)-L-leucinyl)-amino-1N-(2-pyridyl)-amino-butane-2-one;

1N-(N-(2-thianaphthenylcarbonyl)-L-phenylalaninyl)amino-3N-[3-(2-pyridyl)phenylacetyl]amino-2-butanone;

1N-(N-(3,4-dimethoxy-benzoyl)-L-phenylalaninyl)amino-3N-[3-(2-pyridyl)phenylacetyl]amino-2-butanone;

1N-(N-(8-quinoline-carbonyl)-L-phenylalaninyl)amino-3-[3-(2-pyridyl)phenylacetyl]amino-2-butanone;

1N-(N-(8-quinoline-carbonyl)-L-leucinyl)amino-3-[3-(2-pyridyl)phenylacetyl]amino-2-butanone;

1N-(N-(5-quinoline-carbonyl)-L-phenylalaninyl)amino-3-[3-(2-pyridyl)phenylacetyl]amino-2-butanone;

1N-(N-(5-quinoline-carbonyl)-L-phenylalaninyl)amino-3-[3-(2-pyridyl)phenylacetyl]amino-2-butanone;

1N-(N-(4-trifluoromethyl-benzoyl)-L-phenylalaninyl)amino-3-[3-(2-pyridyl)phenylacetyl]amino-2-butanone;

1N-[N-(5-(Morpholinoethyloxy)benzofuran-2-yl)carbonyl)-L-leucinyl)-amino]-3-[[4-fluoro-phenyl sulfonyl]amino]-2-propanone;

1N-[N-(5-(Morpholinoethyloxy)benzofuran-2-yl)carbonyl)-L-leucinyl-amino]-3-propionyl-amino)-2-propanone;

1N-[N-(5-(Morpholinoethyloxy)benzofuran-2-yl)carbonyl)-L-leucinyl-amino-3N-[[phenylsulfonyl]amino]-2-propanone;

1N-(N-(5-(Morpholinoethyloxy)benzofuran-2-yl)carbonyl)-L-leucinyl-amino-3N-[[acetyl]amino]-2-propanone;

1N-(N-(5-(Morpholinoethyloxybenzofuran-2-yl)carbonyl)-L-leucinyl-amino-3N-[[3-butyl-carbonyl]amino]-2-propanone;

1N-[N-(5-(Morpholinoethyloxy)benzofuran-2-yl)carbonyl)-L-leucinyl-amino-3N-[[2-pyridyl-sulfonyl]amino]-2-propanone;

(S)-1N-[N-(benzofuran-2-yl-carbonyl)-L-leucinyl-amino-3N-[[2-pyridyl-sulfonyl]amino]-2-butanone; and 1N-[N-(5-(Morpholinoethyloxy)benzofuran-2-yl)carbonyl)-L-leucinyl)-amino]-3-[isopropylsulfonyl]amino]-2-propanone.

4. A pharmaceutical composition comprising a compound according to claim 1 and a pharmaceutically acceptable carrier, diluent or excipient.

5. A pharmaceutical composition comprising a compound according to claim 3 and a pharmaceutically acceptable carrier, diluent or excipient.

6. A method of inhibiting a protease selected from the group consisting of a cysteine protease and a serine protease, comprising administering to a patient in need thereof an effective amount of a compound according to claim 1.

7. A method of inhibiting a protease selected from the group consisting of a cysteine protease and a serine protease, comprising administering to a patient in need thereof an effective amount of a compound according to claim 3.

8. A method according to claim 6 wherein said protease is a cysteine protease.

9. A method according to claim 7 wherein said protease is a cysteine protease.

10. A method according to claim 8 wherein said cysteine protease is cathepsin K.

11. A method according to claim 9 wherein said cysteine protease is cathepsin K.

12. A method of treating a disease characterized by bone loss comprising inhibiting said bone loss by administering to a patient in need thereof an effective amount of a compound according to claim 1.

13. A method according to claim 12 wherein said disease is osteoporosis.

14. A method according to claim 12 wherein said disease is periodontitis.

15. A method according to claim 12 wherein said disease is gingivitis.

16. A method of treating a disease characterized by excessive cartilage or matrix degradation comprising inhibiting said excessive cartilage or matrix degradation by administering to a patient in need thereof an effective amount of a compound according to claim 1.

17. A method according to claim 16 wherein said disease is osteoarthritis.

18. A method according to claim 16 wherein said disease is rheumatoid arthritis.

19. A method of treating a disease characterized by bone loss comprising inhibiting said bone loss by administering to a patient in need thereof an effective amount of a compound according to claim 3.

20. A method according to claim 19 wherein said disease is osteoporosis.

21. A method according to claim 19 wherein said disease is periodontitis.

22. A method according to claim 19 wherein said disease is gingivitis.

23. A method of treating a disease characterized by excessive cartilage or matrix degradation comprising inhibiting said excessive cartilage or matrix degradation by administering to a patient in need thereof an effective amount of a compound according to claim 3.

24. A method according to claim 23 wherein said disease is osteoarthritis.

25. A method according to claim 23 wherein said disease is rheumatoid arthritis.

* * * * *